US008815874B2

(12) United States Patent
Yamamoto et al.

(10) Patent No.: US 8,815,874 B2
(45) Date of Patent: Aug. 26, 2014

(54) PYRAZOLOPYRIMIDINE DERIVATIVE

(75) Inventors: Keisuke Yamamoto, Shizuoka (JP); Seiji Aratake, Shizuoka (JP); Kazuki Hemmi, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 221 days.

(21) Appl. No.: 13/582,992

(22) PCT Filed: Mar. 4, 2011

(86) PCT No.: PCT/JP2011/055031
§ 371 (c)(1),
(2), (4) Date: Sep. 5, 2012

(87) PCT Pub. No.: WO2011/108689
PCT Pub. Date: Sep. 9, 2011

(65) Prior Publication Data
US 2013/0102620 A1   Apr. 25, 2013

(30) Foreign Application Priority Data
Mar. 5, 2010 (JP) ................................. 2010-049827

(51) Int. Cl.
*A01N 43/90* (2006.01)
*A61K 31/519* (2006.01)
*A61K 38/00* (2006.01)
*A61P 17/00* (2006.01)
*C07D 491/107* (2006.01)
*C07D 487/04* (2006.01)
*C07D 519/00* (2006.01)
*C07D 487/10* (2006.01)

(52) U.S. Cl.
CPC .......... *C07D 487/04* (2013.01); *C07D 491/107* (2013.01); *C07D 519/00* (2013.01); *C07D 487/10* (2013.01)
USPC ..................................... 514/259.3; 514/18.6

(58) Field of Classification Search
None
See application file for complete search history.

(56) References Cited

U.S. PATENT DOCUMENTS

| 5,055,472 A | 10/1991 | Fujikawa et al. |
| 5,420,128 A | 5/1995 | Kiyokawa et al. |
| 2004/0043998 A1 | 3/2004 | Kato et al. |
| 2006/0089362 A1 | 4/2006 | Seno et al. |
| 2010/0256134 A1 | 10/2010 | Yamamoto et al. |

FOREIGN PATENT DOCUMENTS

| EP | 0 328 700 A1 | 8/1989 |
| EP | 1 149 835 A1 | 10/2001 |
| JP | 04-270285 A | 9/1992 |
| JP | 05-112571 A | 5/1993 |
| JP | 07-157485 A | 6/1995 |
| JP | 09-169762 A | 6/1997 |
| JP | 10-101672 A | 4/1998 |
| JP | 2000-38350 A | 2/2000 |
| WO | WO 98/54093 A1 | 12/1998 |
| WO | WO 00/44754 A1 | 8/2000 |
| WO | WO 00/53605 A1 | 9/2000 |
| WO | WO 00/59908 A2 | 10/2000 |
| WO | WO 02/40485 A1 | 5/2002 |
| WO | WO 03/091256 A1 | 6/2003 |
| WO | WO 2004/110454 A1 | 12/2004 |
| WO | WO 2009/041663 A1 | 4/2009 |
| WO | WO 2009041663 A1 * | 4/2009 |

OTHER PUBLICATIONS

Nagano et al., Soyaku Kagaku, Tokyo Kagaku Dojin, pp. 134-135 (2004).

* cited by examiner

*Primary Examiner* — Jeffrey S. Lundgren
*Assistant Examiner* — Tori M Strong
(74) *Attorney, Agent, or Firm* — Leydig, Voit & Mayer, Ltd.

(57) ABSTRACT

The invention provides a pyrazolopyrimidine derivative of formula (I), wherein, for example, $R^1$ represents $-NR^{1a}R^{1b}$ (wherein $R^{1a}$ and $R^{1b}$ are the same or different and each is a hydrogen atom or aralkyl), $R^2$ represents formula (Ya) [wherein k and m each represents an integer of 0-2, n represents an integer of 0-4, L represents a single bond, $R^5$ represents halogen, $R^6$ represents aryl, X represents $-CR^8$ (wherein $R^8$ represents a hydrogen atom), and $R^7$ represents a hydrogen], $R^3$ represents $-SO_2R^{13a}$ [wherein $R^{13a}$ represents lower alkoxy, $-NR^{13d}C(=O)R^{13e}$ (wherein $R^{13d}$ represents a hydrogen atom, and $R^{13e}$ represents lower alkyl)], and $R^4$ represents a hydrogen atom, or a pharmaceutically acceptable salt thereof. The invention also provides a medicament containing the pyrazolopyrimidine derivative, as well as a method of using the pyrazolopyrimidine derivative to prevent and/or treat skin diseases.

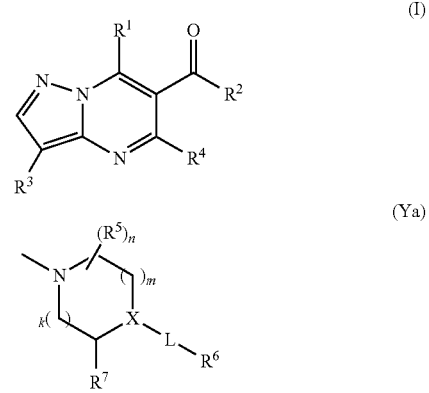

28 Claims, No Drawings

PYRAZOLOPYRIMIDINE DERIVATIVE

CROSS-REFERENCE TO RELATED APPLICATIONS

This patent application is the U.S. national phase of International Patent Application PCT/JP2011/055031, filed on Mar. 4, 2011, which claims the benefit of Japanese Patent Application No. 2010-049827, filed on Mar. 5, 2010, which are incorporated by reference in their entireties herein.

TECHNICAL FIELD

The present invention relates to a pyrazolopyrimidine derivative or a pharmaceutically acceptable salt thereof useful as an agent for the prevention and/or treatment of skin diseases, and the like.

BACKGROUND ART

Pyrazolo[1,5-a]pyrimidine derivatives are known to be useful as corticotrophin-releasing factor receptor antagonist (patent documents 1 and 2), adenosine enhancer (patent document 3), angiotensin II antagonist (patent document 4), tyrosine kinase inhibitor (patent documents 5 and 6), HMG-CoA inhibitor (patent document 7), NAD(H)oxidase inhibitor (patent document 8), adenosine $A_{2A}$ receptor agonist (patent documents 9 and 10), therapeutic drug for prostatic hyperplasia (patent document 11), therapeutic drug for cerebral circulatory disturbance (patent document 12), anti-obesity drug (patent document 13), anti-inflammatory drug (patent document 14) and therapeutic drug for skin diseases (patent document 15).

DOCUMENT LIST

Patent Documents patent document 1: WO00/59908
patent document 2: JP-A-2000-38350
patent document 3: JP-A-10-101672
patent document 4: JP-A-7-157485
patent document 5: WO00/53605
patent document 6: WO98/54093
patent document 7: JP-A-4-270285
patent document 8: WO03/091256
patent document 9: WO02/40485
patent document 10: WO2004/110454
patent document 11: JP-A-5-112571
patent document 12: EP-A-0328700
patent document 13: WO00/44754
patent document 14: JP-A-9-169762
patent document 15: WO2009/041663

SUMMARY OF THE INVENTION

Problems to be Solved by the Invention

An object of the present invention is to provide a pyrazolopyrimidine derivative or a pharmaceutically acceptable salt thereof useful as an agent for the prevention and/or treatment of skin diseases, or the like.

Means of Solving the Problems

The present invention relates to the following (1)-(33).

(1) A pyrazolopyrimidine derivative represented by the formula (I)

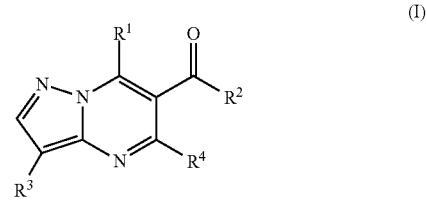

{wherein $R^1$ represents $-NR^{1a}R^{1b}$ (wherein $R^{1a}$ and $R^{1b}$ are the same or different and each represents a hydrogen atom, lower alkyl optionally having substituent(s), cycloalkyl optionally having substituent(s), lower alkoxy optionally having substituent(s), lower alkanoyl optionally having substituent(s), aryl optionally having substituent(s), aralkyl optionally having substituent(s), an aromatic heterocyclic group optionally having substituent(s) or an aliphatic heterocyclic group optionally having substituent(s), or $R^{1a}$ and $R^{1b}$ form, together with the adjacent nitrogen atom, a nitrogen-containing heterocyclic group optionally having substituent(s)), $-OR^{1c}$ (wherein $R^{1c}$ represents a hydrogen atom, lower alkyl optionally having substituent(s), cycloalkyl optionally having substituent(s), aryl optionally having substituent(s), aralkyl optionally having substituent(s), an aromatic heterocyclic group optionally having substituent(s) or an aliphatic heterocyclic group optionally having substituent(s)) or $-SR^{1d}$ (wherein $R^{1d}$ is as defined for the aforementioned $R^{1c}$), $R^2$ represents

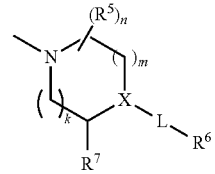

[wherein k and m each represents an integer of 0-2 (wherein the total of k and m is not more than 3), n represents an integer of 0-4, and when n is 2, 3 or 4, respective $R^5$ may be the same or different, L represents a single bond, alkylene, C(=O) or $SO_2$, $R^5$ represents halogen, hydroxy, lower alkyl optionally having substituent(s) or lower alkoxy optionally having substituent(s), $R^6$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s), X represents a nitrogen atom or $-CR^8$ (wherein $R^8$ represents a hydrogen atom, halogen, hydroxy, cyano, lower alkyl optionally having substituent(s) or lower alkoxy optionally having substituent(s), or forms a bond together with $R^7$), and $R^7$ forms a bond together with $R^8$, or represents a hydrogen atom, halogen, hydroxy, lower alkyl optionally having substituent(s) or lower alkoxy optionally having substituent(s)],

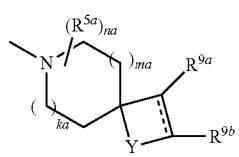

[wherein ka, ma and na are as defined for the aforementioned k, m and n, respectively,
$R^{5a}$ is as defined for the aforementioned $R^5$,
--- represents a single bond or a double bond,
$R^{9a}$ and $R^{9b}$ are the same or different and each represents a hydrogen atom or lower alkyl optionally having substituent(s), or $R^{9a}$ and $R^{9b}$ form, together with the respectively adjacent carbon atoms, an aliphatic ring optionally having substituent(s) or an aromatic ring optionally having substituent(s),
Y represents —CHR$^{10a}$—CHR$^{10b}$— (wherein $R^{10a}$ and $R^{10b}$ are the same or different and each represents a hydrogen atom, hydroxy, lower alkyl optionally having substituent(s) or lower alkoxy optionally having substituent(s), or $R^{10a}$ and $R^{10b}$ form, together with the respectively adjacent carbon atoms, an aliphatic ring optionally having substituent(s)), —CR$^{10c}$=CR$^{10d}$— (wherein $R^{10c}$ and $R^{10d}$ are the same or different and each represents a hydrogen atom or lower alkyl optionally having substituent(s), or $R^{10c}$ and $R^{10d}$ form, together with the respectively adjacent carbon atoms, an aliphatic ring having at least one double bond and optionally having substituent(s) or an aromatic ring optionally having substituent(s)), —Z$^a$—CR$^{11a}$R$^{11b}$— [wherein $R^{11a}$ and $R^{11b}$ are the same or different and each represents a hydrogen atom or lower alkyl optionally having substituent(s), or $R^{11a}$ and $R^{11b}$ form carbonyl together with the adjacent carbon atom, $Z^a$ represents C(=O), O, S, SO, SO$_2$ or NR$^{12}$ (wherein $R^{12}$ represents a hydrogen atom, lower alkyl optionally having substituent(s), lower alkanoyl optionally having substituent(s), lower alkoxycarbonyl optionally having substituent(s) or aralkyl optionally having substituent(s))], or —CR$^{11c}$R$^{11d}$—Z$^b$— (wherein $R^{11c}$, $R^{11d}$ and $Z^b$ are as defined for the aforementioned $R^{11a}$, $R^{11b}$ and $Z^a$, respectively)], or

(wherein $R^z$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s), $R^{5b}$ and $R^{7b}$ are the same or different and each represents halogen, hydroxy, lower alkyl optionally having substituent(s) or lower alkoxy optionally having substituent(s), nb represents an integer of 0-2, nc represents an integer of 0-2, when nb is 2, respective $R^{5b}$ are the same or different, when nc is 2, respective $R^{7b}$ are the same or different), $R^3$ represents —S(O)$_2$R$^{13a}$ [wherein $R^{13a}$ represents hydroxy, lower alkoxy optionally having substituent(s), —NR$^{13b}$R$^{13c}$ (wherein $R^{13b}$ and $R^{13c}$ are the same or different and each represents a hydrogen atom, lower alkyl optionally having substituent(s), lower alkoxy optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), or $R^{13b}$ and $R^{13c}$ form, together with the adjacent nitrogen atom, a nitrogen-containing heterocyclic group optionally having substituent(s)), —NR$^{13d}$C(=O)R$^{13e}$ (wherein $R^{13d}$ represents a hydrogen atom, lower alkyl optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), $R^{13e}$ represents a hydrogen atom, lower alkyl optionally having substituent(s), cycloalkyl optionally having substituent(s), aralkyl optionally having substituent(s), lower alkoxy optionally having substituent(s), N-mono-lower alkylamino optionally having substituent(s), N,N-di-lower alkylamino optionally having substituent(s), N-cycloalkylamino optionally having substituent(s), N-mono-arylamino optionally having substituent(s), N,N-di-arylamino optionally having substituent(s), aryl optionally having substituent(s), an aromatic heterocyclic group optionally having substituent(s) or an aliphatic heterocyclic group optionally having substituent(s)), —NR$^{13f}$C(=S)R$^{13g}$ (wherein $R^{13f}$ and $R^{13g}$ are as defined for the aforementioned $R^{13d}$ and $R^{13e}$, respectively) or —NR$^{13h}$S(O)$_2$R$^{14}$ (wherein $R^{13h}$ is as defined for the aforementioned $R^{13d}$, $R^{14}$ represents lower alkyl optionally having substituent(s), cycloalkyl optionally having substituent(s), N-mono-lower alkylamino optionally having substituent(s), N,N-di-lower alkylamino optionally having substituent(s), aryl optionally having substituent(s), aralkyl optionally having substituent(s), an aromatic heterocyclic group optionally having substituent(s) or an aliphatic heterocyclic group optionally having substituent(s))], and
$R^4$ represents a hydrogen atom, halogen, lower alkyl optionally having substituent(s), aralkyl optionally having substituent(s), —NR$^{15a}$R$^{15b}$ (wherein $R^{15a}$ and $R^{15b}$ are as defined for the aforementioned $R^{1a}$ and $R^{1b}$, respectively), —OR$^{15c}$ (wherein $R^{15c}$ is as defined for the aforementioned $R^{1c}$), or —SR$^{15d}$ (wherein $R^{15d}$ is as defined for the aforementioned $R^{1c}$) or a pharmaceutically acceptable salt thereof.

(2) A pyrazolopyrimidine derivative represented by the formula (IA)

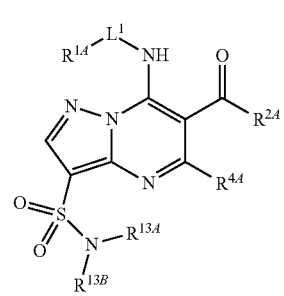

(IA)

{wherein
$L^1$ represents a single bond or methylene,
$R^{1A}$ represents lower alkyl optionally having substituent(s), an aralkyl optionally having substituent(s), cycloalkyl optionally having substituent(s), aryl optionally having substituent(s), an aromatic heterocyclic group optionally having substituent(s) or an aliphatic heterocyclic group optionally having substituent(s), $R^{2A}$ represents

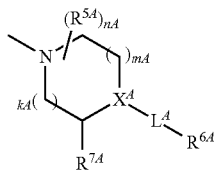

[wherein nA represents an integer of 0-2, and when nA is 2, respective $R^{5A}$s may be the same or different,
kA, mA and $L^A$ are as defined for the aforementioned k, m and l, respectively,
$R^{5A}$ represents halogen or lower alkyl,
$R^{6A}$ represents cycloalkyl optionally having substituent(s), aryl optionally having substituent(s), an aromatic heterocyclic group optionally having substituent(s) or an aliphatic heterocyclic group optionally having substituent(s),
$X^A$ represents a nitrogen atom or —$CR^{8A}$ (wherein $R^{8A}$ represents a hydrogen atom, halogen or lower alkyl, or forms a bond together with $R^{7A}$), and
$R^{7A}$ forms a bond together with $R^{8A}$, or represents a hydrogen atom, halogen or lower alkyl],

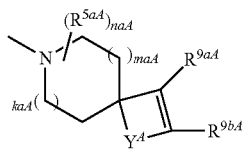

[wherein naA and $R^{5aA}$ are as defined for the aforementioned nA and $R^{5A}$, respectively,
maA and kaA are as defined for the aforementioned ma and ka, respectively,
$R^{9aA}$ and $R^{9bA}$ form, together with the respectively adjacent carbon atoms, an aromatic ring optionally having substituent(s),
$Y^A$ represents —$CHR^{10aA}$—$CHR^{10bA}$— (wherein $R^{10aA}$ and $R^{10bA}$ are the same or different and each represents a hydrogen atom, hydroxy, lower alkyl optionally having substituent(s) or lower alkoxy optionally having substituent(s)), —$CR^{10cA}$=$CR^{10dA}$— (wherein $R^{10cA}$ and $R^{10dA}$ are the same or different and each represents a hydrogen atom or lower alkyl optionally having substituent(s)), —$Z^{aA}$—$CR^{11aA}R^{11bA}$— [wherein $R^{11aA}$ and $R^{11bA}$ are the same or different and each represents a hydrogen atom or lower alkyl optionally having substituent(s), or $R^{11aA}$ and $R^{11bA}$ form carbonyl together with the adjacent carbon atom, $Z^{aA}$ represents C(=O), O, S, SO, $SO_2$ or $NR^{12A}$ (wherein $R^{12A}$ represents a hydrogen atom, lower alkyl optionally having substituent(s), lower alkanoyl optionally having substituent(s), lower alkoxycarbonyl optionally having substituent(s) or aralkyl optionally having substituent(s))], or —$CR^{11cA}R^{11dA}$—$Z^{bA}$— (wherein $R^{11cA}$, $R^{11dA}$ and $Z^{bA}$ are as defined for the aforementioned $R^{11aA}$, $R^{11bA}$ and $Z^{aA}$, respectively)}, or

(wherein $R^{zA}$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s), $R^{5bA}$ and $R^{7bA}$ are the same or different and each represents halogen, hydroxy, lower alkyl optionally having substituent(s) or lower alkoxy optionally having substituent(s), nbA represents an integer of 0-2, ncA represents an integer of 0-2, when nbA is 2, respective $R^{5bA}$ are the same or different and when ncA is 2, respective $R^{7bA}$ are the same or different), $R^{13A}$ represents a hydrogen atom, lower alkyl optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), or $R^{13A}$ and $R^{13B}$ form, together with the adjacent nitrogen atom, a nitrogen-containing heterocyclic group optionally having substituent(s), $R^{13B}$ represents a hydrogen atom, lower alkyl optionally having substituent(s), lower alkoxy optionally having substituent(s), cycloalkyl optionally having substituent(s), aralkyl optionally having substituent(s), aryl optionally having substituent(s), an aromatic heterocyclic group optionally having substituent(s), an aliphatic heterocyclic group optionally having substituent(s) or $COR^{13e1}$ (wherein $R^{13e1}$ is as defined for the aforementioned $R^{13e}$), or $R^{13B}$ and $R^{13A}$ form, together with the adjacent nitrogen atom, a nitrogen-containing heterocyclic group optionally having substituent(s), and
$R^{4A}$ represents a hydrogen atom or lower alkyl optionally having substituent(s)},
or a pharmaceutically acceptable salt thereof.

(3) The pyrazolopyrimidine derivative or the pharmaceutically acceptable salt thereof according to the aforementioned (2), wherein $L^1$ is a single bond.

(4) The pyrazolopyrimidine derivative or the pharmaceutically acceptable salt thereof according to the aforementioned (2) or (3), wherein $R^{14}$ is aryl optionally having substituent(s).

(5) The pyrazolopyrimidine derivative or the pharmaceutically acceptable salt thereof according to the aforementioned (2) or (3), wherein $R^{14}$ is phenyl optionally having substituent(s).

(6) The pyrazolopyrimidine derivative or the pharmaceutically acceptable salt thereof according to the aforementioned (2) or (3), wherein $R^{14}$ is an aromatic heterocyclic group optionally having substituent(s).

(7) The pyrazolopyrimidine derivative or the pharmaceutically acceptable salt thereof according to any of the aforementioned (2)-(6), wherein $R^{44}$ is a hydrogen atom.

(8) The pyrazolopyrimidine derivative or the pharmaceutically acceptable salt thereof according to any of the aforementioned (2)-(7), wherein $R^{13A}$ is a hydrogen atom, and $R^{13B}$ is lower alkyl optionally having substituent(s).

(9) The pyrazolopyrimidine derivative or the pharmaceutically acceptable salt thereof according to any of the aforementioned (2)-(7), wherein $R^{13A}$ is a hydrogen atom, and $R^{13B}$ is $COR^{13e1}$ (wherein $R^{13e1}$ is as defined above).

(10) The pyrazolopyrimidine derivative or the pharmaceutically acceptable salt thereof according to any of the aforementioned (2)-(7), wherein $R^{13A}$ is a hydrogen atom, and $R^{13B}$ is $COR^{13e2}$ (wherein $R^{13e2}$ represents lower alkyl optionally having substituent(s), cycloalkyl optionally having substituent(s), N-mono-lower alkylamino optionally having substituent(s) or N-mono-arylamino optionally having substituent(s)).

(11) The pyrazolopyrimidine derivative or the pharmaceutically acceptable salt thereof according to any of the aforementioned (2)-(10), wherein $R^{zA}$ is

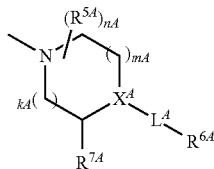

(wherein nA, mA, kA, $R^{5A}$, $R^{6A}$, $R^{7A}$, $L^A$ and $X^A$ are each as defined above).
(12) The pyrazolopyrimidine derivative or the pharmaceutically acceptable salt thereof according to the aforementioned (11), wherein $R^{6A}$ is phenyl optionally having substituent (s).
(13) The pyrazolopyrimidine derivative or the pharmaceutically acceptable salt thereof according to any of the aforementioned (2)-(10), wherein $R^{zA}$ is

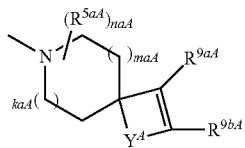

(wherein naA, maA, kaA, $R^{5aA}$, $R^{9aA}$, $R^{9bA}$ and $Y^A$ are each as defined above).
(14) The pyrazolopyrimidine derivative or the pharmaceutically acceptable salt thereof according to the aforementioned (13), wherein $R^{9aA}$ and $R^{9bA}$ form, together with the respectively adjacent carbon atom, a benzene ring optionally having substituent(s), $Y^A$ is —CHR$^{10aA}$—CHR$^{10bA}$— (wherein $R^{10aA}$ and $R^{10bA}$ are each as defined above), —CR$^{10cA}$=CR$^{10dA}$— (wherein $R^{10cA}$ and $R^{10dA}$ are each as defined above), —O—CR$^{11aA}$R$^{11bA}$— (wherein $R^{11aA}$ and $R^{11bA}$ are each as defined above) or —CR$^{11cA}$R$^{11dA}$—O— (wherein $R^{11cA}$ and $R^{11dA}$ are each as defined above).
(15) The pyrazolopyrimidine derivative or the pharmaceutically acceptable salt thereof according to any of the aforementioned (2)-(10), wherein $R^{zA}$ is

(wherein $R^{zA}$, $R^{5bA}$, $R^{7bA}$, nbA and ncA are each as defined above).
(16) The pyrazolopyrimidine derivative or the pharmaceutically acceptable salt thereof according to the aforementioned (15), wherein $R^{zA}$ is phenyl optionally having substituent(s).
(17) A medicament comprising, as an active ingredient, the pyrazolopyrimidine derivative or the pharmaceutically acceptable salt thereof according to any of the aforementioned (1)-(16).
(18) An agent for the prevention and/or treatment of a skin disease comprising, as an active ingredient, the pyrazolopyrimidine derivative or the pharmaceutically acceptable salt thereof according to any of the aforementioned (1)-(16).

(19) The agent for the prevention and/or treatment of a skin disease according to the aforementioned (18), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.
(20) The agent for the prevention and/or treatment of a skin disease according to the aforementioned (18), wherein the skin disease is dermatitis.
(21) The agent for the prevention and/or treatment of a skin disease according to the aforementioned (18), wherein the skin disease is a skin disease selected from contact dermatitis and atopic dermatitis.
(22) A method for the prevention and/or treatment of a skin disease, comprising a step of administering an effective amount of the pyrazolopyrimidine derivative or the pharmaceutically acceptable salt thereof according to any of the aforementioned (1)-(16) to a subject in need thereof.
(23) The method according to the aforementioned (22), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.
(24) The method according to the aforementioned (22), wherein the skin disease is dermatitis.
(25) The method according to the aforementioned (22), wherein the skin disease is a skin disease selected from contact dermatitis and atopic dermatitis.
(26) The pyrazolopyrimidine derivative or the pharmaceutically acceptable salt thereof according to any of the aforementioned (1)-(16) for use in prevention and/or treatment of a skin disease.
(27) The pyrazolopyrimidine derivative or the pharmaceutically acceptable salt thereof according to the aforementioned (26), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.
(28) The pyrazolopyrimidine derivative or the pharmaceutically acceptable salt thereof according to the aforementioned (26), wherein the skin disease is dermatitis.
(29) The pyrazolopyrimidine derivative or the pharmaceutically acceptable salt thereof according to the aforementioned (26), wherein the skin disease is a skin disease selected from contact dermatitis and atopic dermatitis.

(30) Use of the pyrazolopyrimidine derivative or the pharmaceutically acceptable salt thereof according to any of the aforementioned (1)-(16) for the manufacture of an agent for the prevention and/or treatment of a skin disease.

(31) The use according to the aforementioned (30), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(32) The use according to the aforementioned (30), wherein the skin disease is dermatitis.

(33) The use according to the aforementioned (30), wherein the skin disease is a skin disease selected from contact dermatitis and atopic dermatitis.

Effect of the Invention

The present invention provides a pyrazolopyrimidine derivative or a pharmaceutically acceptable salt thereof useful as an agent for the prevention and/or treatment of skin diseases, and the like.

MODE FOR CARRYING OUT THE INVENTION

In the present description, the compounds represented by the formula (I) and the formula (IA) are referred to as Compound (I) and Compound (IA), respectively. The same applies to the compounds having other formula numbers.

In the definition of each group in the formula (I) and the formula (IA),

Examples of the lower alkyl, and the lower alkyl moiety of the lower alkoxy, the lower alkoxycarbonyl, the lower alkanoyl, the N-mono-lower alkylamino and the N,N-di-lower alkylamino include straight chain or branched alkyl having 1-10 carbon atoms, more specifically, methyl, ethyl, propyl, isopropyl, butyl, isobutyl, sec-butyl, tert-butyl, pentyl, isopentyl, neopentyl, hexyl, heptyl, octyl, nonyl, decyl and the like. Two lower alkyl moieties of the N,N-di-lower alkylamino may be the same or different.

The alkylene has the same meaning as the group formed by removing one hydrogen atom from the aforementioned lower alkyl.

Examples of the cycloalkyl, and the cycloalkyl moiety of the N-cycloalkylamino include cycloalkyl having 3-8 carbon atoms, and more specific examples thereof include cyclopropyl, cyclobutyl, cyclopentyl, cyclohexyl, cycloheptyl, cyclooctyl and the like.

Examples of the aryl, and the aryl moiety of the N-monoarylamino and the N,N-diarylamino include aryl having 6-14 carbon atoms, and more specific examples thereof include phenyl, naphthyl, azulenyl, anthryl, pentalenyl, indenyl, biphenylenyl and the like.

The alkylene moiety of the aralkyl has the same meaning as the group formed by removing one hydrogen atom from the aforementioned lower alkyl, and the aryl moiety is as defined for the aforementioned aryl.

Examples of the aliphatic heterocyclic group include a 3- to 7-membered monocyclic aliphatic heterocyclic group containing at least one atom selected from a nitrogen atom, an oxygen atom and a sulfur atom, a bicyclic or tricyclic condensed aliphatic heterocyclic group containing at least one atom selected from a nitrogen atom, an oxygen atom and a sulfur atom, wherein 3- to 8-membered rings are condensed, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, oxetanyl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic condensed aromatic heterocyclic group containing at least one atom selected from a nitrogen atom, an oxygen atom and a sulfur atom, wherein 3- to 8-membered rings are condensed, and the like, and more specific examples thereof include furyl, thienyl, pyrrolyl, imidazolyl, pyrazolyl, oxazolyl, isoxazolyl, oxadiazolyl, triazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, azepinyl, diazepinyl, pyranyl, oxepinyl, thiopyranyl, thiepinyl, furazanyl, oxadiazolyl, oxazinyl, oxadiazinyl, oxazepinyl, oxadiazepinyl, thiazinyl, thiadiazinyl, thiazepinyl, thiadiazepinyl, indolizinyl, isobenzofuranyl, isobenzothiophenyl, dithianaphthalenyl, quinolizinyl, pteridinyl, benzoxazolidinyl, chromenyl, benzoxepinyl, benzoxadiazepinyl, benzothiepinyl, benzothiazepinyl, benzothiadiazepinyl, benzothiepinyl, benzothiazepinyl, benzoazepinyl, benzodiazepinyl, benzofurazanyl, benzothiadiazolinyl, carbazolyl, β-carbolinyl, acrydinyl, phenazinyl, dibenzofuranyl, xanthenyl, dibenzothiophenyl, phenothiazinyl, phenoxazinyl, phenoxathinyl, thianthrenyl, phenanthridinyl, phenanthrolinyl, perimidinyl and the like.

Examples of the nitrogen-containing heterocyclic group formed together with the adjacent nitrogen atom thereto include a 5-membered or 6-membered monocyclic heterocyclic group containing at least one nitrogen atom (said monocyclic heterocyclic group may contain any other of a nitrogen atom, an oxygen atom or a sulfur atom), a bicyclic or tricyclic condensed heterocyclic group containing at least one nitrogen atom (said condensed heterocyclic group may contain any other of a nitrogen atom, an oxygen atom or a sulfur atom), wherein 3- to 8-membered rings are condensed, and the like, and more specific examples thereof include aziridinyl, azetidinyl, pyrrolidinyl, piperidino, azepanyl, pyrrolinyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl and the like.

Examples of the aliphatic ring include aliphatic rings corresponding to the aforementioned cycloalkyl and aliphatic heterocyclic group.

Examples of the aliphatic ring having at least one double bond include aliphatic rings having one or more double bond from among the aforementioned aliphatic ring, and more specific examples thereof include 1,2,5,6-tetrahydropyridine, tetrahydro-2H-pyran, 2H-oxazoline, 2H-thioxazoline, dihydroindoline, dihydroisoindoline, dihydrobenzofuran, dihydrobenzooxazoline, dihydrobenzothioxazoline, dihydro-2Hchromane, dihydro-1H-chromane, dihydro-2H-thiochromane, dihydro-1H-thiochromane, dihydrobenzodioxane and the like.

Examples of the aromatic ring include aromatic rings corresponding to the aforementioned aryl and aromatic heterocyclic group.

The halogen means each atom of fluorine, chlorine, bromine or iodine.

The substituent(s) (substituent group-1) in the lower alkyl optionally having substituent(s), the lower alkoxy optionally having substituent(s), the N-mono-lower alkylamino optionally having substituent(s), the N,N-di-lower alkylamino optionally having substituent(s), the lower alkoxycarbonyl optionally having substituent(s) and the lower alkanoyl optionally having substituent(s) are the same or different and examples thereof include 1 to 3 substituents selected from the group consisting of halogen; sulfanyl; nitro; cyano; $C_{3-8}$ cycloalkyl optionally having 1 to 3 substituents selected from the following substituent group C; an aliphatic heterocyclic group optionally having 1 to 3 substituents selected from the following substituent group C; an aromatic heterocyclic group optionally having 1 to 3 substituents selected from the following substituent group B; $C_{1-10}$ alkylsulfanyl optionally having 1 to 3 substituents selected from the following substituent group A; $C_{6-14}$ arylsulfanyl optionally having 1 to 3 substituents selected from the following substituent group B; $C_{1-10}$ alkylsulfonyl optionally having 1 to 3 substituents selected from the following substituent group A; $C_{6-14}$ arylsulfonyl optionally having 1 to 3 substituents selected from the following substituent group B; $OR^{16}$ (wherein $R^{16}$ represents a hydrogen atom, $C_{1-10}$ alkyl optionally having 1 to 3 substituents selected from the following substituent group A, $C_{3-8}$ cycloalkyl optionally having 1 to 3 substituents selected from the following substituent group C, $C_{6-14}$ aryl optionally having 1 to 3 substituents selected from the following substituent group B, $C_{7-16}$ aralkyl optionally having 1 to 3 substituents selected from the following substituent group B, an aromatic heterocyclic group optionally having 1 to 3 substituents selected from the following substituent group B, $C_{2-11}$ alkanoyl optionally having 1 to 3 substituents selected from the following substituent group A, $C_{7-15}$ aroyl having 1 to 3 substituents selected from the following substituent group B, $C_{1-10}$ alkylsulfonyl optionally having 1 to 3 substituents selected from the following substituent group A or $C_{6-14}$ arylsulfonyl optionally having 1 to 3 substituents selected from the following substituent group B); $C(=O)R^{17a}$ (wherein $R^{17a}$ represents amino, hydroxy, $C_{1-10}$ alkyl optionally having 1 to 3 substituents selected from the following substituent group A, $C_{3-8}$ cycloalkyl optionally having 1 to 3 substituents selected from the following substituent group C, $C_{6-14}$ aryl optionally having 1 to 3 substituents selected from the following substituent group B, an aliphatic heterocyclic group optionally having 1 to 3 substituents selected from the following substituent group C, an aromatic heterocyclic group optionally having 1 to 3 substituents selected from the following substituent group B, $C_{1-10}$ alkoxy optionally having 1 to 3 substituents selected from the following substituent group A, $C_{6-14}$ aryloxy optionally having 1 to 3 substituents selected from the following substituent group B, $C_{1-10}$ alkylamino optionally having 1 to 3 substituents selected from the following substituent group A, di-$C_{1-10}$ alkylamino optionally having 1 to 3 substituents selected from the following substituent group A or $C_{6-14}$ arylamino optionally having 1 to 3 substituents selected from the following substituent group B); and —$NR^{18a}R^{18b}$ (wherein $R^{18a}$ and $R^{18b}$ are the same or different and each represents a hydrogen atom, formyl, $C_{1-10}$ alkyl optionally having 1 to 3 substituents selected from the following substituent group A, $C_{3-8}$ cycloalkyl optionally having 1 to 3 substituents selected from the following substituent group C, $C_{6-14}$ aryl optionally having 1 to 3 substituents selected from the following substituent group B, an aliphatic heterocyclic group optionally having 1 to 3 substituents selected from the following substituent group C, an aromatic heterocyclic group optionally having 1 to 3 substituents selected from the following substituent group B, $C_{2-11}$ alkanoyl optionally having 1 to 3 substituents selected from the following substituent group A, $C_{7-15}$ aroyl optionally having 1 to 3 substituents selected from the following substituent group B, $C_{1-10}$ alkoxycarbonyl optionally having 1 to 3 substituents selected from the following substituent group A, $C_{1-10}$ alkylsulfonyl optionally having 1 to 3 substituents selected from the following substituent group A or $C_{6-14}$ arylsulfonyl optionally having 1 to 3 substituents selected from the following substituent group B). Examples of the substituent in the lower alkoxy optionally having substituent(s), the lower alkoxycarbonyl optionally having substituent(s) and the lower alkanoyl optionally having substituent(s) also include $C_{6-14}$ aryl optionally having 1 to 3 substituents selected from the following substituent group B, in addition to the aforementioned substituent group-1.

The substituent(s) in the aryl optionally having substituent(s), the N-mono-arylamino optionally having substituent(s), the N,N-diarylamino optionally having substituent(s), the phenyl optionally having substituent(s), the aralkyl optionally having substituent(s), the aromatic heterocyclic group optionally having substituent(s), the aromatic ring optionally having substituent(s) and the benzene ring optionally having substituent(s) are the same or different and examples thereof include 1 to 3 substituents selected from the group consisting of $C_{1-10}$ alkyl optionally having 1 to 3 substituents selected from the following substituent group A, $C_{6-14}$ aryl optionally having 1 to 3 substituents selected from the following substituent group B and the substituents of the aforementioned substituent group-1. The substituent in the aryl optionally having substituent(s) include $C_{4-8}$ cycloalkyl ring condensing with the aryl moiety of the substituted aryl and optionally having 1 to 3 substituents selected from the following substituent group C, or aliphatic heterocyclic ring condensing with the aryl moiety of the substituted aryl and optionally having 1 to 3 substituents selected from the following substituent group C, in addition to the above substituent(s). The substituent in the phenyl optionally having substituent(s) include $C_{4-8}$ cycloalkyl ring condensing with the phenyl moiety of the substituted phenyl and optionally having 1 to 3 substituents selected from the following substituent group C, or aliphatic heterocyclic ring condensing with the phenyl moiety of the substituted phenyl and optionally having 1 to 3 substituents selected from the following substituent group C, in addition to the above substituent(s). The substituent in the aryl moiety of the aralkyl optionally having substituent(s) include $C_{4-8}$ cycloalkyl ring condensing with the aryl moiety of the substituted aralkyl and optionally having 1 to 3 substituents selected from the following substituent group C, or aliphatic heterocycle ring condensing with the aryl moiety of the substituted aralkyl and optionally having 1 to 3 substituents selected from the following substituent group C, in addition to the above substituent(s).

The substituent(s) in the cycloalkyl optionally having substituent(s), the N-cyclialkylamino optionally having substituent(s), the aliphatic heterocyclic group optionally having substituent(s), the aliphatic ring having at least one double bond optionally having substituent(s), the nitrogen-containing heterocyclic group optionally having substituent(s), which is formed together with the adjacent nitrogen atom, and the aliphatic ring optionally having substituent(s) are the same or different and examples thereof include 1 to 3 substituents selected from the group consisting of oxo, $C_{1-10}$ alkyl optionally having 1 to 3 substituents selected from the following substituent group A, $C_{6-14}$ aryl optionally having 1 to 3 substituents selected from the following substituent group B and the substituents of the aforementioned substituent group-1. The substituent in the cycloalkyl optionally having substituent(s) include benzene ring condensing with the cycloalkyl moiety of the substituted cycloalkyl and optionally having 1 to 3 substituents selected from the following substituent group B, in addition to the above substituent(s).

The substituent group A means the group consisting of halogen; hydroxy; sulfanyl; nitro; cyano; carboxy; carbamoyl; $C_{3-8}$ cycloalkyl; $C_{6-14}$ aryl optionally having 1 to 3 substituents selected from the group consisting of halogen, hydroxy, amino, nitro, carboxy, $C_{1-10}$ alkoxycarbonyl, $C_{1-10}$ alkoxy and trifluoromethyl (substituent group a); an aliphatic heterocyclic group; an aromatic heterocyclic group; $C_{1-10}$ alkoxy optionally having 1 to 3 substituents selected from the group consisting of halogen, hydroxy, amino, carboxy, $C_{1-10}$ alkoxy, $C_{1-10}$ alkylamino, di-$C_{1-10}$ alkylamino and $C_{1-10}$ alkoxycarbonyl (substituent group b); $C_{3-8}$ cycloalkoxy; $C_{6-14}$ aryloxy optionally having 1 to 3 substituents selected from the aforementioned substituent group a; $C_{7-16}$ aralkyloxy optionally having 1 to 3 substituents selected from the aforementioned substituent group a; $C_{2-11}$ alkanoyloxy; $C_{7-15}$ aroyloxy; $C_{1-10}$ alkylsulfonyloxy; trifluoromethanesulfonyloxy; $C_{6-14}$ arylsulfonyloxy; p-toluenesulfonyloxy; $C_{1-10}$ alkylsulfanyl; $C_{6-14}$ arylsulfanyl; —$NR^{19a}R^{19b}$ (wherein $R^{19a}$ and $R^{19b}$ are the same or different and each represents a hydrogen atom; formyl; $C_{1-10}$ alkyl optionally having 1 to 3 substituents selected from the aforementioned substituent group b; $C_{3-8}$ cycloalkyl; $C_{6-14}$ aryl optionally having 1 to 3 substituents selected from the aforementioned substituent group a; an aromatic heterocyclic group; $C_{7-16}$ aralkyl optionally having 1 to 3 substituents selected from the aforementioned substituent group a; $C_{2-11}$ alkanoyl; $C_{7-15}$ aroyl; $C_{1-10}$ alkoxycarbonyl; $C_{7-16}$ aralkyloxycarbonyl; $C_{1-10}$ alkylsulfonyl; trifluoromethanesulfonyl; $C_{6-14}$ arylsulfonyl or p-toluenesulfonyl); $C_{2-11}$ alkanoyl; $C_{3-8}$ cycloalkylcarbonyl; $C_{7-15}$ aroyl; aliphatic heterocyclylcarbonyl; aromatic heterocyclylcarbonyl; $C_{1-10}$ alkoxycarbonyl; $C_{6-14}$ aryloxycarbonyl; $C_{7-16}$ aralkyloxycarbonyl; $C_{1-10}$ alkylcarbamoyl; di-$C_{1-10}$ alkylcarbamoyl and $C_{6-14}$ arylcarbamoyl.

The substituent group B means the group consisting of $C_{1-10}$ alkyl, trifluoromethyl and the substituents of the aforementioned substituent group A.

The substituent group C means the group consisting of oxo, $C_{1-10}$ alkyl, trifluoromethyl and the substituents of the aforementioned substituent group A.

Examples of the $C_{1-10}$ alkyl and the $C_{1-10}$ alkyl moiety of the $C_{1-10}$ alkoxy, the $C_{2-11}$ alkanoyloxy, the $C_{1-10}$ alkylsulfanyl, the $C_{2-11}$ alkanoyl, the $C_{1-10}$ alkoxycarbonyl, the $C_{1-10}$ alkylcarbamoyl, the di-$C_{1-10}$ alkylcarbamoyl, the $C_{1-10}$ alkylsulfonyl, the $C_{1-10}$ alkylsulfonyloxy, the $C_{1-10}$ alkylamino and the di-$C_{1-10}$ alkylamino shown here include the groups exemplified as the aforementioned lower alkyl. Two $C_{1-10}$ alkyl moieties of di-$C_{1-10}$ alkylcarbamoyl and di-$C_{1-10}$ alkylamino may be the same or different.

Examples of the $C_{3-8}$ cycloalkyl and the $C_{3-8}$ cycloalkyl moiety of the $C_{3-8}$ cycloalkoxy and the $C_{3-8}$ cycloalkylcarbonyl include the groups exemplified as the aforementioned cycloalkyl.

Examples of the aryl condensed with the $C_{4-8}$ cycloalkyl ring and the moiety formed by removing the alkylene moiety from the aralkyl of which aryl moiety is condensed with the $C_{4-8}$ cycloalkyl ring include a cycloalkyl-condensed aryl having 8 to 16 carbon atoms, and more specific examples thereof include indanyl, 1,2,3,4-tetrahydronaphthalenyl and the like.

Examples of the phenyl condensed with the $C_{4-8}$ cycloalkyl ring include a cycloalkyl-condensed phenyl having 8 to 12 carbon atoms, and more specific examples thereof include indanyl, 1,2,3,4-tetrahydronaphthalenyl and the like.

Examples of the cycloalkyl condensed with the benzene ring include a benzene ring-condensed cycloalkyl having 8 to 12 carbon atoms, and more specific examples thereof include indanyl, 1,2,3,4-tetrahydronaphthalenyl and the like.

Examples of the $C_{6-14}$ aryl, and the aryl moiety of the $C_{6-14}$ aryloxy, the $C_{6-14}$ acylamino, the $C_{6-14}$ arylsulfanyl, the $C_{7-15}$ aroyl, the $C_{7-15}$ aroyloxy, the $C_{6-14}$ aryloxycarbonyl, the $C_{6-14}$ arylsulfonyl, the $C_{6-14}$ arylsulfonyloxy and the $C_{6-14}$ arylcarbamoyl include the groups exemplified as the aforementioned aryl.

Examples of the aryl moiety of the $C_{7-16}$ aralkyloxy, the $C_{7-16}$ aralkyl and the $C_{7-16}$ aralkyloxycarbonyl include the group exemplified as the aforementioned aryl, and examples of the alkylene moiety thereof include $C_{1-10}$ alkylene and more specific examples thereof include the group formed by removing one hydrogen atom from the aforementioned lower alkyl and the like.

Examples of the aliphatic heterocyclic group and the aliphatic heterocyclic group moiety of the aliphatic heterocyclylcarbonyl include the groups exemplified as the aforementioned aliphatic heterocyclic group.

Examples of the aromatic heterocyclic group and the aromatic heterocyclic group moiety of the aromatic heterocyclylcarbonyl include the groups exemplified as the aforementioned aromatic heterocyclic group.

Examples of the aryl condensed with the aliphatic heterocycle and the moiety formed by removing the alkylene moiety from the aralkyl of which aryl moiety is condensed with the aliphatic heterocycle include aryl condensed with a 4- to 7-membered monocyclic aliphatic heterocyclic group containing at least one atom selected from a nitrogen atom, an oxygen atom and a sulfur atom, and more specific examples thereof include dihydrobenzofuranyl, dihydroisobenzofuranyl, indolinyl, isoindolinyl, chromanyl, isochromanyl and the like.

Examples of the phenyl condensed with the aliphatic heterocycle include phenyl condensed with a 4- to 7-membered monocyclic aliphatic heterocyclic group containing at least one atom selected from a nitrogen atom, an oxygen atom and a sulfur atom, and more specific examples thereof include dihydrobenzofuranyl, dihydroisobenzofuranyl, indolinyl, isoindolinyl, chromanyl, isochromanyl and the like.

Examples of the halogen include the atom exemplified as the aforementioned halogen.

In each group of Compound (I), $R^1$ is preferably $NR^{1a}R^{1b}$ (wherein $R^{1a}$ and $R^{1b}$ are each as defined above), more preferably, one of $R^{1a}$ and $R^{1b}$ is a hydrogen atom, and the other is lower alkyl optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), and more preferably, one of $R^{1a}$ and $R^{1b}$ is a hydrogen atom, and the other is aralkyl optionally having substituent(s) or aryl optionally having substituent(s) (wherein the substituent(s) in the aralkyl optionally having substituent(s) or the aryl optionally having substituent(s) is preferably lower alkyl or halogen, and the number of substituents(s) is preferably 2 or 3). In addition, it is also more preferable that one of $R^{1a}$ and $R^{1b}$ is a hydrogen atom, and the other is an aromatic heterocyclic group optionally having substituent(s).

When $R^2$ is

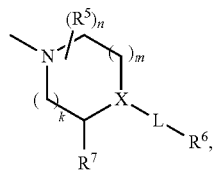

$R^5$ is preferably lower alkyl optionally having substituent(s), more preferably lower alkyl, $R^6$ is preferably aryl optionally having substituent(s) or an aromatic heterocyclic group optionally having substituent(s), more preferably aryl optionally having substituent(s), still more preferably phenyl optionally having substituent(s), $R^7$ is preferably a hydrogen atom or lower alkyl, X is preferably a nitrogen atom or $CR^{8a}$ (wherein $R^{8a}$ represents a hydrogen atom, halogen or lower alkyl), more preferably $CR^{8a}$ (wherein $R^{8a}$ is as defined above), L is preferably a single bond, k and m are each preferably 1, and n is preferably 0 or 1, more preferably 0.

When $R^2$ is

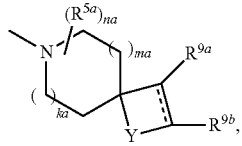

$R^{5a}$ is preferably lower alkyl optionally having substituent(s), more preferably lower alkyl.

$R^{9a}$ and $R^{9b}$ preferably form, together with the respectively adjacent carbon atom, an aromatic ring optionally having substituent(s), more preferably form, together with the respectively adjacent carbon atom, a benzene ring optionally having substituent(s), Y is preferably —$CHR^{10a}$—$CHR^{10b}$— (wherein $R^{10a}$ and $R^{10b}$ are each as defined above), —$CR^{10c}$=$CR^{10d}$— (wherein $R^{10c}$ and $R^{10d}$ are each as defined above), —O—$CR^{11a}R^{11b}$— (wherein $R^{11a}$ and $R^{11b}$ are each as defined above) or —$CR^{11c}R^{11d}$—O— (wherein $R^{11c}$ and $R^{11d}$ are each as defined above), more preferably —$CHR^{10aa}$—$CHR^{10ba}$— (wherein $R^{10aa}$ and $R^{10ba}$ are the same or different and each represents a hydrogen atom or lower alkyl), —$CR^{10ca}$=$CR^{10da}$— (wherein $R^{10ca}$ and $R^{10da}$ are the same or different and each represents a hydrogen atom or lower alkyl), —O—$CR^{11aa}R^{11ba}$— (wherein $R^{11aa}$ and $R^{11ba}$ are the same or different and each represents a hydrogen atom or lower alkyl), or —$CR^{11ca}R^{11da}$—O— (wherein $R^{11ca}$ and $R^{11da}$ are the same or different and each represents a hydrogen atom or lower alkyl), ka and ma are each preferably 1, and na is preferably 0 or 1, more preferably 0.

When $R^2$ is

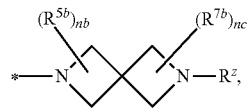

$R^z$ is preferably aryl optionally having substituent(s) or an aromatic heterocyclic group optionally having substituent(s), more preferably aryl optionally having substituent(s), still more preferably phenyl optionally having substituent(s), $R^{5b}$ and $R^{7b}$ are the same or different and each is preferably halogen, hydroxy or lower alkyl optionally having substituent(s), more preferably halogen or lower alkyl optionally having substituent(s), still more preferably lower alkyl optionally having substituent(s), and nb is preferably 0 and nc is preferably 0.

$R^3$ is preferably the following (A) or (B).

(A) $S(O)_2NR^{13b}R^{13c}$ (wherein $R^{13b}$ and $R^{13c}$ are each as defined above), and it is more preferably when $R^{13b}$ is a hydrogen atom and $R^{13c}$ is lower alkyl optionally having substituent(s), lower alkoxy optionally having substituent(s) or cycloalkyl optionally having substituent(s).

(B) $S(O)_2NR^{13d}C(=O)R^{13e}$ (wherein $R^{13d}$ and $R^{13e}$ are each as defined above), and it is more preferably when $R^{13d}$ is a hydrogen atom and $R^{13e}$ is lower alkyl optionally having substituent(s), cycloalkyl optionally having substituent(s), lower alkoxy optionally having substituent(s), N-monolower alkylamino optionally having substituent(s), N,N-dilower alkylamino optionally having substituent(s), N-cycloalkylamino optionally having substituent(s), N-monoarylamino optionally having substituent(s) or N,N-diarylamino optionally having substituent(s).

$R^4$ is preferably a hydrogen atom.

As Compound (I), a compound, wherein two or more of the above-mentioned preferable substituent embodiments are combined, is preferable.

In each group of Compound (IA), $R^{14}$ is preferably aryl optionally having substituent(s) or an aromatic heterocyclic group optionally having substituent(s), more preferably aryl optionally having substituent(s), still more preferably phenyl optionally having substituent(s) (wherein the substituent(s) in the aryl optionally having substituent(s) or the phenyl optionally having substituent(s) is preferably lower alkyl or halogen, and the number of substituents(s) is preferably 2 or 3). And it is also more preferable embodiment when $R^{14}$ is an aromatic heterocyclic group optionally having substituent(s).

$L^1$ is preferably a single bond.

When $R^{2A}$ is

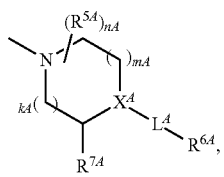

$R^{5A}$ is preferably lower alkyl,
$R^{6A}$ is preferably aryl optionally having substituent(s) or an aromatic heterocyclic group optionally having substituent(s), more preferably aryl optionally having substituent(s), still more preferably phenyl optionally having substituent(s),
$L^A$ is preferably a single bond,
$R^{7A}$ is preferably a hydrogen atom or lower alkyl,
$X^A$ is preferably a nitrogen atom or —$CR^{8Aa}$ (wherein $R^{8Aa}$ represents a hydrogen atom, halogen or lower alkyl), more preferably —$CR^{8Aa}$ (wherein $R^{8Aa}$ is as defined above),
mA and kA are each preferably 1, and
nA is preferably 0 or 1, more preferably 0.
When $R^{2A}$ is

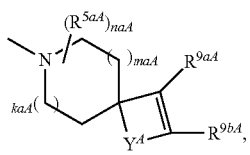

$R^{5aA}$ is preferably lower alkyl,
kaA and maA are each preferably 1,
$R^{9aA}$ and $R^{9bA}$ preferably form, each together with the adjacent carbon atom, a benzene ring optionally having substituent(s),
$Y^A$ is preferably —$CHR^{10aA}$—$CHR^{10bA}$— (wherein $R^{10aA}$ and $R^{10bA}$ are each as defined above), —$CR^{10cA}$=$CR^{10dA}$— (wherein $R^{10cA}$ and $R^{10dA}$ are each as defined above), —O—$CR^{11aA}R^{11bA}$— (wherein $R^{11aA}$ and $R^{11bA}$ are each as defined above) or —$CR^{11cA}R^{11dA}$—O— (wherein $R^{11cA}$ and $R^{11dA}$ are each as defined above), more preferably —$CHR^{10aAa}$—$CHR^{10bAa}$— (wherein $R^{10aAa}$ and $R^{10bAa}$ are the same or different and each represents a hydrogen atom or lower alkyl), —$CR^{10cAa}$=$CR^{10dAa}$— (wherein $R^{10cAa}$ and $R^{10dAa}$ are the same or different and each represents a hydrogen atom or lower alkyl), —O—$CR^{11aAa}R^{11bAa}$— (wherein $R^{11aAa}$ and $R^{11bAa}$ are the same or different and each represents a hydrogen atom or lower alkyl) or —$CR^{11cAa}R^{11dAa}$—O— (wherein $R^{11cAa}$ and $R^{11dAa}$ are the same or different and each represents a hydrogen atom or lower alkyl), and
naA is preferably 0 or 1, more preferably 0.
When $R^2$ is

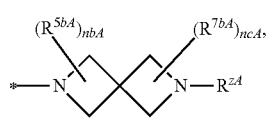

$R^{zA}$ is preferably aryl optionally having substituent(s) or an aromatic heterocyclic group optionally having substituent(s), more preferably aryl optionally having substituent(s), still more preferably phenyl optionally having substituent(s), $R^{5bA}$ and $R^{7bA}$ are the same or different and each is preferably halogen, hydroxy or lower alkyl optionally having substituent(s), more preferably halogen or lower alkyl optionally having substituent(s), still more preferably lower alkyl optionally having substituent(s), and
nbA is preferably 0 and ncA is preferably 0.
$R^{13A}$ is preferably a hydrogen atom or lower alkyl optionally having substituent(s), more preferably a hydrogen atom.
$R^{13B}$ is preferably lower alkyl optionally having substituent(s), lower alkoxy optionally having substituent(s) or $COR^{13e1}$ (wherein $R^{13e1}$ is as defined above), more preferably lower alkyl, halogen-substituted lower alkyl (wherein the halogen moiety of the halogen-substituted lower alkyl is as defined for the aforementioned halogen and the lower alkyl moiety is as defined for the aforementioned alkylene) or $COR^{13e2}$ (wherein $R^{13e2}$ is as defined above).
$R^{4A}$ is preferably a hydrogen atom.

As Compound (IA), a compound, wherein two or more of the above-mentioned preferable substituent embodiments are combined, is preferable. In addition, Compound (IA) described in (3)-(16) of [Means of Solving the Problems] of which substituents are limited according to the above-mentioned preferable embodiments of the substituents, are preferable. Furthermore, Compound (IA) described in (3)-(16) of [Means of Solving the Problems] of which substituents are limited according to combinations of two or more above-mentioned preferable embodiments of the substituents, are more preferable.

The pharmaceutically acceptable salts of Compound (I) and (IA) comprise, for example, pharmaceutically acceptable acid addition salts, metal salts, ammonium salts, organic amine addition salts, amino acid addition salts and the like. Examples of the pharmaceutically acceptable acid addition salts of Compounds (I) and (IA) include, but are not limited to, inorganic acid salts such as hydrochloride, hydrobromide, nitrate, sulfate, phosphate and the like, organic acid salts such as acetate, oxalate, maleate, fumarate, citrate, benzoate, methanesulfonate and the like. Examples of the pharmaceutically acceptable metal salts include, but are not limited to, sodium salt, potassium salt, magnesium salt, calcium salt, aluminum salt, zinc salt and the like. Examples of the pharmaceutically acceptable ammonium salt include, but are not limited to, ammonium salt, tetramethylammonium salt and the like. Examples of the pharmaceutically acceptable organic amine addition salt include, but are not limited to, addition salts of morpholine, piperidine and the like. Examples of the pharmaceutically acceptable amino acid addition salt include, but are not limited to, addition salts of lysine, glycine, phenylalanine, aspartic acid, glutamic acid and the like.

The pharmaceutically acceptable salts of Compounds (I) and (IA) include quaternary ammonium salt. The quaternary ammonium salt means one wherein the nitrogen atom in the compound is quaternarized by Rx (Rx is lower alkyl or lower alkyl substituted phenyl where lower alkyl is as defined above).

The pharmaceutically acceptable salts of Compounds (I) and (IA) also include N-oxide. N-oxide is a compound wherein the nitrogen atom in the compound is oxidized. Using the Compounds (I) and (IA) which is not N-oxide, and in the any oxidation method, for example, by using m-chloroperbenzoic acid, air oxidization, an oxidation reagent such as liver extract and the like, the N-oxide of Compounds (I) and (IA) can be obtained.

In the present invention, the skin diseases refer to those where the lesion appears on the skin. Specific examples thereof include, but are not limited to, acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis and the like.

In the present invention, dermatitis refers to, from among the aforementioned skin diseases, one wherein immune system is endogenously or exogenously activated to cause skin symptoms. Specific examples thereof include, but are not limited to, acne vulgaris, contact dermatitis, atopic dermatitis, pollen dermatitis, psoriasis, drug eruption, lupus erythematosus, seborrheic dermatitis, eczema, Stevens-Johnson syndrome, toxic epidermal necrosis and the like.

The treatment in the present invention refers to reversing the progression of, mitigating or inhibiting the disease or condition to be applied, or one or more symptoms of such disease or condition. Moreover, it includes application to inhibit progression before remission of disease, or when the symptom is mild. In skin diseases, aggravation and remission may be repeated regularly or chronically. The agent for prevention and/or treatment are/is also used for extending the remission period and preventing aggravation. The agent for prevention is also used for preventing the onset of a disease.

The aggravation used in the present description refers to aggravation of the symptoms of a disease.

The remission used in the present description refers to a temporary or permanent reduction or disappearance of the symptoms of a disease.

The present invention also includes a prodrug of Compounds (I) and (IA). The prodrug of Compounds (I) and (IA) are a compound that can be converted to Compound (I) or (IA) by a reaction by an enzyme, gastric acid and the like in the body. As the prodrug, many kinds are known, and a suitable prodrug may be selected from a known literature (for example, Iyakuhin no Kaihatsu, Hirokawa Shoten, 1990, vol. 7, p. 163) and synthesized by a known method. For example, as a prodrug of Compounds (I) and (IA), when Compounds (I) and (IA) have amino, a compound wherein the amino is acylated, alkylated or phosphorylated, when Compounds (I) and (IA) have hydroxy, a compound wherein the hydroxy is acylated, alkylated, phosphorylated or borated, when Compounds (I) and (IA) have carboxy, a compound wherein the carboxy is esterified or amidated, and the like can be mentioned. The prodrug of Compounds (I) and (IA) may be any of hydrate, non-hydrate and solvate, and may form a salt with a pharmaceutically acceptable acid or base, like in the case of Compounds (I) and (IA).

A preferable compound used in the present description is a compound having desirable properties in one or more items from various evaluation items required for an agent for the prevention and/or treatment of skin diseases, pharmaceutical products or object of use, such as pharmacological activity, as well as physical stability, stability under physiological conditions, safety to the body and the like.

Compounds (I) and (IA) of the present invention, and pharmaceutically acceptable salts thereof may show an unpreferable action on living organisms. Even in such a case, the usefulness of an agent for the prevention and/or treatment, and a pharmaceutical product of the present invention can be exhibited while reducing an unpreferable action by using appropriate dose and administration method.

The Compounds (I) and (IA) of the present invention include those possibly having a stereoisomer such as geometric isomer, optical isomer and the like, tautomer and the like. The present invention encompasses all possible isomers and mixtures thereof including them, and the mixing ratio thereof may be any.

The Compounds (I) and (IA) of the present invention, and pharmaceutically acceptable salts thereof may be present as adducts with water or various solvents, and the present invention also encompasses such adducts.

A part or all of the respective atoms in Compound (I) and Compound (IA) may be substituted by respective, corresponding isotope atom(s), and the present invention also encompasses such compounds substituted by isotope atoms. For example, a part or all of hydrogen atoms in Compound (I) may be a hydrogen atom having an atomic weight of 2 (deuterium atom). A compound incorporating a radioisotope such as $^3$H (tritium) or $^{14}$C from among the isotopes is useful for examining the tissue distribution of a compound and screening for an agent for the prevention and/or treatment of skin diseases.

For example, a compound wherein a part or all of the respective atoms in Compound (I) is/are substituted by respective, corresponding isotope atom(s) can be produced using a commercially available building block and in the same manner as in each of the above-mentioned production methods. In addition, the compound wherein a part or all of the hydrogen atoms in Compound (I) is/are substituted by deuterium atom(s) can be synthesized by, for example, 1) a method using deuterium peroxide, to deuterate carboxylic acid and the like under basic conditions (see U.S. Pat. No. 3,849,458), 2) a method using an iridium complex as a catalyst, to deuterate alcohol, carboxylic acid and the like by using deuterium oxide as a deuterium source [see Journal of the American Chemical Society (J. Am. Chem. Soc.), Vol. 124, No. 10, 2092 (2002)], 3) a method using palladium carbon as a catalyst, to deuterate fatty acid by using only a deuterium gas as a deuterium source [see LIPIDS, Vol. 9, No. 11, 913 (1974)], 4) a method using metals such as platinum, palladium, rhodium, ruthenium, iridium and the like as catalysts, to deuterate acrylic acid, methyl acrylate, methacrylic acid, methyl methacrylate and the like by using deuterium oxide, or deuterium oxide and deuterium gas, as a deuterium source (see JP-B-5-19536, JP-A-61-277648 and JP-A-61-275241), 5) a method using a catalyst such as palladium, nickel, copper or chromite copper and the like, to deuterate acrylic acid, methyl methacrylate and the like by using deuterium oxide as deuterium source (see JP-A-63-198638) and the like.

The isotope atom used in the present description refers to an atom having an atomic value or a mass number different from those generally found naturally. Examples of the isotope in the compound of the present invention include $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, and the like.

The inert solvent used in the present description is an organic or inorganic solvent, which is liquid at room temperature or reaction temperature, and shows no change in the chemical structure after reaction. Specific examples thereof include, but are not limited to, tetrahydrofuran (THF), dioxane, carbon tetrachloride, acetone, ethyl acetate, methyl acetate, isopropyl acetate, diethyl ether, ethylene glycol, triethylene glycol, glyme, diglyme, 1,2-dimethoxyethane (DME), acetonitrile, methanol, ethanol, butanol, 2-propanol, methylene chloride, chloroform, benzene, water, toluene, pyridine, N,N-dimethylformamide (DMF), dimethylimidazole, N-methylpyrrolidine, N-methylpyrrolidinone, dimethylpropyleneurea, hexane, pentane, nitrobenzene, dimethyl sulfoxide(DMSO), diphenyl ether, Dowtherm A (registered trade mark), polychlorinated diphenyl, tetralin, heptane, octane, xylene, methylethylketone, methylisobutylketone, N,N-dimethylacetamide, sulfolane, 1,2-dichloroethane and the like.

The production methods of Compound (I) are explained in the following.

In the production methods shown below, when the defined groups change under the conditions of the production methods or are inappropriate for performing the production methods, the desired compound can be produced by performing the methods for the introduction and removal of the protecting groups conventionally performed in the synthetic organic chemistry (e.g., methods described in Protective Groups in Organic Synthesis, third edition, T. W. Greene, John Wiley & Sons Inc., 1999 etc.) or the like. If necessary, the order of the reaction steps can also be changed.

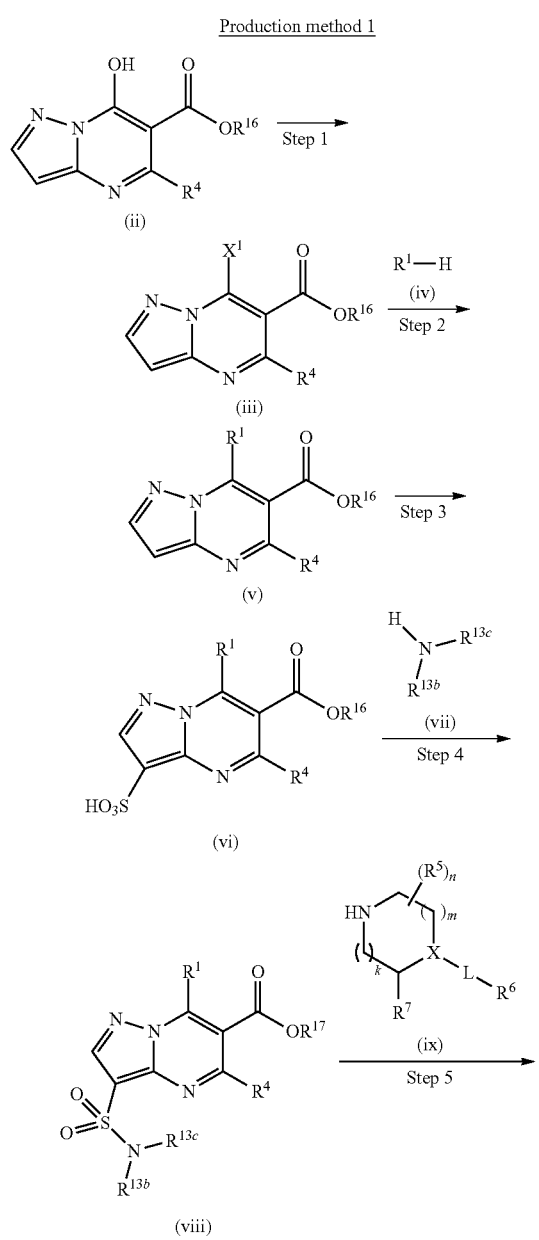

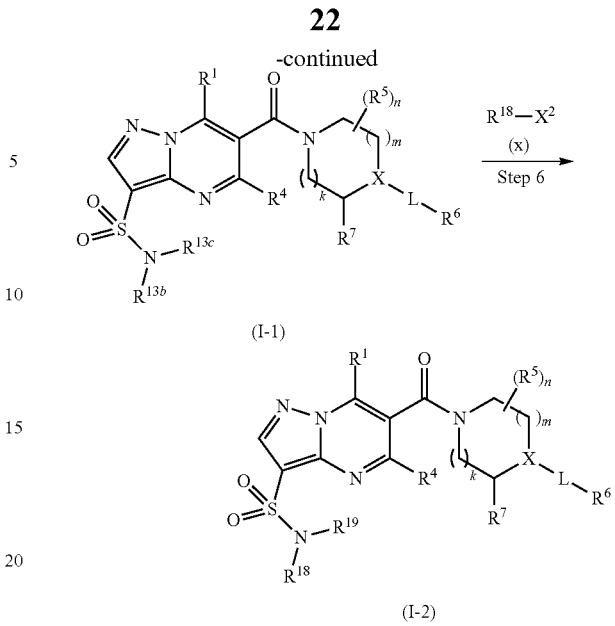

[wherein $R^1$, $R^4$, $R^5$, $R^6$, $R^7$, $R^{13b}$, $R^{13c}$ X, L, k, m and n are each as defined above, $R^{16}$ represents lower alkyl (the lower alkyl is as defined above), $R^{17}$ represents a hydrogen atom or lower alkyl (the lower alkyl is as defined above), $R^{18}$ represents —C(=O)$R^{13e}$ (wherein $R^{13e}$ is as defined above), —C(=S)$R^{13g}$ (wherein $R^{13g}$ is as defined above) or —S(O)$_2$$R^{14}$ (wherein $R^{14}$ is as defined above), $R^{19}$ is as defined for the aforementioned $R^{13d}$, $X^2$ represents a chlorine atom, a bromine atom or hydroxy, and $X^1$ represents a leaving group. Examples of the leaving group include sulfonyloxy such as benzenesulfonyloxy, methanesulfonyloxy, p-toluenesulfonyloxy and the like, groups formed by removing one hydrogen atom from carboxylic acid such as lower alkanoyloxy (lower alkanoyl moiety of said lower alkanoyloxy is as defined for the aforementioned lower alkanoyl), arylcarbonyloxy (aryl moiety of said arylcarbonyloxy is as defined for the aforementioned aryl), aromatic heterocyclecarbonyloxy (aromatic heterocycle moiety of said aromatic heterocyclecarbonyloxy is as defined for the aforementioned aromatic heterocyclic group) and the like, a chlorine atom, a bromine atom, an iodine atom, a fluorine atom and the like]

A conversion reaction of $R^1$, $R^4$, $R^5$, $R^6$, $R^7$, $R^{13b}$, $R^{13c}$, $R^{16}$, $R^{17}$, $R^{18}$, $R^{19}$, $X^1$ and $X^2$ can be performed during any step of (step 1)-(step 6) in the present production method.

(Step 1)

Compound (iii) can be obtained by reacting compound (ii) with 0.5-50 equivalents, preferably a solvent amount, of a leaving group-introducing reagent in an inert solvent or without solvent at a temperature between –30° C. and 150° C. for 15 min-24 hr.

As the leaving group-introducing reagent, a suitable reagent can be selected according to the leaving group to be used. For example, when $X^1$ is a halogen atom such as a chlorine atom, a bromine atom and the like, phosphorus oxychloride, phosphorus oxybromide, phosphorus pentachloride, trichloroacetyl chloride, phosphorus trichloride, phosphorus tribromide, acetyl chloride, thionyl chloride or the like can be used. In this case, 0.5-3 equivalents of, for example, N,N-diisopropylethylamine, N,N-diethylaniline or the like may be added.

Preferably, the reaction is performed using phosphorus oxychloride without solvent at a temperature between 80° C. and 120° C.

Compound (ii) can be synthesized by a known method [for example, the method described in Journal of Medicinal Chemistry, vol. 49, page 2526, 2006] or a method analogous thereto.

(Step 2)

Compound (v) can be obtained by reacting compound (iii) with 0.5-10 equivalents, preferably 1-3 equivalents, of compound (iv) in an inert solvent or without solvent for 15 min-24 hr at a temperature between the melting point and the boiling point of the solvent to be used, and using a base where necessary, and by, when further necessary, irradiating a microwave having an energy of 100-500 (W) under pressurization conditions of 1-20 atm.

Examples of the base include sodium hydroxide, potassium carbonate, sodium hydrogen carbonate, barium hydroxide, cesium carbonate, potassium hydroxide, sodium methoxide, potassium ethoxide, lithium hydroxide, lithium hexamethyldisilasane, sodium hydride, potassium hydride, n-butyllithium, lithium diisopropylamide, potassium tert-butoxide, triethylamine, N,N-diisopropylethylamine, tributylamine, dicyclohexylmethylamine, N-methylmorpholine, pyridine, N-methylpiperidine, 2,6-di-tert-butylpyridine, 1,8-Diazabicyclo[5.4.0]undec-7-ene (DBU), 1,5-Diazabicyclo [4.3.0]non-5-ene (DBN), 4-(dimethylamino)pyridine, Amberlyst A-21 (manufactured by ROHM AND HAAS JAPAN KK.), AG 1-X8 (manufactured by Bio-Rad, Richmond, Calif.), polyvinyl pyridine, morpholinomethylpolystyrene and the like.

The microwave refers to 1 GHz-1 THz electromagnetic wave, and 2450 MHz is preferably used.

The irradiation energy is more preferably 300 W.

Preferably, DMF, N,N-dimethylacetamide or acetonitrile is used as an inert solvent, potassium carbonate, triethylamine or N,N-diisopropylethylamine is used as a base, and the reaction is performed at a temperature between 50° C. and 120° C. for 1-24 hr.

(Step 3)

Compound (vi) can be obtained by reacting compound (v) with 0.5-10 equivalents, preferably 1-3 equivalents, of a sulfonylating agent in an inert solvent or without solvent for 15 min-48 hr at a temperature between −30° C. and the boiling point of the solvent to be used.

Examples of the inert solvent include 1,2-dichloroethane, chloroform, methylene chloride, sulfolane, ethyl acetate and the like, and these can be used singly or in the form of a mixture. Among these, 1,2-dichloroethane or methylene chloride is preferable.

Examples of the sulfonylating agent include chlorosulfonic acid, fuming sulfuric acid, sulfur trioxide, sulfur dioxide and the like.

(Step 4)

Compound (viii) can be obtained from compound (vi) by the following method.

Compound (vi) is treated with 1-20 equivalents, preferably 1-5 equivalents, of an acid halogenating agent in an inert solvent or without solvent for 15 min-48 hr, preferably 1-18 hr, at a temperature between −20° C. and the boiling point of the solvent to be used to give a sulfonic acid halide of compound (vi). In this case, 0.01-0.5 equivalents of DMF, pyridine and the like may be added as necessary. The obtained sulfonic acid halide is reacted with 0.5-5 equivalents, preferably 1-2.5 equivalents, of compound (vii) in the presence of 1-10 equivalents, preferably 1-5 equivalents, of a base in an inert solvent at a temperature between −20° C. and the boiling point of the solvent to be used, preferably between −10° C. and 30° C., for 15 min-48 hr, preferably 1-10 hr, to give compound (viii-b) wherein $R^{17}$ is lower alkyl.

Examples of the inert solvent to be used for the reaction to give a sulfonic acid halide include 1,2-dichloroethane, chloroform, methylene chloride, pyridine, THF, DME, toluene, DMF, dioxane, ethyl acetate and the like, and these can be used singly or in the form of a mixture. Among these, 1,2-dichloroethane, methylene chloride or toluene is preferable.

Examples of the acid halogenating agent include thionyl chloride, oxalyl chloride, phosphorus oxychloride and the like.

Examples of the inert solvent to be used for the reaction of sulfonic acid halide and compound (vii) include 1,2-dichloroethane, chloroform, methylene chloride, pyridine, THF, DME, toluene, DMF, dioxane, ethyl acetate and the like, and these can be used singly or in the form of a mixture. Among these, 1,2-dichloroethane, methylene chloride or DMF is preferable.

Examples of the base include pyridine, triethylamine, 4-(dimethylamino)pyridine, N,N-diisopropylethylamine, aqueous sodium hydrogen carbonate solution, aqueous sodium hydroxide solution and the like. Of these, triethylamine is preferable.

Compound (viii-a) wherein $R^{17}$ is a hydrogen atom can be obtained by treating compound (viii-b) wherein $R^{17}$ is lower alkyl with 0.5-50 equivalents of a suitable base in a solvent or without solvent for 5 min-48 hr at a temperature between −30° C. and the boiling point of the solvent to be used, preferably 0° C. and the boiling point of the solvent to be used.

Examples of the solvent include water, methanol, ethanol, THF, DME, DMF, DMSO, dioxane, acetonitrile, pyridine and the like, and these can be used singly or in the form of a mixture.

Examples of the base include sodium hydroxide, potassium carbonate, sodium hydrogen carbonate, potassium hydroxide, lithium hydroxide, sodium methoxide, potassium ethoxide, lithium iodide/pyridine and the like. Of these, lithium hydroxide or lithium iodide/pyridine is preferable.

For example, Compound (I-a) which is Compound (I) wherein $R^3$ is —$SO_3H$, and Compound (I-b) which is Compound (I) wherein $R^3$ is —$S(O)_2R^{13j}$ (wherein $R^{13j}$ represents lower alkoxy optionally having substituent(s), the lower alkoxy is as defined for the aforementioned lower alkoxy, and the substituent of the substituted lower alkoxy is as defined above) can be produced according to the following reaction.

After compound A is produced, which the 3-position substituent (—$SO_3H$) of compound (vi) is protected, compound A is reacted in the same manner as in step 5 to give compound B which the 6-position substituent ($COOR^{16}$) of compound A is conversed into amide. And then, the 3-position substituent of compound B (protected —$SO_3H$ group) is deprotected to give Compound (I-a).

According to the former paragraph of step 4, a sulfonic acid halide of compound (vi) is obtained and reacted with lower alcohol optionally having substituent(s) to give compound C which is compound (vi) wherein the 3-position substituent is —$S(O)_2R^{13j}$ (wherein $R^{13j}$ is as defined above). And then, compound C is reacted in the same manner as in step 5 to give Compound (I-b).

In the production of Compound (I-a), the protection and deprotection of the 3-position substituent can be performed by, for example, the method described in the aforementioned "Protective groups in Organic Synthesis, third edition, T. W. Greene, John Wiley & Sons Inc. 1999" and the like, and the like.

(Step 5)

Compound (I-1) can be obtained by reacting compound (viii-a) or compound (viii-b) with compound (ix) according to the following <method 1>-<method 4>.

<Method 1>

Compound (viii-a) wherein $R^{17}$ is a hydrogen atom is treated with 1-20 equivalents, preferably 1-5 equivalents, of an acid halogenating agent in an inert solvent or without solvent at a temperature between −20° C. and the boiling point of the solvent to be used, preferably between −10° C. and 30° C., for 15 min-48 hr, preferably 1-18 hr, to give an acid halide of compound (viii-a). In this case, 0.01-0.5 equivalent of DMF, pyridine or the like may be added as necessary. The obtained acid halide is reacted with 0.5-2 equivalents, preferably 1-1.2 equivalents, of compound (ix) in an inert solvent in the presence of 1-5 equivalents, preferably 1-3 equivalents, of a base at a temperature between −20° C. and the boiling point of the solvent to be used, preferably between −10° C. and 30° C., for 15 min-48 hr, preferably 1-10 hr, to give Compound (I-1).

Examples of the inert solvent to be used in the reaction to obtain acid halide include chloroform, methylene chloride, pyridine, THF, DME, toluene, DMF, dioxane, ethyl acetate and the like, and these can be used singly or in the form of a mixture. Among these, methylene chloride or toluene is preferable.

Examples of the acid halogenating agent include thionyl chloride, oxalyl chloride and the like.

Examples of the inert solvent to be used for the reaction of acid halide with compound (ix) include chloroform, methylene chloride, pyridine, THF, DME, toluene, DMF, dioxane, ethyl acetate and the like, and these can be used singly or in the form of a mixture. Among these, methylene chloride or DMF is preferable.

Examples of the base include pyridine, triethylamine, 4-(dimethylamino)pyridine, N,N-diisopropylethylamine, aqueous sodium hydrogen carbonate solution, aqueous sodium hydroxide solution and the like. Among these, triethylamine is preferable.

<Method 2>

Compound (viii-a) wherein $R^{17}$ is a hydrogen atom is reacted with 1-20 equivalents, preferably 1-5 equivalents, of a reagent for synthesizing mixed acid anhydride in an inert solvent or without solvent in the presence of 1-5 equivalents, preferably 1-3 equivalents, of a base at a temperature between −30° C. and 40° C., preferably between −30° C. and 0° C., for 5 min-24 hr, preferably 10 min-2 hr, to give a mixed acid anhydride of compound (viii-a). The obtained mixed acid anhydride is reacted with 0.5-2 equivalents, preferably 1-1.2 equivalents, of compound (ix) at a temperature between −30° C. and 40° C., preferably between −30° C. and 30° C., for 5 min-24 hr, preferably 10 min-2 hr, to give Compound (I-1).

Examples of the inert solvent include chloroform, methylene chloride, pyridine, THF, DME, toluene, DMF, dioxane, acetonitrile, ethyl acetate and the like, and these can be used singly or in the form of a mixture. Among these, THF, DMF or acetonitrile is preferable.

Examples of the base include pyridine, triethylamine, 4-(dimethylamino)pyridine, N-methylmorpholine, N,N-diisopropylethylamine and the like. Among these, N-methylmorpholine or triethylamine is preferable.

Examples of the reagent for synthesizing mixed acid anhydride include isobutyl chloroformate, ethyl chloroformate, pivaloyl chloride, tosyl chloride, mesyl chloride and the like. Among these, isobutyl chloroformate or mesyl chloride is preferable.

<Method 3>

Compound (viii-a) wherein $R^{17}$ is a hydrogen atom is reacted with 0.5-10 equivalents, preferably 0.5-5 equivalents, of compound (ix) in an inert solvent or without solvent, in the presence of 1-20 equivalents, preferably 1-10 equivalents, or in the absence of a base, in the presence of 1-20 equivalents, preferably 1-5 equivalents, of a condensing agent, at a temperature between −30° C. and 60° C., preferably between −30° C. and 40° C., for 30 min-72 hr, preferably 1-18 hr to give Compound (I-1). In this case, 0.5-2 equivalents of, for example, 1-hydroxybenzotriazole (HOBt) or hydrate thereof (HOBt.H$_2$O), or 3-hydroxy-4-oxo-3,4-dihydro-1,2,3-benzotriazine and the like may be added.

Examples of the inert solvent include chloroform, methylene chloride, pyridine, THF, DME, toluene, DMF, DMSO, dioxane, acetonitrile, ethyl acetate and the like, and these can be used singly or in the form of a mixture. Among these, methylene chloride, DMF, THF or acetonitrile is preferable.

Examples of the base include pyridine, triethylamine, 4-(dimethylamino)pyridine, N-methylmorpholine, N,N-diisopropylethylamine and the like. Among these, N,N-diisopropylethylamine or triethylamine is preferable.

Examples of the condensing agent include 1,3-dicyclohexylcarbodiimide, 1-ethyl-3-[3-(dimethylamino)propyl]carbodiimide or hydrochloride thereof, 1,1'-carbonyldiimidazole, 1,3-diisopropylcarbodiimide, diphenylphosphoryl azide, 2-chloro-1-methylpyridinium iodide, 1-benzotriazolyl mesylate, 1-benzotriazolyl tosylate, 1-benzotriazolyl benzenesulfonate, benzotriazol-1-yloxytripyrrolidinophosphonium hexafluorophosphate, 1-propylphosphonic acid anhydride cyclic trimer and the like. Among these, 1,1'-carbonyldiimidazole or benzotriazol-1-yloxytripyrrolidinophosphonium hexafluorophosphate is preferable.

<Method 4>

Compound (viii-b) wherein $R^{17}$ is lower alkyl is reacted with 1-20 equivalents of compound (ix) in an inert solvent or without solvent, in the presence of 1-10 equivalents of an organometallic compound for 15 min-48 hr, preferably 1-18 hr, at a temperature between −78° C. and the boiling point of the solvent to be used, preferably between −30° C. and the boiling point of the solvent to be used, to give Compound (I-1).

Examples of the inert solvent include THF, diethyl ether, toluene, benzene, hexane, pentane and the like, and these can be used singly or in the form of a mixture.

Examples of the organometallic compound include n-butyllithium, sec-butyllithium, trimethylaluminum and the like. Among these, n-butyllithium or trimethylaluminum is preferable.

Compound (I-1c) wherein $R^{13b}$ is a hydrogen atom can also be obtained by treating Compound (I-1b) wherein $R^{13b}$ is tert-butyl with 0.5-50 equivalents or a solvent amount of an acid in an inert solvent or without solvent, at a temperature between −30° C. and the boiling point of the solvent to be used, preferably between 0° C. and the boiling point of the solvent to be used, for 5 min-48 hr. In this case, 0.5-3 equivalents of p-anisole or triethylsilane may be added.

Examples of the inert solvent include chloroform, methylene chloride, 1,2-dichloroethane, toluene, dioxane, ethyl acetate and the like, and these can be used singly or in the form of a mixture. Among these, methylene chloride or 1,2-dichloroethane is preferable.

Examples of the acid include hydrochloric acid, sulfuric acid, trifluoroacetic acid, acetic acid and the like. Among these, trifluoroacetic acid is preferable.

(Step 6)

Compound (I-2) can be obtained by reacting Compound (I-1c) wherein $R^{13b}$ is a hydrogen atom with compound (x) (the following <method 1>-<method 4>).

<Method 1>

Compound (I-1c) is reacted with 1-20 equivalents, preferably 1-5 equivalents, of compound (x) wherein $X^2$ is a chlorine atom or a bromine atom, in an inert solvent or without solvent, in the presence of 1-20 equivalents, preferably 1-5 equivalents, of a base, at a temperature between −20° C. and the boiling point of the solvent to be used, preferably between −10° C. and 50° C., for 15 min-48 hr, preferably 1-18 hr, to give Compound (I-2).

Examples of the inert solvent include chloroform, methylene chloride, pyridine, THF, DME, toluene, DMF, dioxane, ethyl acetate and the like, and these can be used singly or in the form of a mixture. Among these, pyridine, methylene chloride or DMF is preferable.

Examples of the base include pyridine, triethylamine, 4-(dimethylamino)pyridine, 2,6-lutidine, N,N-diisopropylethylamine, aqueous sodium hydrogen carbonate solution, aqueous sodium hydroxide solution and the like. Among these, triethylamine, pyridine or 4-(dimethylamino)pyridine is preferable.

<Method 2>

Compound (x) wherein $X^2$ is hydroxy is treated with 1-20 equivalents, preferably 1-5 equivalents, of an acid halogenating agent in an inert solvent or without solvent, at a temperature between −20° C. and the boiling point of the solvent to be used, preferably between −10° C. and 30° C., for 15 min-48 hr, preferably 1-18 hr to give acid halide of compound (x). In this case, 0.01-0.5 equivalents of DMF, pyridine and the like may be added as necessary. The obtained acid halide is reacted with 0.5-2 equivalents, preferably 1-1.2 equivalents, of Compound (I-1c) in an inert solvent, in the presence of 1-20 equivalents, preferably 1-5 equivalents, of a base, at a temperature between −20° C. and the boiling point of the solvent to be used, preferably between −10° C. and 50° C., for 15 min-48 hr, preferably 1-18 hr, to give Compound (I-2).

Examples of the inert solvent used for the reaction to obtain acid halide include chloroform, methylene chloride, pyridine, THF, DME, toluene, DMF, dioxane, ethyl acetate and the like, and these can be used singly or in the form of a mixture. Among these, methylene chloride or toluene is preferable.

Examples of the acid halogenating agent include thionyl chloride, oxalyl chloride and the like.

Examples of the inert solvent used for the reaction of acid halide and Compound (I-1c) include chloroform, methylene chloride, pyridine, THF, DME, toluene, DMF, dioxane, ethyl acetate and the like, and these can be used singly or in the form of a mixture. Among these, pyridine, methylene chloride or DMF is preferable.

Examples of the base include pyridine, triethylamine, 4-(dimethylamino)pyridine, 2,6-lutidine, N,N-diisopropylethylamine, aqueous sodium hydrogen carbonate solution, aqueous sodium hydroxide solution and the like. Among these, triethylamine, pyridine or 4-(dimethylamino)pyridine is preferable.

<Method 3>

Compound (x) wherein $X^2$ is hydroxy is reacted with 1-20 equivalents, preferably 1-5 equivalents, of a reagent for synthesizing mixed acid anhydride in an inert solvent or without solvent, in the presence of 1-5 equivalents, preferably 1-3 equivalents, of a base, at a temperature between −30° C. and 40° C., preferably between −30° C. and 0° C. for 5 min-24 hr, preferably 10 min-2 hr, to give a mixed acid anhydride of compound (x). The obtained mixed acid anhydride is reacted with 0.5-2 equivalents, preferably 1-1.2 equivalents, of Compound (I-1c) at a temperature between −30° C. and 40° C., preferably between −30° C. and 30° C., for 5 min-24 hr, preferably 10 min-2 hr, to give Compound (I-2).

Examples of the inert solvent include chloroform, methylene chloride, pyridine, THF, DME, toluene, DMF, dioxane, acetonitrile, ethyl acetate and the like, and these can be used singly or in the form of a mixture. Among these, THF, DMF or acetonitrile is preferable.

Examples of the base include pyridine, triethylamine, 4-(dimethylamino)pyridine, N-methylmorpholine, N,N-diisopropylethylamine and the like. Among these, N-methylmorpholine or triethylamine is preferable.

Examples of the reagent for synthesizing mixed acid anhydride include isobutyl chloroformate, ethyl chloroformate, pivaloyl chloride, tosyl chloride, mesyl chloride and the like. Among these, isobutyl chloroformate or mesyl chloride is preferable.

<Method 4>

Compound (x) wherein $X^2$ is hydroxy is reacted with 0.3-20 equivalents, preferably 0.1-10 equivalents, of compound (I-1c) in an inert solvent or without solvent in the presence or absence of 1-20 equivalents, preferably 1-10 equivalents, of a base in the presence of 1-20 equivalents, preferably 1-5 equivalents, of a condensing agent at a temperature between −30° C. and 100° C., preferably between 0° C. and 80° C., for 30 min-72 hr, preferably 1-30 hr, to give Compound (I-2). In this case, 0.5-2 equivalents of, for example, HOBt, $HOBt.H_2O$, 3-hydroxy-4-oxo-3,4-dihydro-1,2,3-benzotriazine or the like may be added.

Examples of the inert solvent include chloroform, methylene chloride, pyridine, THF, DME, toluene, DMF, DMSO, dioxane, acetonitrile, ethyl acetate and the like, and these can be used singly or in the form of a mixture. Among these, methylene chloride, DMF, THF or acetonitrile is preferable.

Examples of the base include pyridine, triethylamine, 4-(dimethylamino)pyridine, N-methylmorpholine, N,N-diisopropylethylamine, DBU, DBN and the like. Among these, DBU, N,N-diisopropylethylamine or triethylamine is preferable.

Examples of the condensing agent include 1,3-dicyclohexylcarbodiimide, 1-ethyl-3-[3-(dimethylamino)propyl] carbodiimide or hydrochloride thereof, 1,1'-carbonyldiimidazole, 1,3-diisopropylcarbodiimide, diphenylphosphoryl azide, 2-chloro-1-methylpyridinium iodide, 1-benzotriazolyl mesylate, 1-benzotriazolyl tosylate, 1-benzotriazolyl benzenesulfonate, benzotriazol-1-yloxytripyrrolidinophosphonium hexafluorophosphate, 1-propylphosphonic acid anhydride cyclic trimer and the like. Among these, 1-ethyl-3-[3-(dimethylamino)propyl]carbodiimide or hydrochloride thereof or 1,1'-carbonyldiimidazole is preferable.

Production method 2

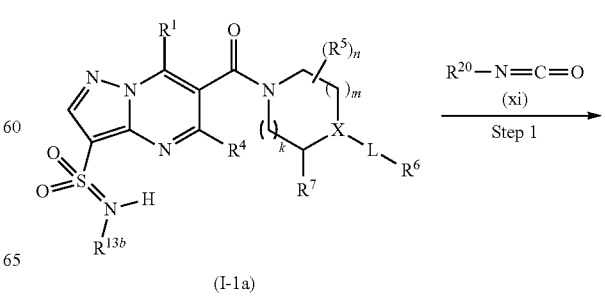

(I-1a)

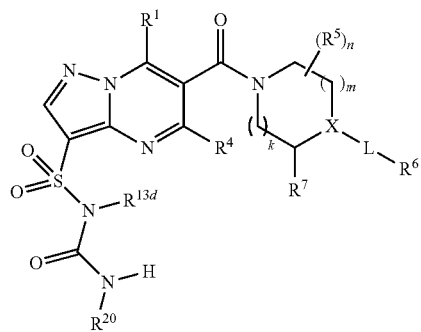

(I-3)

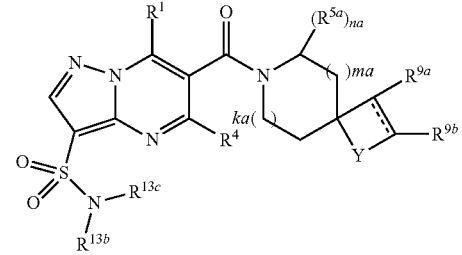

(I-4)

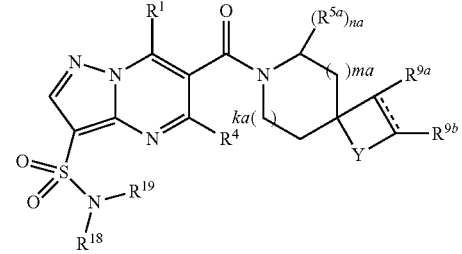

(I-5)

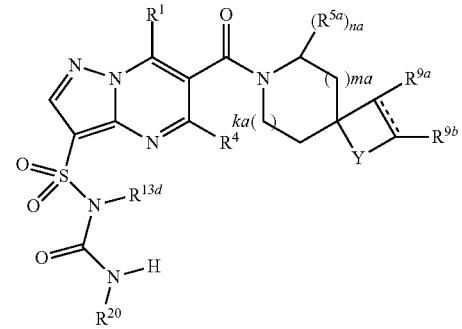

(I-6)

[wherein R¹, R⁴, R⁵, R⁶, R⁷, R¹³ᵇ, R¹³ᵈ, X, L, k, m and n are each as defined above, R²⁰ represents lower alkyl optionally having substituent(s) (the lower alkyl is as defined above, and the substituent of the substituted lower alkyl is as defined above) or aryl optionally having substituent(s) (the aryl is as defined above, and the substituent of the substituted aryl is as defined above)]

A conversion reaction of each of R¹, R⁴, R⁵, R⁶, R⁷, R¹³ᵇ, R¹³ᵈ and R²⁰ can be performed during step 1 of the production method.

(Step 1)

Compound (I-3) can be obtained by reacting Compound (I-1a) which is Compound (I-1) wherein R¹³ᵇ is a hydrogen atom with 0.5-50 equivalents, preferably 3-20 equivalents, of compound (xi) or an equivalent thereof in an inert solvent or without solvent, in the presence of 1-20 equivalents, preferably 1-5 equivalents, of a base, at a temperature between −30° C. and 150° C. for 15 min-48 hr.

Examples of the inert solvent include chloroform, methylene chloride, THF, DME, toluene, DMF, dioxane, ethyl acetate, acetone, methylethyl ketone and the like, and these can be used singly or in the form of a mixture. Among these, dioxane, acetone or methylethylketone is preferable.

Examples of the base include pyridine, triethylamine, 4-(dimethylamino)pyridine, 2,6-lutidine, N,N-diisopropylethylamine, sodium carbonate, potassium carbonate and the like. Among these, potassium carbonate or N,N-diisopropylethylamine is preferable.

The following Compound (I-4), (I-5) and (I-6) can be obtained using the corresponding cyclic amine, compound (XX)

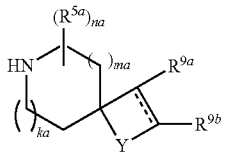

(XX)

(wherein ---, R⁵ᵃ, R⁹ᵃ, R⁹ᵇ, Y, ka, ma and na are each as defined above), and by a method similar to the above-mentioned production methods 1 and 2.

(wherein ---, R¹, R⁴, R⁵ᵃ, R⁹ᵃ, R⁹ᵇ, R¹³ᵇ, R¹³ᶜ, R¹³ᵈ, R¹⁸, R¹⁹, R²⁰, Y ka, ma and na are each as defined above)

The following Compounds (I-9), (I-10) and (I-11) can be obtained using the corresponding amine, compound (XXX)

(XXX)

wherein Rᶻ, R⁵ᵇ, R⁷ᵇ, nb and nc are each as defined above, and by a method similar to the above-mentioned production methods 1 and 2.

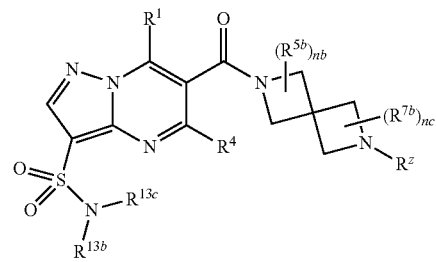

(I-9)

-continued

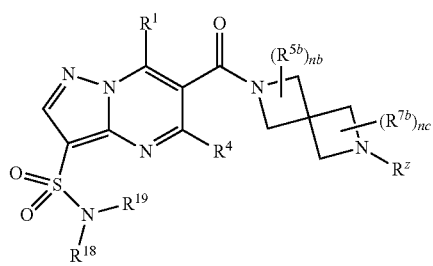

(I-10)

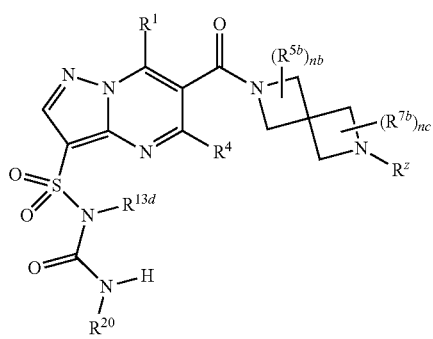

(I-11)

(wherein $R^1$, $R^4$, $R^{5b}$, $R^{7b}$, $R^z$, $R^{13b}$, $R^{13c}$, $R^{13d}$, $R^{18}$, $R^{19}$, $R^{20}$, nb and nc are each as defined above)

Each functional group in Compound (I) and Compound (IA) can also be converted by a known method [e.g., the method described in Comprehensive Organic Transformations 2nd edition, R. C. Larock, Vch Verlagsgesellschaft Mbh, 1999 and the like] or similar methods thereto.

The intermediates and the desired compounds in the above-mentioned respective production methods can be isolated and purified by applying separation purification methods usually used in the synthetic organic chemistry such as filtration, extraction, washing, drying, concentration, recrystallization, various chromatographies or the like. In addition, intermediates can also be subjected to a next reaction without particular purification.

When a salt of Compound (I) or (IA) is to be obtained, Compound (I) or (IA) obtained in the form of a salt can be directly purified. When it is obtained in a free form, Compound (I) or (IA) may be dissolved or suspended in a suitable solvent, and an acid or base is added thereto to form a salt, which may be isolated and purified.

Specific examples of the structural formulas of Compounds (I) and (IA) obtained by the present invention are shown in Table 1-1 to Table 1-8. However, the compounds of the present invention are not limited thereto.

TABLE 1-1

(I-7)

| Compound No. | *—$R^1$ | | *—$R^4$ | *—$R^3$ |
|---|---|---|---|---|
| a-1 | 2-CH3, 4-F anilino | 4-phenylpiperidinyl | *—H | cyclopropanecarbonyl sulfonamide |
| a-2 | 2-CH3, 4-F anilino | 4-phenylpiperidinyl | *—H | N-ethyl sulfonamide |
| a-3 | 2-CH3, 4-F anilino | 4-(4-fluorophenyl)piperidinyl | *—H | N-ethyl sulfonamide |

TABLE 1-1-continued
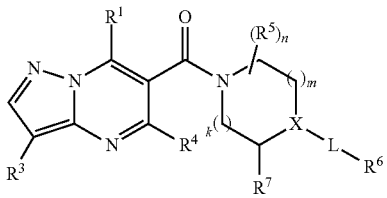
(I-7)
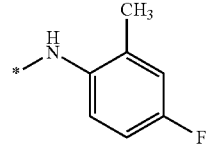 [SMILES: *Nc1ccc(F)cc1C]
| Compound No. | *—R¹ | | *—R⁴ | *—R³ |
|---|---|---|---|---|
| a-4 | 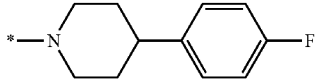 | 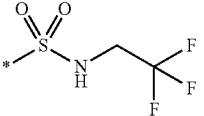 [SMILES: *S(=O)(=O)NCC(F)(F)F] | *—H | 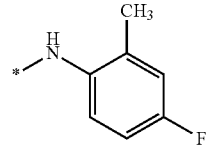 [SMILES: *Nc1ccc(F)cc1C] |
| a-5 | 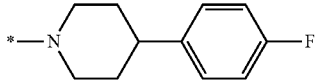 | 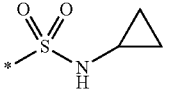 [SMILES: *S(=O)(=O)NC1CC1] | *—H | 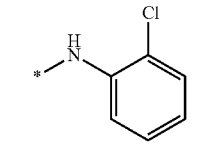 [SMILES: *Nc1ccccc1Cl] |
| a-6 | 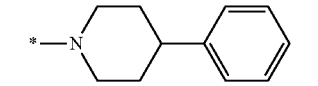 | 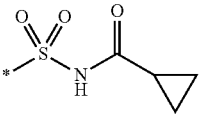 [SMILES: *S(=O)(=O)NC(=O)C1CC1] | *—H | 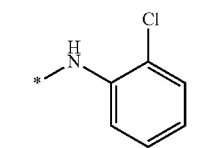 [SMILES: *Nc1ccccc1Cl] |
| a-7 | 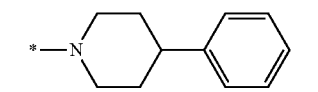 | 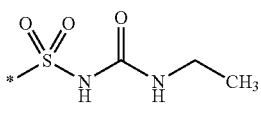 [SMILES: *S(=O)(=O)NC(=O)NCC] | *—H | 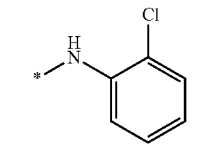 |
| a-8 | 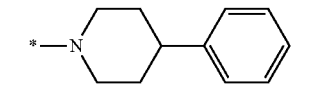 | 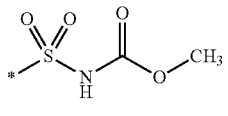 [SMILES: *S(=O)(=O)NC(=O)OC] | *—H | 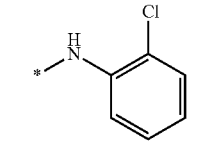 [SMILES: *Nc1ccccc1Cl] |
| a-9 | 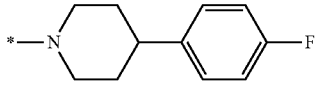 [SMILES: *N1CCC(c2ccc(F)cc2)CC1] | 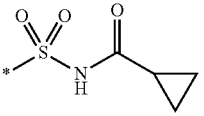 [SMILES: *S(=O)(=O)NC(=O)C1CC1] | *—H | 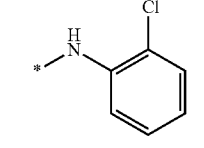 [SMILES: *Nc1ccccc1Cl] |
| a-10 | 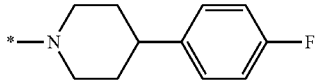 [SMILES: *N1CCC(c2ccc(F)cc2)CC1] | | *—H | 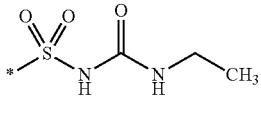 [SMILES: *S(=O)(=O)NC(=O)NCC] |

TABLE 1-2
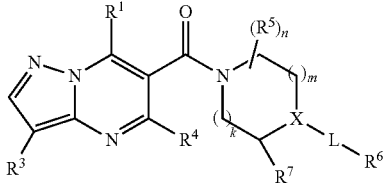
(I-7)
| Compound No. | *—R¹ | (structure) | *—R⁴ | *—R³ |
|---|---|---|---|---|
| a-11 | 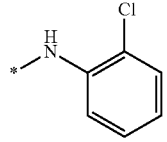 | 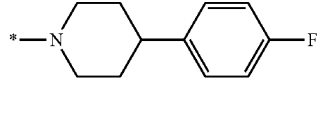 | *—H | 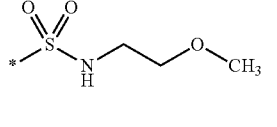 |
| a-12 | 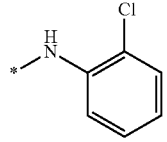 | 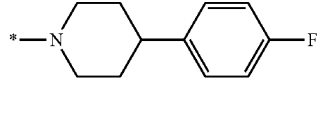 | *—H | 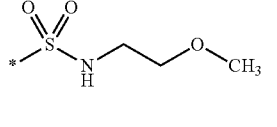 |
| a-13 | 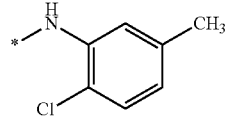 [SMILES: *Nc1cc(C)ccc1Cl] | 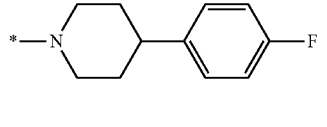 [SMILES: *N1CCC(c2ccc(F)cc2)CC1] | *—H | 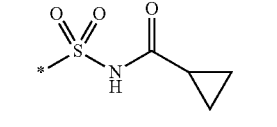 |
| a-14 | 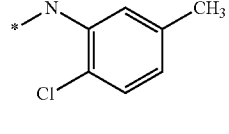 | 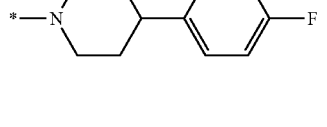 | *—H | 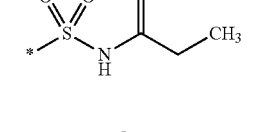 |
| a-15 | 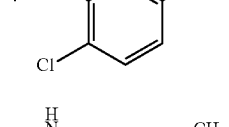 | 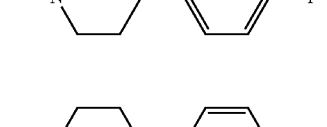 | *—H | 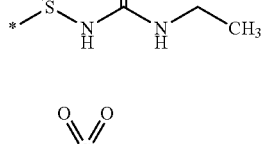 |
| a-16 | 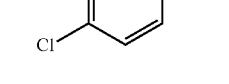 |  | *—H | 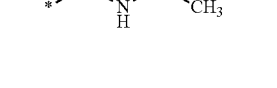 |
| a-17 | 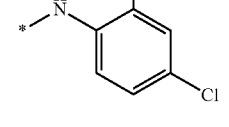 | 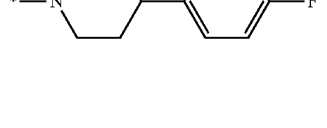 | *—H | 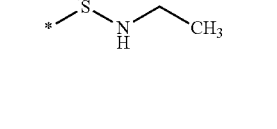 |
| a-18 | 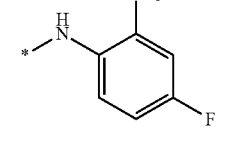 | 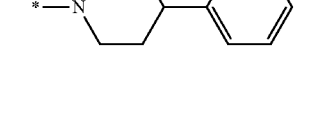 | *—H | 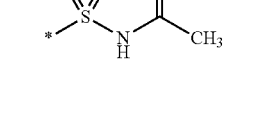 |

TABLE 1-2-continued (I-7)

| Compound No. | *—R¹ | *—N group (R⁵)ₙ, X—L—R⁶, R⁷ | *—R⁴ | *—R³ |
|---|---|---|---|---|
| a-19 | 2,4-dichlorophenyl-NH- | *—N-piperidinyl-(4-fluorophenyl) | *—H | *—S(O)₂—NH—C(O)—CH₂CH₃ |
| a-20 | 2,4-dichlorophenyl-NH- | *—N-piperidinyl-(4-fluorophenyl) | *—H | *—S(O)₂—NH—C(O)—NH—CH₂CH₃ |

TABLE 1-3

(I-7)

| Compound No. | *—R¹ | *—N group (R⁵)ₙ, X—L—R⁶, R⁷ | *—R⁴ | *—R³ |
|---|---|---|---|---|
| a-21 | 2-chloro-4-fluorophenyl-NH- | *—N-piperidinyl-(4-fluorophenyl) | *—H | *—S(O)₂—NH—C(O)—NH-cyclopropyl |
| a-22 | 2,5-dichlorophenyl-NH- | *—N-piperidinyl-(4-fluorophenyl) | *—H | *—S(O)₂—NH—C(O)—CH₂CH₃ |
| a-23 | 2,5-dichlorophenyl-NH- | *—N-piperidinyl-(4-fluorophenyl) | *—H | *—S(O)₂—NH—C(O)—NH—CH₂CH₃ |

TABLE 1-3-continued (I-7)

| Compound No. | *—R¹ | (structure) R⁷ | *—R⁴ | *—R³ |
|---|---|---|---|---|
| a-24 | 2,5-dichloro-NH-phenyl | 4-(4-fluorophenyl)piperidin-1-yl | *—H | *—S(O)₂NHC(O)CH₃ |
| a-25 | 2,5-dichloro-NH-phenyl | 4-(4-fluorophenyl)piperidin-1-yl | *—H | *—S(O)₂NHC(O)(3-methyloxetan-3-yl) |
| a-26 | 2,5-dichloro-NH-phenyl | 4-(4-fluorophenyl)piperidin-1-yl | *—H | *—S(O)₂NHCHO |
| a-27 | 2,5-dichloro-NH-phenyl | 4-(4-fluorophenyl)piperidin-1-yl | *—H | *—S(O)₂NHOCH₃ |
| a-28 | 2,5-dichloro-NH-phenyl | 4-(4-fluorophenyl)piperidin-1-yl | *—H | *—S(O)₂NHOCH₂CH₃ |
| a-29 | 2-chloro-5-trifluoromethyl-NH-phenyl | 4-(4-fluorophenyl)piperidin-1-yl | *—H | *—S(O)₂NHC(O)CH₂CH₃ |
| a-30 | 2-chloro-5-fluoro-NH-phenyl | 4-(4-fluorophenyl)piperidin-1-yl | *—H | *—S(O)₂NHC(O)NHCH₂CH₃ |

TABLE 1-4
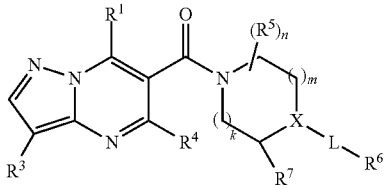
(I-7)
| Compound No. | *—R¹ | 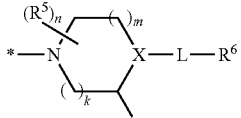 | *—R⁴ | *—R³ |
|---|---|---|---|---|
| a-31 | 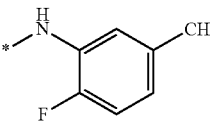 | 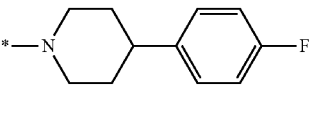 [SMILES: *N1CCC(c2ccc(F)cc2)CC1] | *—H | 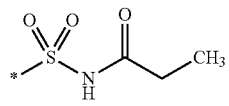 [SMILES: *S(=O)(=O)NC(=O)CC] |
| a-32 | 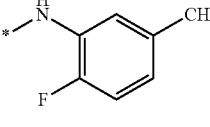 | 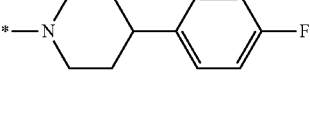 | *—H | 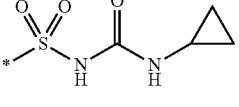 |
| a-33 |  | 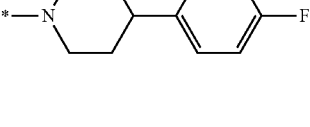 | *—H | 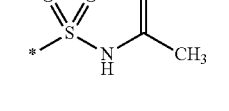 |
| a-34 | 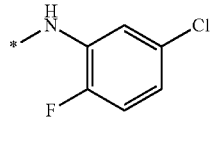 [SMILES: *Nc1cc(Cl)ccc1F] | 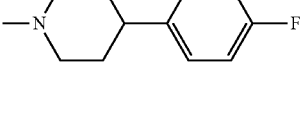 | *—H | 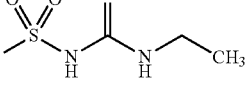 |
| a-35 | 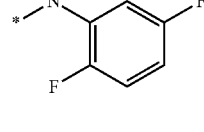 | 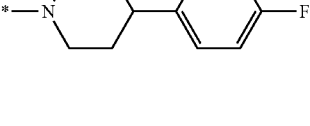 | *—H | 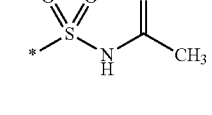 |
| a-36 | 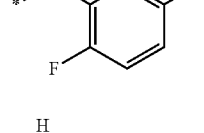 | 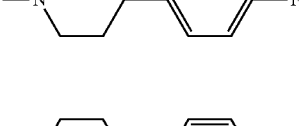 | *—H | 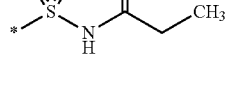 |
| a-37 | 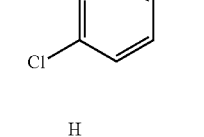 |  | *—H | 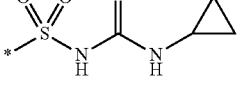 |
| a-38 | 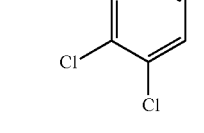 | 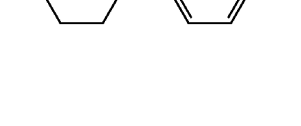 | *—H | 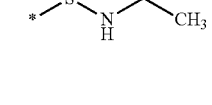 |

TABLE 1-4-continued
(I-7)
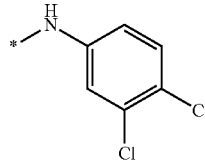
| Compound No. | *—R¹ | (structure) | *—R⁴ | *—R³ |
|---|---|---|---|---|
| a-39 | 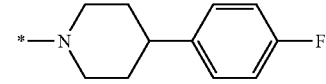 [SMILES: *N1CCC(c2ccc(F)cc2)CC1] | 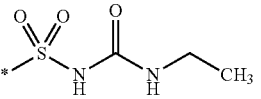 [SMILES: *S(=O)(=O)NC(=O)NCC] | *—H | 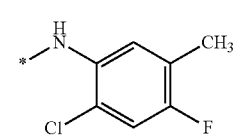 [SMILES: *Nc1cc(C)c(F)cc1Cl] |
TABLE 1-5
(I-7)
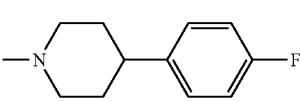
| Compound No. | *—R¹ | (structure) | *—R⁴ | *—R³ |
|---|---|---|---|---|
| a-40 | 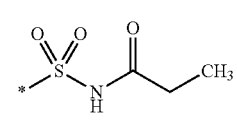 [SMILES: *S(=O)(=O)NC(=O)CC] | 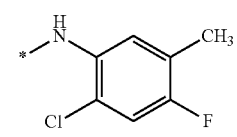 [SMILES: *Nc1cc(C)c(F)cc1Cl] | *—H | 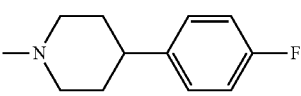 |
| a-41 | 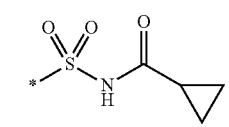 | 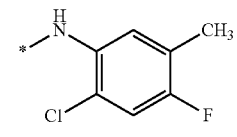 [SMILES: *Nc1cc(C)c(F)cc1Cl] | *—H | 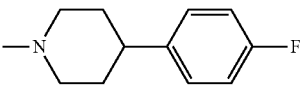 |
| a-42 | 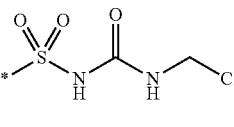 | 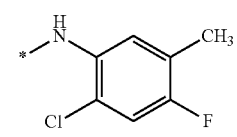 [SMILES: *Nc1cc(C)c(F)cc1Cl] | *—H | 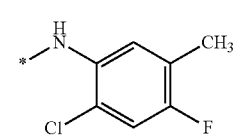 [SMILES: *Nc1cc(C)c(F)cc1Cl] |

TABLE 1-6

TABLE 1-6-continued (I-8)

| Compound No. | *—R¹ | *—N piperidine-spiro | *—R⁴ | *—R³ |
|---|---|---|---|---|
| a-50 | 2-Cl, 4-F anilino (*—NH-C₆H₃(Cl)(F)) | spiro[piperidine-4,1'-isobenzofuran] | *—H | *—S(O)₂NH-C(O)-CH₂CH₃ |

TABLE 1-7

(I-8)

| Compound No. | *—R¹ | *—N piperidine-spiro | *—R⁴ | *—R³ |
|---|---|---|---|---|
| a-51 | 2-F, 5-CH₃ anilino | spiro[piperidine-4,1'-isobenzofuran] | *—H | *—S(O)₂NH-C(O)-CH₂CH₃ |
| a-52 | 2-F, 5-CH₃ anilino | spiro[piperidine-4,1'-isobenzofuran] | *—H | *—S(O)₂NH-C(O)-cyclopropyl |
| a-53 | 2,5-di-Cl anilino | spiro[piperidine-4,1'-isobenzofuran] | *—H | *—S(O)₂NH-C(O)-CH₂CH₃ |

TABLE 1-7-continued (I-8)

| Compound No. | *—R¹ | *—N piperidine-spiro-isobenzofuran (R⁵ᵃ, R⁹ᵃ, R⁹ᵇ, Y) | *—R⁴ | *—R³ |
|---|---|---|---|---|
| a-54 | 2,5-dichloroanilino (NH-C₆H₃(Cl)₂) | N-piperidine-spiro-isobenzofuran | *—H | *—S(O)₂NHC(O)-cyclopropyl |
| a-55 | 2-chloro-5-methylanilino | N-piperidine-spiro-isobenzofuran | *—H | *—S(O)₂NHC(O)CH₃ |
| a-56 | 2-chloro-5-methylanilino | N-piperidine-spiro-isobenzofuran | *—H | *—S(O)₂NHC(O)CH₂CH₃ |
| a-57 | 2-chloro-5-methylanilino | N-piperidine-spiro-isobenzofuran | *—H | *—S(O)₂NHC(O)-cyclobutyl |
| a-58 | 2-chloro-5-methylanilino | N-piperidine-spiro-isobenzofuran | *—H | *—S(O)₂NHC(O)-(3-methyloxetan-3-yl) |
| a-59 | 2-chloro-5-methylanilino | N-piperidine-spiro-isobenzofuran | *—H | *—S(O)₂NHC(O)NH-(2,2-difluorocyclopropyl) |

TABLE 1-8

(I-12)

[Structure of compound I-12 with R¹, R³, R⁴, and substituted azetidine-spiro-azetidine with $(R^{5b})_{nb}$, $(R^{7b})_{nc}$, and $R^Z$ groups on pyrazolopyrimidine core]

| Compound No. | *—R¹ | [azetidine-spiro] $(R^{5b})_{nb}$, $(R^{7b})_{nc}$, N—R^Z | *—R⁴ | *—R³ |
|---|---|---|---|---|
| a-60 | 2-Cl-5-CH₃-phenyl-NH- | azetidine-spiro-azetidine-N-(4-F-phenyl) | *—H | *—S(=O)₂—NH—C(=O)—CH₂CH₃ |
| a-61 | 2-Cl-5-CH₃-phenyl-NH- | azetidine-spiro-azetidine-N-(4-F-phenyl) | *—H | *—S(=O)₂—NH—C(=O)—NH—CH₂CH₃ |

Next, the pharmacological action of the representative compound is specifically explained by Test Examples.

Test Example 1

Suppressive Action on Dinitrofluorobenzene-Induced Ear Edema Reaction in Mouse

5-Week to 6-week old BALE/c mice (female, supplied by CHARLES RIVER LABORATORIES JAPAN, INC) were purchased and, after quarantine and habituation, those showing satisfactory body weight increase and free of abnormal appearance were used to start the test from 7 weeks of age. The animals were housed and bred in plastic cages (6 mice per cage) in a breeding chamber set at room temperature 19-25° C., humidity 30-70%, 12 hr illumination per day (7 a.m.-7 p.m.), with free access to a commercially available solid feed and water.

One day before the test, the abdomen was shaved, and a solution of dinitrofluorobenzene (manufactured by Nacalai Tesque) in acetone (manufactured by Wako Pure Chemical Industries, Ltd.) {concentration 0.5% [weight (w)/volume (v) %]} was applied to the shaved part of BALE/c mice by 100 μL for sensitization. On day 5 after sensitization, a dinitrofluorobenzene-acetone solution [concentration 0.2% (w/v %)] was applied to the front and the back of the auricle by 10 μL each (total 20 μL) to induce reaction. A test compound dissolved in acetone to the concentration of 1% (w/v %) was applied to the front and the back of the auricle 1 hr before and 3 hr after the induction of reaction each by 10 μL (total 20 μL). After the application, the applied part was air-dried by a dryer.

A group administered with the test compound by coating was taken as a test compound administration group, and a group administered with acetone (solvent) by coating instead of the test compound was taken as a solvent administration group. In addition, a group free of sensitization and induction of reaction and administered with acetone by coating instead of the test compound was taken as a normal group. The thickness of the auricle was measured immediately before induction of reaction and 24 hr after the induction with a dial thickness gauge (manufactured by OZAKI MFG. CO., LTD., G-1A), and the difference between them was taken as ear edema. The ear edema suppressive rate (%) was calculated according to the following formula. The results are shown in Table 2.

[formula 1]

$$\text{ear edema suppressive rate (\%)} = \frac{\begin{bmatrix}\text{value of solvent}\\\text{administration group}\end{bmatrix} - \begin{bmatrix}\text{value of test compound}\\\text{administration group}\end{bmatrix}}{\begin{bmatrix}\text{value of solvent}\\\text{adminstration group}\end{bmatrix} - \begin{bmatrix}\text{value of normal}\\\text{group}\end{bmatrix}} \times 100$$

TABLE 2

| compound No. | ear edema suppressive rate (%) |
|---|---|
| a-6 | 30 |
| a-14 | 25 |
| a-43 | 40 |

Test Example 2

Suppressive Action on Dinitrofluorobenzene-Induced Ear Edema Reaction in Mouse

5-Week old BALE/c mice (female, supplied by CHARLES RIVER LABORATORIES JAPAN, INC) were purchased and, after quarantine and habituation, those showing satisfactory body weight increase and free of abnormal appearance were used to start the test from 7 weeks of age. The animals were housed and bred in plastic cages (6 mice per cage) in a breeding chamber set at room temperature 19-25° C., humidity 30-70%, 12 hr illumination per day (7 a.m.-7 p.m.), with free access to a commercially available solid feed and water.

One day before the test, the abdomen was shaved, and a solution of dinitrofluorobenzene (manufactured by Nacalai Tesque) in acetone (manufactured by Wako Pure Chemical Industries, Ltd.) {concentration 0.5% [weight (w)/volume (v) %]} was applied to the shaved part of BALE/c mice by 100 μL for sensitization. On day 5 after sensitization, a dinitrofluorobenzene-acetone solution [concentration 0.2% (w/v %)] was applied to the front and the back of the auricle by 10 μL each (total 20 μL) to induce reaction. A test compound dissolved in 50% acetone/50% ethanol (w/v %) to the concentration of 1% (w/v %) was applied to the front and the back of the auricle 1 hr before and 3 hr after the induction of reaction each by 10 μL (total 20 μL). After the application, the applied part was air-dried by a dryer.

A group administered with the test compound by coating was taken as a test compound administration group, and a group administered with 50% acetone/50% ethanol (w/v %) (solvent) by coating instead of the test compound was taken as a solvent administration group. In addition, a group free of sensitization and induction of reaction and administered with 50% acetone/50% ethanol (w/v %) by coating instead of the test compound was taken as a normal group. The thickness of the auricle was measured immediately before induction of reaction and 24 hr after the induction with a dial thickness gauge (manufactured by OZAKI MFG. CO., LTD., G-1A), and the difference between them was taken as ear edema. The ear edema suppressive rate (%) was calculated according to the following formula. The results are shown in Table 2.

$$\text{ear edema suppressive rate (\%)} = \frac{\begin{bmatrix}\text{value of solvent}\\\text{administration group}\end{bmatrix} - \begin{bmatrix}\text{value of test compound}\\\text{administration group}\end{bmatrix}}{\begin{bmatrix}\text{value of solvent}\\\text{adminstration group}\end{bmatrix} - \begin{bmatrix}\text{value of normal}\\\text{group}\end{bmatrix}} \times 100 \quad \text{[formula 2]}$$

TABLE 3

| compound No. | ear edema suppressive rate (%) |
|---|---|
| a-22 | 16 |
| a-27 | 47 |
| a-40 | 32 |
| a-60 | 5 |

From the above results, the compound of the present invention was found to have an action to suppress ear edema and treat skin diseases.

The Compounds (I) and (IA) of the present invention and pharmaceutically acceptable salts thereof can be administered alone as they are, generally, they are desirably provided as various pharmaceutical preparations. In addition, such pharmaceutical preparations are used for animals and humans.

The pharmaceutical preparation relating to the present invention can contain, as an active ingredient, Compounds (I) and (IA) of the present invention or a pharmaceutically acceptable salt thereof alone or as a mixture with an active ingredient for any other treatment. Moreover, the pharmaceutical preparation can be produced by mixing the active ingredient with one or more kinds of pharmaceutically acceptable carriers (e.g., diluent, solvent, excipient or the like) according to any method well known in the technical field of pharmaceutical science.

As the administration route, a route most effective for the treatment is desirably employed, which may be an oral or parenteral route such as intravenous route, external route or the like.

The dosage form may be, for example, tablet, injection, ointment or the like.

Tablet can be produced by using an excipient such as lactose or the like, a disintegrant such as starch or the like, a lubricant such as magnesium stearate or the like, a binder such as hydroxypropylcellulose or the like, and is suitable for oral administration.

Injection or the like can be produced by using a diluent such as a salt solution, a glucose solution or a mixture of salt solution and a glucose solution or the like, or a solvent or the like.

Ointment can be produced from a base such as petrolatum and the like and an additive such as stearyl alcohol and the like.

The dose and administration frequency of Compounds (I) and (IA) of the present invention or a pharmaceutically acceptable salt thereof varies depending on the mode of administration, age and body weight of patients, nature and severity of the symptom to be treated or the like, it is generally within the range of 0.01 to 1000 mg, preferably 0.05 to 100 mg, for oral administration to an adult, which is administered at once or in several portions a day. In the case of intravenous administration, external administration or the like, 0.001 to 1000 mg, preferably 0.01 to 100 mg, is administered to an adult at once or in several portions a day. However, these doses and administration frequencies vary depending on the aforementioned various conditions.

The present invention is explained in more detail in the following by Examples and Reference Examples, which are not to be construed as limitative.

The proton nuclear magnetic resonance spectrum ($^1$H NMR) used in the Examples and Reference Examples were measured at 270 MHz or 300 MHz, and exchanging protons may not be clearly observed depending on the compound and measurement conditions. The indication of the multiplicity of the signals is conventional, where br means an apparently broad signal.

Example 1

N-[7-(4-fluoro-2-methylphenylamino)-6-(4-phenylpiperidine-1-carbonyl)pyrazolo[1,5-a]pyrimidin-3-ylsulfonyl]cyclopropanecarboxamide (compound a-1)

(Step 1)

Ethyl 7-(4-fluoro-2-methylphenylamino)pyrazolo[1,5-a]pyrimidine-6-carboxylate

Ethyl 7-hydroxypyrazolo[1,5-a]pyrimidine-6-carboxylate (Journal of Medicinal Chemistry, vol. 49, page 2526, 2006) (3.20 g, 15.5 mmol) was dissolved in phosphorus oxychloride (30 mL), N,N-diisopropylethylamine (5.4 mL, 30.9 mmol) was added, and the mixture was stirred with heating at 100° C. for 3 hr. After confirmation of consumption the starting materials, phosphorus oxychloride was evaporated under reduced pressure, and the residue was dissolved in ethyl acetate. The solution was added dropwise to a saturated aqueous sodium hydrogen carbonate solution under ice-cooling. To the saturated aqueous sodium hydrogen carbonate solution was added ethyl acetate, and the mixture was extracted 3 times. The combined organic layer was dried over anhydrous magnesium sulfate, and concentrated under reduced pressure.

The obtained residue was dissolved in N,N-dimethylacetamide (30 mL), 4-fluoro-2-methylaniline (2.2 mL, 20.1 mmol) and N,N-diisopropylethylamine (5.4 mL, 30.9 mmol) were added, and the mixture was stirred with heating at 80° C. for 2 hr. After cooling, to the reaction mixture was added dropwise 5% aqueous citric acid solution, chloroform was added, and the mixture was extracted 3 times. The combined organic layer was dried over anhydrous magnesium sulfate, and concentrated under reduced pressure. The obtained residue was purified by silica gel column chromatography (hexane/ethyl acetate=2/1) to give the title compound (3.14 g, 65%). ESI-MS m/z: 315 (M+H)$^+$; $^1$H-NMR (CDCl$_3$, δ): 1.42 (t, J=7.2 Hz, 3H), 2.22 (s, 3H), 4.38 (q, J=7.2 Hz, 2H), 6.46 (d, J=2.3 Hz, 1H), 6.55-7.09 (m, 3H), 7.83 (d, J=2.3 Hz, 1H), 8.83 (s, 1H), 10.69 (s, 1H).
(Step 2)

6-ethoxycarbonyl-7-(4-fluoro-2-methylphenylamino)pyrazolo[1,5-a]pyrimidine-3-sulfonic acid Ethyl 7-(4-fluoro-2-methylphenylamino)pyrazolo[1,5-a]pyrimidine-6-carboxylate (0.500 g, 1.59 mmol) obtained in step 1 was dissolved in methylene chloride (6 mL), chlorosulfonic acid (0.21 mL, 3.19 mmol) was added, and the mixture was stirred at room temperature overnight. The reaction mixture was concentrated under reduced pressure, a 1/1 mixed solvent of diisopropyl ether and 2-propanol was added, and the mixture was stirred at room temperature for 1 hr. The resulting crystals were suction filtered and washed with 2-propanol to give the title compound (0.580 g, 92%). ESI-MS m/z: 395 (M+H)$^+$; $^1$H-NMR (CDCl$_3$, δ): 1.13 (t, J=7.2 Hz, 3H), 2.29 (s, 3H), 3.94 (q, J=7.2 Hz, 2H), 6.96-7.46 (m, 4H), 8.28 (s, 1H), 8.50 (s, 1H).
(Step 3)

Ethyl 3-(N-tert-butylsulfamoyl)-7-(4-fluoro-2-methylphenylamino)pyrazolo[1,5-a]pyrimidine-6-carboxylate 6-Ethoxycarbonyl-7-(4-fluoro-2-methylphenylamino)pyrazolo[1,5-a]pyrimidine-3-sulfonic acid (0.400 g, 1.01 mmol) obtained in step 2 was dissolved in 1,2-dichloroethane (4 mL), thionyl chloride (0.29 mL, 4.05 mmol) and DMF (0.024 mL, 0.304 mmol) were added, and the mixture was heated under reflux for 2 hr. The reaction mixture was concentrated under reduced pressure, the obtained residue was dissolved in methylene chloride (4 mL), tert-butylamine (0.21 mL, 2.02 mmol) and triethylamine (0.35 mL, 2.53 mmol) were added dropwise and the mixture was stirred at room temperature for 2 hr. 1 mol/L hydrochloric acid was added dropwise to the reaction mixture, and the mixture was extracted 3 times with chloroform. The combined organic layer was dried over anhydrous magnesium sulfate, and concentrated under reduced pressure to give the title compound (0.29 g, 63%).

ESI-MS m/z: 450 (M+H)$^+$; $^1$H-NMR (CDCl$_3$, δ): 1.22 (s, 9H), 1.44 (t, J=7.2 Hz, 3H), 2.18 (s, 3H), 4.43 (q, J=7.2 Hz, 2H), 6.82-7.12 (m, 4H), 8.06 (s, 1H), 9.01 (s, 1H), 10.90 (s, 1H).
(Step 4)

N-tert-butyl-7-(4-fluoro-2-methylphenylamino)-6-(4-phenylpiperidine-1-carbonyl)pyrazolo[1,5-a]pyrimidine-3-sulfonamide Ethyl 3-(N-tert-butylsulfamoyl)-7-(4-fluoro-2-methylphenylamino)pyrazolo[1,5-a]pyrimidine-6-carboxylate (0.28 g, 0.624 mmol) obtained in step 3 was dissolved in ethanol (2 mL), 2 mol/L aqueous sodium hydroxide solution (2 mL) was added, and the mixture was stirred with heating at 80° C. for 4 hr. Under ice-cooling, 2 mol/L hydrochloric acid was added dropwise to adjust the reaction mixture to pH 1, and the mixture was extracted 3 times with chloroform. The combined organic layer was dried over anhydrous magnesium sulfate, and concentrated under reduced pressure.

The residue (0.265 g) obtained above was dissolved in DMF (3 mL), 1-ethyl-3-[3-(dimethylamino)propyl]carbodiimide hydrochloride (0.142 g, 0.748 mmol), 1-hydroxybenzotriazole monohydrate (0.113 g, 0.748 mmol) and 4-phenylpiperidine (0.120 g, 0.748 mmol) were added, and the mixture was stirred at room temperature overnight. To the reaction mixture was added dropwise saturated aqueous sodium hydrogen carbonate solution, and the mixture was extracted 3 times with chloroform. The combined organic layer was dried over anhydrous magnesium sulfate, and concentrated under reduced pressure. The obtained residue was purified by silica gel column chromatography (chloroform/methanol=9/1) to give the title compound (0.143 g, 41%).

ESI-MS m/z: 565 (M+H)$^+$; $^1$H-NMR (CDCl$_3$, δ): 1.28 (s, 9H), 1.39-1.58 (m, 2H), 1.77-1.89 (m, 2H), 2.40 (s, 3H), 2.59-2.74 (m, 1H), 3.85-4.26 (m, 4H), 5.04 (s, 1H), 6.89-7.40 (m, 8H), 8.16 (s, 1H), 8.35 (s, 1H), 8.39 (s, 1H).
(Step 5)

7-(4-fluoro-2-methylphenylamino)-6-(4-phenylpiperidine-1-carbonyl)pyrazolo[1,5-a]pyrimidine-3-sulfonamide N-tert-Butyl-7-(4-fluoro-2-methylphenylamino)-6-(4-phenylpiperidine-1-carbonyl)pyrazolo[1,5-a]pyrimidine-3-sulfonamide (0.874 g, 1.548 mmol) obtained in step 4 was dissolved in trifluoroacetic acid (13 mL), anisole (0.4 mL) was added, and the mixture was stirred at room temperature overnight. The reaction mixture was concentrated under reduced pressure, the obtained residue was purified by silica gel column chromatography (chloroform/methanol=10/1) to give the title compound (0.442 g, 56%).

ESI-MS m/z: 509 (M+H)$^+$; $^1$H-NMR (DMSO-d$_6$, δ): 1.57-1.71 (m, 4H), 2.27 (s, 3H), 2.64-2.73 (m, 1H), 3.78-3.82 (m, 2H), 4.01-4.05 (m, 2H), 7.05-7.33 (m, 10H), 8.28 (s, 1H), 8.45 (s, 1H), 10.04 (s, 1H).
(Step 6)

N-[7-(4-fluoro-2-methylphenylamino)-6-(4-phenylpiperidine-1-carbonyl)pyrazolo[1,5-a]pyrimidin-3-ylsulfonyl]cyclopropanecarboxamide (compound a-1)

Cyclopropanecarboxylic acid (0.066 g, 0.768 mmol) was dissolved in DMF (0.8 mL), and 1,1'-carbonyldiimidazole (0.125 g, 0.768 mmol) was added. After stirring at room temperature for 30 min, 7-(4-fluoro-2-methylphenylamino)-

6-(4-phenylpiperidine-1-carbonyl)pyrazolo[1,5-a]pyrimidine-3-sulfonamide (0.078 g, 0.154 mmol) obtained in step 5 and 1,8-diazabicyclo[5.4.0]undeca-7-en (0.140 g, 0.922 mmol) were added, and the mixture was stirred at 80° C. for 3 hr. 5% Aqueous citric acid solution was added to quench the reaction, and the precipitated crystals were collected by filtration. The obtained crystals were purified by silica gel column chromatography (chloroform/methanol=10/1) to give the title compound (0.026 g, 29%).

ESI-MS m/z: 577 (M+H)$^+$; $^1$H-NMR (CDCl$_3$, δ): 0.82-0.90 (m, 2H), 1.00-1.06 (m, 2H), 1.44-1.55 (m, 2H), 1.56-1.61 (m, 1H), 1.80-1.85 (m, 2H), 2.39 (s, 3H), 2.61-2.71 (m, 1H), 3.83-4.15 (m, 4H), 6.96 (td, J=8.2, 2.5 Hz, 1H), 7.08 (dd, J=9.1, 2.8 Hz, 1H), 7.14-7.23 (m, 4H), 7.30-7.36 (m, 2H), 8.23 (s, 1H), 8.44 (s, 1H), 8.61 (s, 1H), 9.54 (s, 1H).

Example 2

N-ethyl-7-(4-fluoro-2-methylphenylamino)-6-(4-phenylpiperidine-1-carbonyl)pyrazolo[1,5-a]pyrimidine-3-sulfonamide (compound a-2)

(Step 1)

Ethyl 3-(N-ethylsulfamoyl)-7-(4-fluoro-2-methylphenylamino)pyrazolo[1,5-a]pyrimidine-6-carboxylate Using 6-ethoxycarbonyl-7-(4-fluoro-2-methylphenylamino)pyrazolo[1,5-a]pyrimidine-3-sulfonic acid (0.500 g, 1.268 mmol) obtained in Example 1 step 2 and ethylamine (2.0 mol/L THF solution; 2.5 mL, 5.071 mmol) instead of tert-butylamine, and in the same manner as in Example 1 step 3, the title compound (0.178 g, 33%) was obtained.

(Step 2)

N-ethyl-7-(4-fluoro-2-methylphenylamino)-6-(4-phenylpiperidine-1-carbonyl)pyrazolo[1,5-a]pyrimidine-3-sulfonamide (compound a-2)

Using ethyl 3-(N-ethylsulfamoyl)-7-(4-fluoro-2-methylphenylamino)pyrazolo[1,5-a]pyrimidine-6-carboxylate (0.178 g, 0.423 mmol) obtained in step 1 and in the same manner as in Example 1 step 4, the title compound (0.057 g, 25%) was obtained.

ESI-MS m/z: 537 (M+H)$^+$; $^1$H-NMR (CDCl$_3$, δ): 1.17 (t, J=7.3 Hz, 3H), 1.43-1.55 (m, 2H), 1.80-1.86 (m, 2H), 2.40 (s, 3H), 2.62-2.71 (m, 1H), 3.02-3.12 (m, 2H), 3.75-4.00 (m, 4H), 4.94 (t, J=5.8 Hz, 1H), 6.96 (td, J=8.3, 3.0 Hz, 1H), 7.08 (dd, J=8.8, 2.8 Hz, 1H), 7.14-7.36 (m, 6H), 8.17 (s, 1H), 8.33 (s, 1H), 8.43 (s, 1H).

Example 3

N-ethyl-7-(4-fluoro-2-methylphenylamino)-6-[4-(4-fluorophenyl)piperidine-1-carbonyl]pyrazolo[1,5-a]pyrimidine-3-sulfonamide (compound a-3)

Using ethyl 3-(N-ethylsulfamoyl)-7-(4-fluoro-2-methylphenylamino)pyrazolo[1,5-a]pyrimidine-6-carboxylate (0.483 g, 1.145 mmol) obtained in Example 2 step 1 and 4-(4-fluorophenyl)piperidine hydrochloride (0.099 g, 0.458 mmol) instead of 4-phenylpiperidine, and in the same manner as in Example 1 step 4, the title compound (0.020 g, 3%) was obtained.

ESI-MS m/z: 555 (M+H)$^+$; $^1$H-NMR (CDCl$_3$, δ): 1.17 (t, J=7.3 Hz, 3H), 1.42-1.52 (m, 2H), 1.78-1.84 (m, 2H), 2.40 (s, 3H), 2.61-2.70 (m, 1H), 3.02-3.12 (m, 2H), 3.93-4.19 (m, 4H), 5.04 (s, 1H), 6.87-7.20 (m, 7H), 8.20 (s, 1H), 8.32 (s, 1H), 8.43 (s, 1H).

Example 4

7-(4-fluoro-2-methylphenylamino)-6-[4-(4-fluorophenyl)piperidine-1-carbonyl]-N-(2,2,2-trifluoroethyl)pyrazolo[1,5-a]pyrimidine-3-sulfonamide (compound a-4)

(Step 1)

Ethyl 7-(4-fluoro-2-methylphenylamino)-3-[N-(2,2,2-trifluoroethyl)sulfamoyl]pyrazolo[1,5-a]pyrimidine-6-carboxylate Using 6-ethoxycarbonyl-7-(4-fluoro-2-methylphenylamino)pyrazolo[1,5-a]pyrimidine-3-sulfonic acid (0.970 g, 2.460 mmol) obtained in Example 1 step 2 and 2,2,2-trifluoroethylamine (0.975 g, 9.838 mmol) instead of tert-butylamine, and in the same manner as in Example 1 step 3, the title compound (1.024 g, 87%) was obtained.

(Step 2)

7-(4-fluoro-2-methylphenylamino)-6-[4-(4-fluorophenyl)piperidine-1-carbonyl]-N-(2,2,2-trifluoroethyl)pyrazolo[1,5-a]pyrimidine-3-sulfonamide (compound a-4)

Using ethyl 7-(4-fluoro-2-methylphenylamino)-3-[N-(2,2,2-trifluoroethyl)sulfamoyl]pyrazolo[1,5-a]pyrimidine-6-carboxylate (0.142 g, 0.298 mmol) obtained in step 1 and 4-(4-fluorophenyl)piperidine hydrochloride (0.072 g, 0.335 mmol) instead of 4-phenylpiperidine, and in the same manner as in Example 1 step 4, the title compound (0.028 g, 21%) was obtained.

ESI-MS m/z: 609 (M+H)$^+$; $^1$H-NMR (CDCl$_3$, δ): 1.39-1.52 (m, 2H), 1.79-1.84 (m, 2H), 2.39 (s, 3H), 2.60-2.69 (m, 1H), 3.69-3.80 (m, 2H), 4.11-4.30 (m, 4H), 5.68 (s, 1H), 6.91-7.20 (m, 7H), 8.19 (s, 1H), 8.33 (s, 1H), 8.41 (s, 1H).

Example 5

N-cyclopropyl-7-(4-fluoro-2-methylphenylamino)-6-[4-(4-fluorophenyl)piperidine-1-carbonyl]pyrazolo[1,5-a]pyrimidine-3-sulfonamide (compound a-5)

(Step 1)

Ethyl 3-(N-cyclopropylsulfamoyl)-7-(4-fluoro-2-methylphenylamino)-pyrazolo[1,5-a]pyrimidine-6-carboxylate Using 6-ethoxycarbonyl-7-(4-fluoro-2-methylphenylamino)pyrazolo[1,5-a]pyrimidine-3-sulfonic acid (0.400 g, 1.145 mmol) obtained in Example 1 step 2 and cyclopropylamine (0.261 g, 4.580 mmol) instead of tert-butylamine, and in the same manner as in Example 1 step 3, the title compound (0.496 g, 100%) was obtained.

(Step 2)

N-cyclopropyl-7-(4-fluoro-2-methylphenylamino)-6-[4-(4-fluorophenyl)piperidine-1-carbonyl]pyrazolo[1,5-a]pyrimidine-3-sulfonamide (compound a-5)

Using ethyl 3-(N-cyclopropylsulfamoyl)-7-(4-fluoro-2-methylphenylamino)-pyrazolo[1,5-a]pyrimidine-6-carboxylate (0.496 g, 1.145 mmol) obtained in step 1 and 4-(4-fluorophenyl)piperidine hydrochloride (0.072 g, 0.335 mmol) instead of 4-phenylpiperidine, and in the same manner as in Example 1 step 4, the title compound (0.0283 g, 3%) was obtained.

ESI-MS m/z: 567 (M+H)$^+$; $^1$H-NMR (CDCl$_3$, δ): 0.61-0.64 (m, 2H), 0.72-0.76 (m, 2H), 1.38-1.51 (m, 2H), 1.78-1.83 (m, 2H), 2.25-2.30 (m, 1H), 2.40 (s, 3H), 2.61-2.69 (m, 1H), 4.07-4.23 (m, 4H), 5.49 (s, 1H), 6.91-7.20 (m, 7H), 8.19 (s, 1H), 8.33 (s, 1H), 8.48 (s, 1H).

Example 6

N-[7-(2-chlorophenylamino)-6-(4-phenylpiperidine-1-carbonyl)pyrazolo[1,5-a]pyrimidin-3-ylsulfonyl] cyclopropanecarboxamide (compound a-6)

(Step 1)

Ethyl 7-(2-chlorophenylamino)pyrazolo[1,5-a]pyrimidine-6-carboxylate

Using ethyl 7-hydroxypyrazolo[1,5-a]pyrimidine-6-carboxylate (3.00 g, 14.5 mmol) and 2-chloroaniline (2.77 g, 21.7 mmol) instead of 4-fluoro-2-methylaniline, and in the same manner as in Example 1 step 1, the title compound (1.44 g, 31%) was obtained.
(Step 2)

7-(2-chlorophenylamino)-6-(ethoxycarbonyl)pyrazolo[1,5-a]pyrimidine-3-sulfonic acid Using ethyl 7-(2-chlorophenylamino)pyrazolo[1,5-a]pyrimidine-6-carboxylate (1.44 g, 4.55 mmol) obtained in step 1 and in the same manner as in Example 1 step 2, the title compound (1.70 g, 94%) was obtained.
(Step 3)

Ethyl 3-(N-tert-butylsulfamoyl)-7-(2-chlorophenylamino)pyrazolo[1,5-a]pyrimidine-6-carboxylate Using 7-(2-chlorophenylamino)-6-(ethoxycarbonyl)pyrazolo[1,5-a]pyrimidine-3-sulfonic acid (1.70 g, 4.30 mmol) obtained in step 2 and in the same manner as in Example 1 step 3, the title compound (1.94 g, 100%) was obtained.
(Step 4)

N-tert-butyl-7-(2-chlorophenylamino)-6-(4-phenylpiperidine-1-carbonyl)pyrazolo[1,5-a]pyrimidine-3-sulfonamide Using ethyl 3-(N-tert-butylsulfamoyl)-7-(2-chlorophenylamino)pyrazolo[1,5-a]pyrimidine-6-carboxylate (1.94 g, 4.30 mmol) obtained in step 3 and in the same manner as in Example 1 step 4, the title compound (0.804 g, 33%) was obtained.
(Step 5)

7-(2-chlorophenylamino)-6-(4-phenylpiperidine-1-carbonyl)pyrazolo[1,5-a]pyrimidine-3-sulfonamide Using N-tert-butyl-7-(2-chlorophenylamino)-6-(4-phenylpiperidine-1-carbonyl)pyrazolo[1,5-a]pyrimidine-3-sulfonamide (0.804 g, 1.417 mmol) obtained in step 4 and in the same manner as in Example 1 step 5, the title compound (0.499 g, 69%) was obtained.

(Step 6)

N-[7-(2-chlorophenylamino)-6-(4-phenylpiperidine-1-carbonyl)pyrazolo[1,5-a]pyrimidin-3-ylsulfonyl] cyclopropanecarboxamide (compound a-6)

Using 7-(2-chlorophenylamino)-6-(4-phenylpiperidine-1-carbonyl)pyrazolo[1,5-a]pyrimidine-3-sulfonamide (0.050 g, 0.098 mmol) obtained in step 5 and in the same manner as in Example 1 step 6, the title compound (0.034 g, 29%) was obtained.

ESI-MS m/z: 579 (M+H)$^+$; $^1$H-NMR (CDCl$_3$, δ): 0.84-0.90 (m, 2H), 1.01-1.06 (m, 2H), 1.36-1.50 (m, 2H), 1.56-1.59 (m, 1H), 1.76-1.81 (m, 2H), 2.56-2.64 (m, 1H), 3.61-3.74 (m, 2H), 4.12-4.32 (m, 2H), 7.11-7.14 (m, 2H), 7.20-7.42 (m, 6H), 7.54-7.59 (m, 1H), 8.53 (s, 1H), 8.62 (s, 1H), 8.64 (s, 1H), 9.47 (s, 1H).

Example 7

7-(2-chlorophenylamino)-N-(ethylcarbamoyl)-6-(4-phenylpiperidine-1-carbonyl)pyrazolo[1,5-a]pyrimidine-3-sulfonamide (compound a-7)

7-(2-Chlorophenylamino)-6-(4-phenylpiperidine-1-carbonyl)pyrazolo[1,5-a]pyrimidine-3-sulfonamide (0.050 g, 0.098 mmol) obtained in Example 6 step 5 was dissolved in acetone (0.5 mL), potassium carbonate (0.041 g, 0.293 mmol) and ethylisocyanate (0.017 g, 0.245 mmol) were added, and the mixture was stirred at 50° C. for 2 hr. Saturated aqueous ammonium chloride solution was added to quench the reaction, and the mixture was extracted 3 times with ethyl acetate. The organic layers were combined, washed with saturated brine, dried over anhydrous sodium sulfate, and concentrated under reduced pressure. The obtained residue was purified by silica gel column chromatography (chloroform/methanol=99/1) to give the title compound (0.027 g, 48%).

ESI-MS m/z: 582 (M+H)$^+$; $^1$H-NMR (CDCl$_3$, δ): 1.16 (t, J=7.3 Hz, 3H), 1.35-1.47 (m, 2H), 1.77-1.81 (m, 2H), 2.57-2.65 (m, 1H), 3.22-3.31 (m, 2H), 3.72-3.85 (m, 2H), 4.15-4.30 (m, 2H), 6.71 (s, 1H), 7.11-7.14 (m, 2H), 7.20-7.44 (m, 6H), 7.55-7.61 (m, 1H), 7.95 (s, 1H), 8.45 (s, 1H), 8.52 (s, 2H).

Example 8

Methyl 7-(2-chlorophenylamino)-6-(4-phenylpiperidine-1-carbonyl)pyrazolo[1,5-a]pyrimidin-3-ylsulfonylcarbamate (compound a-8)

7-(2-Chlorophenylamino)-6-(4-phenylpiperidine-1-carbonyl)pyrazolo[1,5-a]pyrimidine-3-sulfonamide (0.070 g, 0.137 mmol) obtained in Example 6 step 5 was dissolved in dichloromethane (0.7 mL), and the solution was cooled to 0° C. Pyridine (0.325 g, 4.110 mmol) and methyl chloroformate (0.350 g, 3.699 mmol) were added, the mixture was stirred at room temperature for 48 hr, and 1 mol/L hydrochloric acid was added to quench the reaction. The organic layer was separated, and the aqueous layer was extracted twice with chloroform. The organic layers were combined, washed with saturated brine, dried over anhydrous sodium sulfate, and concentrated under reduced pressure. The obtained residue was purified by silica gel column chromatography (chloroform/methanol=99/1) to give the title compound (0.031 g, 40%).

ESI-MS m/z: 569 (M+H)$^+$; $^1$H-NMR (CDCl$_3$, δ): 1.35-1.51 (m, 2H), 1.76-1.81 (m, 2H), 2.56-2.65 (m, 1H), 3.70 (s,

3H), 4.06-4.40 (m, 4H), 7.11-7.14 (m, 2H), 7.20-7.43 (m, 6H), 7.57 (dd, J=6.8, 2.4 Hz, 1H), 8.49 (s, 1H), 8.53 (s, 1H), 8.59 (s, 1H), 8.63 (s, 1H).

Example 9

N-{7-(2-chlorophenylamino)-6-[4-(4-fluorophenyl)piperidine-1-carbonyl]pyrazolo[1,5-a]pyrimidin-3-ylsulfonyl}cyclopropanecarboxamide (compound a-9)

(Step 1)

N-tert-butyl-7-(2-chlorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chlorophenylamino)pyrazolo[1,5-a]pyrimidine-6-carboxylate (4.25 g, 8.82 mmol) obtained in Example 6 step 3 and 4-(4-fluorophenyl)piperidine (1.87 g, 10.46 mmol) instead of 4-phenylpiperidine, and in the same manner as in Example 1 step 4, the title compound (2.42 g, 59%) was obtained.

(Step 2)

7-(2-chlorophenylamino)-6-[4-(4-fluorophenyl)piperidine-1-carbonyl]pyrazolo[1,5-a]pyrimidine-3-sulfonamide Using N-tert-butyl-7-(2-chlorophenylamino)-6-[4-(4-fluorophenyl)piperidine-1-carbonyl]pyrazolo[1,5-a]pyrimidine-3-sulfonamide (2.24 g, 4.14 mmol) obtained in step 1 and in the same manner as in Example 1 step 5, the title compound (1.49 g, 68%) was obtained.

(Step 3)

N-{7-(2-chlorophenylamino)-6-[4-(4-fluorophenyl)piperidine-1-carbonyl]pyrazolo[1,5-a]pyrimidin-3-ylsulfonyl}cyclopropanecarboxamide (compound a-9)

Using 7-(2-chlorophenylamino)-6-[4-(4-fluorophenyl)piperidine-1-carbonyl]pyrazolo[1,5-a]pyrimidine-3-sulfonamide (0.080 g, 0.151 mmol) obtained in step 2 and in the same manner as in Example 1 step 6, the title compound (0.080 g, 89%) was obtained.

ESI-MS m/z: 597 (M+H)$^+$; $^1$H-NMR (DMSO-d$_6$, δ): 0.64-0.82 (m, 4H), 1.40-1.78 (m, 4H), 1.98-2.23 (m, 1H), 2.62-2.75 (m, 1H), 2.93-3.08 (m, 1H), 3.37-3.43 (m, 1H), 3.76-4.02 (m, 2H), 7.09-7.55 (m, 8H), 8.36 (s, 1H), 8.56 (s, 1H), 10.40 (s, 1H).

Example 10

7-(2-chlorophenylamino)-N-(ethylcarbamoyl)-6-[4-(4-fluorophenyl)piperidine-1-carbonyl]pyrazolo[1,5-a]pyrimidine-3-sulfonamide (compound a-10)

Using 7-(2-chlorophenylamino)-6-[4-(4-fluorophenyl)piperidine-1-carbonyl]pyrazolo[1,5-a]pyrimidine-3-sulfonamide (0.080 g, 0.151 mmol) obtained in Example 9 step 2 and in the same manner as in Example 7, the title compound (0.106 g, 94%) was obtained.

ESI-MS m/z: 600 (M+H)$^+$; $^1$H-NMR (DMSO-d$_6$, δ): 0.94 (t, J=7.1 Hz, 3H), 1.21-1.69 (m, 4H), 2.07-2.23 (m, 1H), 2.64-2.74 (m, 1H), 2.93-3.03 (m, 2H), 3.01-3.07 (m, 1H), 3.75-4.04 (m, 2H), 5.70 (s, 1H), 6.39 (t, J=5.6 Hz, 1H), 7.09-7.57 (m, 8H), 8.34 (s, 1H), 8.56 (s, 1H), 10.42 (s, 1H).

Example 11

7-(2-chlorophenylamino)-6-[4-(4-fluorophenyl)piperidine-1-carbonyl]-N-(2-methoxyethyl)pyrazolo[1,5-a]pyrimidine-3-sulfonamide (compound a-11)

(Step 1)

Ethyl 7-(2-chlorophenylamino)-3-[N-(2-methoxyethyl)sulfamoyl]pyrazolo[1,5-a]pyrimidine-6-carboxylate Using 7-(2-chlorophenylamino)-6-(ethoxycarbonyl)pyrazolo[1,5-a]pyrimidine-3-sulfonic acid (0.400 g, 1.008 mmol) obtained in Example 6 step 2 and 2-methoxyethylamine (0.303 g, 4.032 mmol) instead of tert-butylamine, and in the same manner as in Example 1 step 3, the title compound (0.459 g, 100%) was obtained.

(Step 2)

7-(2-chlorophenylamino)-6-[4-(4-fluorophenyl)piperidine-1-carbonyl]-N-(2-methoxyethyl)pyrazolo[1,5-a]pyrimidine-3-sulfonamide (compound a-11)

Using ethyl 7-(2-chlorophenylamino)-3-[N-(2-methoxyethyl)sulfamoyl]pyrazolo[1,5-a]pyrimidine-6-carboxylate (0.459 g, 1.008 mmol) obtained in step 1 and 4-(4-fluorophenyl)piperidine (0.158 g, 0.881 mmol) instead of 4-phenylpiperidine, and in the same manner as in Example 1 step 4, the title compound (0.086 g, 15%) was obtained.

ESI-MS m/z: 587 (M+H)$^+$; $^1$H-NMR (CDCl$_3$, δ): 1.31-1.45 (m, 2H), 1.74-1.79 (m, 2H), 2.55-2.64 (m, 1H), 3.20-3.26 (m, 2H), 3.30 (s, 3H), 3.49 (t, J=5.1 Hz, 2H), 3.89-4.26 (m, 4H), 5.37 (t, J=5.9 Hz, 1H), 6.96-7.10 (m, 4H), 7.28-7.42 (m, 3H), 7.54-7.57 (m, 1H), 8.44 (s, 1H), 8.49 (s, 1H), 8.49 (s, 1H).

Example 12

N-{7-(2-chloro-5-methylphenylamino)-6-[4-(4-fluorophenyl)piperidine-1-carbonyl]pyrazolo[1,5-a]pyrimidin-3-ylsulfonyl}cyclopropanecarboxamide (compound a-12)

(Step 1)

Ethyl 7-(2-chloro-5-methylphenylamino)pyrazolo[1,5-a]pyrimidine-6-carboxylate

Using ethyl 7-hydroxypyrazolo[1,5-a]pyrimidine-6-carboxylate (5.00 g, 24.1 mmol) and 2-chloro-5-methylaniline (8.54 g, 60.3 mmol) instead of 4-fluoro-2-methylaniline, and in the same manner as in Example 1 step 1, the title compound (2.94 g, 37%) was obtained.

(Step 2)

7-(2-chloro-5-methylphenylamino)-6-(ethoxycarbonyl)pyrazolo[1,5-a]pyrimidine-3-sulfonic acid Using ethyl 7-(2-chloro-5-methylphenylamino)pyrazolo[1,5-a]pyrimidine-6-carboxylate (2.94 g, 8.89 mmol) obtained in step 1 and in the same manner as in Example 1 step 2, the title compound (3.60 g, 99%) was obtained.

(Step 3)

Ethyl 3-(N-tert-butylsulfamoyl)-7-(2-chloro-5-methylphenylamino)pyrazolo[1,5-a]pyrimidine-6-carboxylate Using 7-(2-chloro-5-methylphenylamino)-6-(ethoxycarbonyl)pyrazolo[1,5-a]pyrimidine-3-sulfonic acid (3.00 g, 7.30 mmol) obtained in step 2 and in the same manner as in Example 1 step 3, the title compound (3.30 g, 97%) was obtained.

(Step 4)

N-tert-butyl-7-(2-chloro-5-methylphenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chloro-5-methylphenylamino)pyrazolo[1,5-a]pyrimidine-6-carboxylate (2.31 g, 4.96 mmol) obtained in step 3 and 4-(4-fluorophenyl)piperidine (0.92 g, 5.14 mmol) instead of 4-phenylpiperidine, and in the same manner as in Example 1 step 4, the title compound (0.85 g, 41%) was obtained.

(Step 5)

7-(2-chloro-5-methylphenylamino)-6-[4-(4-fluorophenyl)piperidine-1-carbonyl]pyrazolo[1,5-a]pyrimidine-3-sulfonamide Using N-tert-butyl-7-(2-chloro-5-methylphenylamino)-6-[4-(4-fluorophenyl)piperidine-1-carbonyl]pyrazolo[1,5-a]pyrimidine-3-sulfonamide (0.85 g, 1.42 mmol) obtained in step 4 and in the same manner as in Example 1 step 5, the to title compound (0.42 g, 55%) was obtained.

(Step 6)

N-{7-(2-chloro-5-methylphenylamino)-6-[4-(4-fluorophenyl)piperidine-1-carbonyl]pyrazolo[1,5-a]pyrimidin-3-ylsulfonyl}cyclopropanecarboxamide(compound a-12)

Using 7-(2-chloro-5-methylphenylamino)-6-[4-(4-fluorophenyl)piperidine-1-carbonyl]pyrazolo[1,5-a]pyrimidine-3-sulfonamide (0.08 g, 0.147 mmol) obtained in step 5 and in the same manner as in Example 1 step 6, the title compound (0.072 g, 80%) was obtained.

ESI-MS m/z: 611 (M+H)$^+$; $^1$H-NMR (CDCl$_3$, δ): 0.82-0.89 (m, 2H), 1.00-1.06 (m, 2H), 1.31-1.48 (m, 2H), 1.56-1.59 (m, 1H), 1.71-1.76 (m, 2H), 2.35 (s, 3H), 2.52-2.56 (m, 1H), 3.61-3.74 (m, 2H), 4.12-4.32 (m, 2H), 6.94-7.13 (m, 5H), 7.22 (br s, 1H), 7.42 (d, J=8.3 Hz, 1H), 8.50 (br s, 1H), 8.65 (s, 1H), 8.76 (s, 1H), 9.77 (br s, 1H).

Example 13

N-{7-(2-chloro-5-methylphenylamino)-6-[4-(4-fluorophenyl)piperidine-1-carbonyl]pyrazolo[1,5-a]pyrimidin-3-ylsulfonyl}ethanecarboxamide (compound a-13)

Using 7-(2-chloro-5-methylphenylamino)-6-[4-(4-fluorophenyl)piperidine-1-carbonyl]pyrazolo[1,5-a]pyrimidine-3-sulfonamide (0.08 g, 0.147 mmol) obtained in Example 12 step 5 and propionic acid (0.055 mL, 0.737 mmol) instead of cyclopropanecarboxylic acid, and in the same manner as in Example 1 step 6, the title compound (0.081 g, 92%) was obtained.

ESI-MS m/z: 599 (M+H)$^+$; $^1$H-NMR (CDCl$_3$, δ): 1.08 (d, J=7.3 Hz, 3H), 1.35-1.48 (m, 2H), 1.71-1.76 (m, 2H), 2.36 (s, 3H), 2.37 (q, J=7.3 Hz, 2H), 2.52-2.61 (m, 1H), 3.61-3.74 (m, 2H), 4.12-4.32 (m, 2H), 6.94-7.14 (m, 5H), 7.23 (br s, 1H), 7.42 (d, J=8.3 Hz, 1H), 8.52 (br s, 1H), 8.68 (s, 1H), 8.75 (s, 1H), 9.80 (brs, 1H).

Example 14

7-(2-chloro-5-methylphenylamino)-N-(ethylcarbamoyl)-6-[4-(4-fluorophenyl)piperidine-1-carbonyl] pyrazolo[1,5-a]pyrimidine-3-sulfonamide (compound a-14)

Using 7-(2-chloro-5-methylphenylamino)-6-[4-(4-fluorophenyl)piperidine-1-carbonyl]pyrazolo[1,5-a]pyrimidine-3-sulfonamide (0.08 g, 0.147 mmol) obtained in Example 12 step 5 and in the same manner as in Example 7, the title compound (0.056 g, 62%) was obtained.

ESI-MS m/z: 614 (M+H)$^+$; $^1$H-NMR (CDCl$_3$, δ): 1.16 (d, J=7.3 Hz, 3H), 1.35-1.39 (m, 2H), 1.72-1.77 (m, 2H), 2.37 (s, 3H), 2.54-2.61 (m, 1H), 3.21-3.31 (m, 2H), 3.61-3.74 (m, 2H), 4.12-4.32 (m, 2H), 6.70 (br s, 1H), 6.95-7.14 (m, 5H), 7.24-7.26 (m, 1H), 7.42 (d, J=8.9 Hz, 1H), 7.97 (br s, 1H), 8.45 (s, 1H), 8.49 (br s, 1H), 8.56 (s, 1H).

Example 15

N-ethyl-7-(2-chloro-5-methylphenylamino)-6-[4-(4-fluorophenyl)piperidine-1-carbonyl]pyrazolo[1,5-a]pyrimidine-3-sulfonamide (compound a-15)

(Step 1)

Ethyl 7-(2-chloro-5-methylphenylamino)-3-(N-ethylsulfamoyl)pyrazolo[1,5-a]pyrimidine-6-carboxylate Using 7-(2-chloro-5-methylphenylamino)-6-(ethoxycarbonyl)pyrazolo[1,5-a]pyrimidine-3-sulfonic acid (0.72 g, 1.75 mmol) obtained in Example 12 step 2 and ethylamine (2.0 mol/L THF solution; 3.5 mL, 7.01 mmol) instead of tert-butylamine, and in the same manner as in Example 1 step 3, the title compound (0.67 g, 87%) was obtained.

(Step 2)

N-ethyl-7-(2-chloro-5-methylphenylamino)-6-[4-(4-fluorophenyl)piperidine-1-carbonyl]pyrazolo[1,5-a]pyrimidine-3-sulfonamide (compound a-15)

Using ethyl 7-(2-chloro-5-methylphenylamino)-3-(N-ethylsulfamoyl)pyrazolo[1,5-a]pyrimidine-6-carboxylate (0.084 g, 0.205 mmol) obtained in step 1 and 4-(4-fluorophenyl)piperidine (0.030 g, 0.183 mmol) instead of 4-phenylpiperidine, and in the same manner as in Example 1 step 4, the title compound (0.019 g, 16%) was obtained.

ESI-MS m/z: 571 (M+H)$^+$; $^1$H-NMR (CDCl$_3$, δ): 1.17 (t, J=7.3 Hz, 3H), 1.20-1.43 (m, 2H), 1.62-1.80 (m, 2H), 2.37 (s, 3H), 2.52-2.62 (m, 1H), 3.03-3.10 (m, 2H), 3.20-4.40 (m, 4H), 4.97 (br t, J=6.0 Hz, 1H), 6.90-7.27 (m, 6H), 7.37 (d, J=8.3 Hz, 1H), 8.45 (s, 1H), 8.46 (s, 1H), 8.50 (s, 1H).

Example 16

N-ethyl-7-(4-chloro-2-methylphenylamino)-6-[4-(4-fluorophenyl)piperidine-1-carbonyl]pyrazolo[1,5-a]pyrimidine-3-sulfonamide (compound a-16)

(Step 1)

Ethyl 7-(4-chloro-2-methylphenylamino)pyrazolo[1,5-a]pyrimidine-6-carboxylate

Using ethyl 7-hydroxypyrazolo[1,5-a]pyrimidine-6-carboxylate (5.00 g, 24.1 mmol) and 4-chloro-2-methylaniline (5.13 g, 36.2 mmol) instead of 4-fluoro-2-methylaniline, and in the same manner as in Example 1 step 1, the title compound (3.80 g, 48%) was obtained.
(Step 2)

7-(4-chloro-2-methylphenylamino)-6-(ethoxycarbonyl)pyrazolo[1,5-a]pyrimidine-3-sulfonic acid Using ethyl 7-(4-chloro-2-methylphenylamino)pyrazolo[1,5-a]pyrimidine-6-carboxylate (3.80 g, 11.5 mmol) obtained in step 1 and in the same manner as in Example 1 step 2, the title compound (4.58 g, 97%) was obtained.
(Step 3)

Ethyl 7-(4-chloro-2-methylphenylamino)-3-(N-ethylsulfamoyl)pyrazolo[1,5-a]pyrimidine-6-carboxylate Using 7-(4-chloro-2-methylphenylamino)-6-(ethoxycarbonyl)pyrazolo[1,5-a]pyrimidine-3-sulfonic acid (1.00 g, 2.43 mmol) obtained in step 2 and ethylamine (2.0 mol/L THF solution; 4.9 mL, 9.74 mmol) instead of tert-butylamine, and in the same manner as in Example 1 step 3, the title compound (1.01 g, 95%) was obtained.
(Step 4)

N-ethyl-7-(4-chloro-2-methylphenylamino)-6-[4-(4-fluorophenyl)piperidine-1-carbonyl]pyrazolo[1,5-a]pyrimidine-3-sulfonamide (compound a-16)

Using ethyl 7-(4-chloro-2-methylphenylamino)-3-(N-ethylsulfamoyl)pyrazolo[1,5-a]pyrimidine-6-carboxylate (0.33 g, 0.77 mmol) obtained in step 3 and 4-(4-fluorophenyl)piperidine (0.26 g, 1.44 mmol) instead of 4-phenylpiperidine, and in the same manner as in Example 1 step 4, the title compound (0.029 g, 6%) was obtained.
ESI-MS m/z: 569 (M−H)−; $^1$H-NMR (CDCl$_3$, δ): 1.16 (t, J=7.3 Hz, 3H), 1.30-1.50 (m, 2H), 1.72-1.87 (m, 2H), 2.39 (s, 3H), 2.58-2.80 (m, 1H), 3.02-3.12 (m, 2H), 3.25-4.03 (m, 2H), 4.05-4.28 (m, 2H), 4.90 (t, J=5.9 Hz, 1H), 6.95-7.30 (m, 6H), 7.37 (s, 1H), 8.19 (s, 1H), 8.34 (s, 1H), 8.43 (s, 1H).

Example 17

N-[7-(4-fluoro-2-methylphenylamino)-6-(4-phenylpiperidine-1-carbonyl)pyrazolo[1,5-a]pyrimidin-3-ylsulfonyl]acetamide (compound a-17)

7-(4-Fluoro-2-methylphenylamino)-6-(4-phenylpiperidine-1-carbonyl)pyrazolo[1,5-a]pyrimidine-3-sulfonamide (0.098 g, 0.175 mmol) obtained in Example 1 step 5 was dissolved in pyridine (2 mL), 4-(dimethylamino)pyridine (0.023 g, 0.189 mmol) and acetyl chloride (0.25 mL, 3.50 mmol) were added, and the mixture was stirred with heating at 50° C. for 2 hr. 1 mol/L Hydrochloric acid was added dropwise to the reaction mixture, and the mixture was extracted 3 times with chloroform. The combined organic layer was dried over anhydrous magnesium sulfate, and concentrated under reduced pressure. The obtained residue was purified by silica gel column chromatography (chloroform/methanol=9/1) to give the title compound (0.013 g, 14%).
ESI-MS m/z: 551 (M+H)+; $^1$H-NMR (CDCl$_3$, δ): 1.44-1.62 (m, 2H), 1.72-1.91 (m, 2H), 2.10 (s, 3H), 2.40 (s, 3H), 2.56-2.76 (m, 1H), 3.63-4.43 (m, 4H), 6.91-7.04 (m, 1H), 7.04-7.37 (m, 7H), 8.28 (s, 1H), 8.48 (s, 1H), 8.63 (s, 1H), 10.21 (s, 1H).

Example 18

N-{7-(2-chloro-4-methylphenylamino)-6-[4-(4-fluorophenyl)piperidine-1-carbonyl]pyrazolo[1,5-a]pyrimidin-3-ylsulfonyl}propionamide (compound a-18)

(Step 1)

Ethyl 7-(2-chloro-4-methylphenylamino)pyrazolo[1,5-a]pyrimidine-6-carboxylate

Using ethyl 7-hydroxypyrazolo[1,5-a]pyrimidine-6-carboxylate (15.0 g, 72.4 mmol) and 2-chloro-4-methylaniline (20.5 g, 144.7 mmol) instead of 4-fluoro-2-methylaniline, and in the same manner as in Example 1 step 1, the title compound (8.37 g, 35%) was obtained.
(Step 2)

6-ethoxycarbonyl-7-(2-chloro-4-methylphenylamino)pyrazolo[1,5-a]pyrimidine-3-sulfonic acid Using ethyl 7-(2-chloro-4-methylphenylamino)pyrazolo[1,5-a]pyrimidine-6-carboxylate (8.37 g, 25.3 mmol) obtained in step 1 and in the same manner as in Example 1 step 2, the title compound (10.7 g, 100%) was obtained.
(Step 3)

Ethyl 3-(N-tert-butylsulfamoyl)-7-(2-chloro-4-methylphenylamino)pyrazolo[1,5-a]pyrimidine-6-carboxylate Using 6-ethoxycarbonyl-7-(2-chloro-4-methylphenylamino)pyrazolo[1,5-a]pyrimidine-3-sulfonic acid (10.66 g, 25.3 mmol) obtained in step 2 and in the same manner as in Example 1 step 3, the title compound (11.17 g, 95%) was obtained.
(Step 4)

N-tert-butyl-7-(2-chloro-4-methylphenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chloro-4-methylphenylamino)pyrazolo[1,5-a]pyrimidine-6-carboxylate (11.17 g, 24.0 mmol) obtained in step 3 and 4-(4-fluorophenyl)piperidine (5.93 g, 33.09 mmol) instead of 4-phenylpiperidine, and in the same manner as in Example 1 step 4, the title compound (8.33 g, 63%) was obtained.
(Step 5)

7-(2-chloro-4-methylphenylamino)-6-[4-(4-fluorophenyl)piperidine-1-carbonyl]pyrazolo[1,5-a]pyrimidine-3-sulfonamide Using N-tert-butyl-7-(2-chloro-4-methylphenylamino)-6-[4-(4-fluorophenyl)piperidine-1-carbonyl]pyrazolo[1,5-a]pyrimidine-3-sulfonamide (3.80 g, 6.34 mmol) obtained in step 4 and in the same manner as in Example 1 step 5, the title compound (2.22 g, 64%) was obtained.
(Step 6)

N-{7-(2-chloro-4-methylphenylamino)-6-[4-(4-fluorophenyl)piperidine-1-carbonyl]pyrazolo[1,5-a]pyrimidin-3-ylsulfonyl}propionamide (compound a-18)

Using 7-(2-chloro-4-methylphenylamino)-6-[4-(4-fluorophenyl)piperidine-1-carbonyl]pyrazolo[1,5-a]pyrimidine- 3-sulfonamide (0.050 g, 0.092 mmol) obtained in step 5 as a starting material and propionic acid (0.034 mL, 0.460 mmol) instead of cyclopropanecarboxylic acid, and in the same manner as in Example 1 step 6, the title compound (0.052 g, 93%) was obtained.

ESI-MS m/z: 599 (M+H)$^+$; $^1$H-NMR (CDCl$_3$, δ): 1.09 (t, J=7.4 Hz, 3H), 1.31-1.43 (m, 2H), 1.74-1.79 (m, 2H), 2.35 (q, J=7.5 Hz, 2H), 2.39 (s, 3H), 2.56-2.65 (m, 1H), 3.41-3.52 (m, 4H), 6.96-7.29 (m, 6H), 7.36 (s, 1H), 8.44 (s, 1H), 8.53 (s, 1H), 8.65 (s, 1H).

Example 19

N-{7-(2,4-dichlorophenylamino)-6-[4-(4-fluorophenyl)piperidine-1-carbonyl]pyrazolo[1,5-a]pyrimidin-3-ylsulfonyl}propionamide (compound a-19)

(Step 1)

Ethyl 7-(2,4-dichlorophenylamino)pyrazolo[1,5-a]pyrimidine-6-carboxylate

Using ethyl 7-hydroxypyrazolo[1,5-a]pyrimidine-6-carboxylate (7.50 g, 36.2 mmol) and 2,4-dichloroaniline (5.30 g, 32.6 mmol) instead of 4-fluoro-2-methylaniline, and in the same manner as in Example 1 step 1, the title compound (9.09 g, 72%) was obtained.

(Step 2)

6-ethoxycarbonyl-7-(2,4-dichlorophenylamino)pyrazolo[1,5-a]pyrimidine-3-sulfonic acid Using ethyl 7-(2,4-dichlorophenylamino)pyrazolo[1,5-a]pyrimidine-6-carboxylate (9.09 g, 25.9 mmol) obtained in step 1 and in the same manner as in Example 1 step 2, the title compound (8.69 g, 78%) was obtained.

(Step 3)

Ethyl 3-(N-tert-butylsulfamoyl)-7-(2,4-dichlorophenylamino)pyrazolo[1,5-a]pyrimidine-6-carboxylate Using 6-ethoxycarbonyl-7-(2,4-dichlorophenylamino)pyrazolo[1,5-a]pyrimidine-3-sulfonic acid (8.69 g, 20.2 mmol) obtained in step 2 and in the same manner as in Example 1 step 3, the title compound (7.74 g, 79%) was obtained.

(Step 4)

N-tert-butyl-7-(2,4-dichlorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2,4-dichlorophenylamino)pyrazolo[1,5-a]pyrimidine-6-carboxylate (2.98 g, 6.13 mmol) obtained in step 3 and 4-(4-fluorophenyl)piperidine (1.5 g, 8.18 mmol) instead of 4-phenylpiperidine, and in the same manner as in Example 1 step 4, the title compound (1.57 g, 41%) was obtained.

(Step 5)

7-(2,4-dichlorophenylamino)-6-[4-(4-fluorophenyl)piperidine-1-carbonyl]pyrazolo[1,5-a]pyrimidine-3-sulfonamide Using N-tert-butyl-7-(2,4-dichlorophenylamino)-6-[4-(4-fluorophenyl)piperidine-1-carbonyl]pyrazolo[1,5-a]pyrimidine-3-sulfonamide (1.57 g, 2.53 mmol) obtained in step 4 and in the same manner as in Example 1 step 5, the title compound (1.30 g, 91%) was obtained.

(Step 6)

N-{7-(2,4-dichlorophenylamino)-6-[4-(4-fluorophenyl)piperidine-1-carbonyl]pyrazolo[1,5-a]pyrimidin-3-ylsulfonyl}propionamide (compound a-19)

Using 7-(2,4-dichlorophenylamino)-6-[4-(4-fluorophenyl)piperidine-1-carbonyl]pyrazolo[1,5-a]pyrimidine-3-sulfonamide (0.050 g, 0.089 mmol) obtained in step 5 and propionic acid (0.033 mL, 0.444 mmol) instead of cyclopropanecarboxylic acid, and in the same manner as in Example 1 step 6, the title compound (0.034 g, 62%) was obtained.

ESI-MS m/z: 619 (M+H)$^+$; $^1$H-NMR (CDCl$_3$, δ): 1.08 (t, J=7.5 Hz, 3H), 1.37-1.48 (m, 2H), 1.79-1.83 (m, 2H), 2.36 (q, J=7.5 Hz, 2H), 2.61-2.69 (m, 1H), 4.09-4.35 (m, 4H), 6.97-7.13 (m, 4H), 7.32-7.35 (m, 2H), 7.57 (s, 1H), 8.48 (s, 1H), 8.60 (s, 1H), 8.67 (s, 1H), 9.47 (s, 1H).

Example 20

7-(2,4-dichlorophenylamino)-N-(ethylcarbamoyl)-6-[4-(4-fluorophenyl)piperidine-1-carbonyl]pyrazolo[1,5-a]pyrimidine-3-sulfonamide (compound a-20)

Using 7-(2,4-dichlorophenylamino)-6-[4-(4-fluorophenyl)piperidine-1-carbonyl]pyrazolo[1,5-a]pyrimidine-3-sulfonamide (0.050 g, 0.089 mmol) obtained in Example 19 step 5 and in the same manner as in Example 7, the title compound (0.038 g, 67%) was obtained.

ESI-MS m/z: 634 (M+H)$^+$; $^1$H-NMR (CDCl$_3$, δ): 1.15 (t, J=7.3 Hz, 3H), 1.35-1.48 (m, 2H), 1.80-1.84 (m, 2H), 2.62-2.70 (m, 1H), 3.21-3.30 (m, 2H), 4.00-4.11 (m, 4H), 6.66-6.69 (m, 1H), 6.98-7.13 (m, 4H), 7.34-7.36 (m, 2H), 7.55 (d, J=0.7 Hz, 1H), 8.16 (s, 1H), 8.44 (s, 1H), 8.49 (s, 1H), 8.49 (s, 1H).

Example 21

7-(2-chloro-4-fluorophenylamino)-N-(cyclopropylcarbamoyl)-6-[4-(4-fluorophenyl)piperidine-1-carbonyl]pyrazolo[1,5-a]pyrimidine-3-sulfonamide (compound a-21)

(Step 1)

Ethyl 7-(2-chloro-4-fluorophenylamino)pyrazolo[1,5-a]pyrimidine-6-carboxylate

Using ethyl 7-hydroxypyrazolo[1,5-a]pyrimidine-6-carboxylate (5.0 g, 24.1 mmol) and 2-chloro-4-fluoroaniline (2.81 g, 19.3 mmol) instead of 4-fluoro-2-methylaniline, and in the same manner as in Example 1 step 1, the title compound (5.56 g, 69%) was obtained.

(Step 2)

6-ethoxycarbonyl-7-(2-chloro-4-fluorophenylamino)pyrazolo[1,5-a]pyrimidine-3-sulfonic acid Using ethyl 7-(2-chloro-4-fluorophenylamino)pyrazolo[1,5-a]pyrimidine-6-carboxylate (5.55 g, 16.6 mmol) obtained in step 1 and in the same manner as in Example 1 step 2, the title compound (6.09 g, 88%) was obtained.

(Step 3)

Ethyl 3-(N-tert-butylsulfamoyl)-7-(2-chloro-4-fluorophenylamino)pyrazolo[1,5-a]pyrimidine-6-carboxylate Using 6-ethoxycarbonyl-7-(2-chloro-4-fluorophenylamino)pyrazolo[1,5-a]pyrimidine-3-sulfonic acid (6.09 g, 14.7 mmol) obtained in step 2 and in the same manner as in Example 1 step 3, the title compound (4.98 g, 72%) was obtained.

(Step 4)

N-tert-butyl-7-(2-chloro-4-fluorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chloro-4-fluorophenylamino)pyrazolo[1,5-a]pyrimidine-6-carboxylate (4.98 g, 10.60 mmol) obtained in step 3 and 4-(4-fluorophenyl)piperidine (1.43 g, 7.97 mmol) instead of 4-phenylpiperidine, and in the same manner as in Example 1 step 4, the title compound (2.95 g, 93%) was obtained.

(Step 5)

7-(2-chloro-4-fluorophenylamino)-6-[4-(4-fluorophenyl)piperidine-1-carbonyl]pyrazolo[1,5-a]pyrimidine-3-sulfonamide Using N-tert-butyl-7-(2-chloro-4-fluorophenylamino)-6-[4-(4-fluorophenyl)piperidine-1-carbonyl]pyrazolo[1,5-a]pyrimidine-3-sulfonamide (2.95 g, 4.89 mmol) obtained in step 4 and in the same manner as in Example 1 step 5, the title compound (2.24 g, 84%) was obtained.

(Step 6)

7-(2-chloro-4-fluorophenylamino)-N-(cyclopropylcarbamoyl)-6-[4-(4-fluorophenyl)piperidine-1-carbonyl]pyrazolo[1,5-a]pyrimidine-3-sulfonamide (compound a-21)

Using 7-(2-chloro-4-fluorophenylamino)-6-[4-(4-fluorophenyl)piperidine-1-carbonyl]pyrazolo[1,5-a]pyrimidine-3-sulfonamide (0.10 g, 0.18 mmol) obtained in step 5 and cyclopropylisocyanate (0.046 g, 0.549 mmol) instead of ethylisocyanate, and in the same manner as in Example 7, the title compound (0.055 g, 47%) was obtained.

ESI-MS m/z: 630 (M+H)$^+$; $^1$H-NMR (DMSO-d$_6$, δ): 0.28-0.36 (m, 2H), 0.52-0.65 (m, 2H), 1.20-1.90 (m, 4H), 2.20-2.28 (m, 1H), 2.40-2.44 (m, 1H), 2.72-2.78 (m, 1H), 3.00-3.05 (m, 1H), 3.72-4.12 (m, 2H), 6.53-6.55 (m, 1H), 7.05-7.62 (m, 7H), 8.37 (s, 1H), 8.58 (s, 1H), 10.35-10.62 (m, 2H).

Example 22

N-{7-(2,5-dichlorophenylamino)-6-[4-(4-fluorophenyl)piperidine-1-carbonyl]pyrazolo[1,5-a]pyrimidin-3-ylsulfonyl}propionamide (compound a-22)

(Step 1)

Ethyl 7-(2,5-dichlorophenylamino)pyrazolo[1,5-a]pyrimidine-6-carboxylate

Using ethyl 7-hydroxypyrazolo[1,5-a]pyrimidine-6-carboxylate (7.50 g, 36.2 mmol) and 2,5-dichloroaniline (5.30 g, 32.6 mmol) instead of 4-fluoro-2-methylaniline, and in the same manner as in Example 1 step 1, the title compound (8.64 g, 68%) was obtained.

(Step 2)

6-ethoxycarbonyl-7-(2,5-dichlorophenylamino)pyrazolo[1,5-a]pyrimidine-3-sulfonic acid Using ethyl 7-(2,5-dichlorophenylamino)pyrazolo[1,5-a]pyrimidine-6-carboxylate (8.64 g, 24.6 mmol) obtained in step 1 and in the same manner as in Example 1 step 2, the title compound (9.51 g, 90%) was obtained.

(Step 3)

Ethyl 3-(N-tert-butylsulfamoyl)-7-(2,5-dichlorophenylamino)pyrazolo[1,5-a]pyrimidine-6-carboxylate Using 6-ethoxycarbonyl-7-(2,5-dichlorophenylamino)pyrazolo[1,5-a]pyrimidine-3-sulfonic acid (9.51 g, 22.1 mmol) obtained in step 2 and in the same manner as in Example 1 step 3, the title compound (8.52 g, 79%) was obtained.

(Step 4)

N-tert-butyl-7-(2,5-dichlorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2,5-dichlorophenylamino)pyrazolo[1,5-a]pyrimidine-6-carboxylate (2.95 g, 6.06 mmol) obtained in step 3 and 4-(4-fluorophenyl)piperidine (1.5 g, 8.18 mmol) instead of 4-phenylpiperidine, and in the same manner as in Example 1 step 4, the title compound (2.35 g, 70%) was obtained.

(Step 5)

7-(2,5-dichlorophenylamino)-6-[4-(4-fluorophenyl)piperidine-1-carbonyl]pyrazolo[1,5-a]pyrimidine-3-sulfonamide Using N-tert-butyl-7-(2,5-dichlorophenylamino)-6-[4-(4-fluorophenyl)piperidine-1-carbonyl]pyrazolo[1,5-a]pyrimidine-3-sulfonamide (2.35 g, 3.79 mmol) obtained in step 4 and in the same manner as in Example 1 step 5, the title compound (1.56 g, 73%) was obtained.

(Step 6)

N-{7-(2,5-dichlorophenylamino)-6-[4-(4-fluorophenyl)piperidine-1-carbonyl]pyrazolo[1,5-a]pyrimidin-3-ylsulfonyl}propionamide (compound a-22)

Using 7-(2,5-dichlorophenylamino)-6-[4-(4-fluorophenyl)piperidine-1-carbonyl]pyrazolo[1,5-a]pyrimidine-3-sulfonamide (0.050 g, 0.089 mmol) obtained in step 5 and propionic acid (0.033 mL, 0.444 mmol) instead of cyclopropanecarboxylic acid, and in the same manner as in Example 1 step 6, the title compound (0.050 g, 92%) was obtained.

ESI-MS m/z: 619 (M+H)$^+$; $^1$H-NMR (CDCl$_3$, δ): 1.09 (t, J=7.3 Hz, 3H), 1.46-1.56 (m, 2H), 1.81-1.87 (m, 2H), 2.36 (q, J=7.5 Hz, 2H), 2.62-2.70 (m, 1H), 4.23-4.53 (m, 4H), 6.96-7.02 (m, 2H), 7.09-7.14 (m, 2H), 7.26-7.33 (m, 2H), 7.49 (d, J=8.4 Hz, 1H), 8.64 (s, 1H), 8.66 (s, 1H).

Example 23

7-(2,5-dichlorophenylamino)-N-(ethylcarbamoyl)-6-[4-(4-fluorophenyl)piperidine-1-carbonyl]pyrazolo[1,5-a]pyrimidine-3-sulfonamide (compound a-23)

Using 7-(2,5-dichlorophenylamino)-6-[4-(4-fluorophenyl)piperidine-1-carbonyl]pyrazolo[1,5-a]pyrimidine-3-sulfonamide (0.050 g, 0.089 mmol) obtained in Example 22 step 5 and in the same manner as in Example 7, the title compound (0.034 g, 60%) was obtained.

ESI-MS m/z: 634 (M+H)$^+$; $^1$H NMR (CDCl$_3$, δ): 1.15 (t, J=7.3 Hz, 3H), 1.46-1.57 (m, 2H), 1.83-1.88 (m, 2H), 2.63-2.72 (m, 1H), 3.20-3.30 (m, 2H), 3.95-4.30 (m, 4H), 6.60-6.63 (m, 1H), 6.97-7.03 (m, 2H), 7.10-7.15 (m, 2H), 7.26-7.33 (m, 2H), 7.48 (d, J=8.4 Hz, 1H), 8.45 (s, 1H), 8.57 (s, 1H), 8.58 (br s, 1H).

Example 24

N-{7-(2,5-dichlorophenylamino)-6-[4-(4-fluorophenyl)piperidine-1-carbonyl]pyrazolo[1,5-a]pyrimidin-3-ylsulfonyl}acetamide (compound a-24)

Using 7-(2,5-dichlorophenylamino)-6-[4-(4-fluorophenyl)piperidine-1-carbonyl]pyrazolo[1,5-a]pyrimidine-3-sulfonamide (0.07 g, 0.12 mmol) obtained in Example 22 step 5 and acetic acid (0.036 mL, 0.62 mmol) instead of cyclopropanecarboxylic acid, and in the same manner as in Example 1 step 6, the title compound (0.048 g, 64%) was obtained.

ESI-MS m/z: 605 (M+H)$^+$; $^1$H-NMR (DMSO-d$_6$, δ): 1.25-1.83 (m, 4H), 1.93 (s, 3H), 2.22-2.28 (m, 1H), 2.70-2.78 (m, 1H), 3.05-3.10 (m, 1H), 3.84-4.18 (m, 2H), 7.05-7.72 (m, 7H), 8.42 (s, 1H), 8.63 (s, 1H), 10.49 (br s, 1H), 12.17 (br s, 1H).

Example 25

N-{7-(2,5-dichlorophenylamino)-6-[4-(4-fluorophenyl)piperidine-1-carbonyl]pyrazolo[1,5-a]pyrimidin-3-ylsulfonyl}-3-methyloxetane-3-carboxamide (compound a-25)

Using 7-(2,5-dichlorophenylamino)-6-[4-(4-fluorophenyl)piperidine-1-carbonyl]pyrazolo[1,5-a]pyrimidine-3-sulfonamide (0.07 g, 0.12 mmol) obtained in Example 22 step 5 and 3-methyloxetane-3-carboxylic acid (0.072 g, 0.62 mmol) instead of cyclopropanecarboxylic acid, and in the same manner as in Example 1 step 6, the title compound (0.063 g, 76%) was obtained.

ESI-MS m/z: 661 (M+H)$^+$; $^1$H-NMR (DMSO-d$_5$, δ): 1.31-1.80 (m, 4H), 1.46 (s, 3H), 2.22-2.29 (m, 1H), 2.66-2.78 (m, 1H), 3.02-3.11 (m, 1H), 3.87-3.95 (m, 1H), 4.03-4.10 (m, 1H), 4.22 (d, J=6.2 Hz, 2H), 4.63 (d, J=6.2 Hz, 2H), 7.07-7.37 (m, 4H), 7.44 (d, J=8.2 Hz, 1H), 7.59 (d, J=8.4 Hz, 1H), 7.67 (s, 1H), 8.43 (s, 1H), 8.69 (s, 1H), 10.53 (s, 1H), 12.30 (br s, 1H).

Example 26

N-{7-(2,5-dichlorophenylamino)-6-[4-(4-fluorophenyl)piperidine-1-carbonyl]pyrazolo[1,5-a]pyrimidin-3-ylsulfonyl}formamide (compound a-26)

Using 7-(2,5-dichlorophenylamino)-6-[4-(4-fluorophenyl)piperidine-1-carbonyl]pyrazolo[1,5-a]pyrimidine-3-sulfonamide (0.10 g, 0.18 mmol) obtained in Example 22 step 5 and formic acid (0.033 mL, 0.89 mmol) instead of cyclopropanecarboxylic acid, and in the same manner as in Example 1 step 6, the title compound (0.037 g, 34%) was obtained.

ESI-MS m/z: 591 (M+H)$^+$; $^1$H-NMR (DMSO-d$_6$, δ): 1.20-1.80 (m, 4H), 2.23-2.29 (m, 1H), 2.50-2.58 (m, 1H), 2.70-2.74 (m, 1H), 3.05-3.12 (m, 1H), 3.85-4.20 (m, 2H), 7.10-7.75 (m, 7H), 8.47 (s, 1H), 8.70 (s, 1H), 8.82 (br s, 1H), 10.55 (br s, 1H).

Example 27

7-(2,5-dichlorophenylamino)-6-[4-(4-fluorophenyl)piperidine-1-carbonyl]-N-methoxypyrazolo[1,5-a]pyrimidine-3-sulfonamide (compound a-27)

(Step 1)

7-(2,5-dichlorophenylamino)-6-[4-(4-fluorophenyl)piperidine-1-carbonyl]pyrazolo[1,5-a]pyrimidine-3-sulfonic acid Using 6-ethoxycarbonyl-7-(2,5-dichlorophenylamino)pyrazolo[1,5-a]pyrimidine-3-sulfonic acid (0.5 g, 1.16 mmol) obtained in Example 22 step 2 and 4-(4-fluorophenyl)piperidine (1.42 g, 7.94 mmol) instead of 4-phenylpiperidine, and in the same manner as in Example 1 step 4, the title compound (0.57 g, 63%) was obtained.

(Step 2)

7-(2,5-dichlorophenylamino)-6-[4-(4-fluorophenyl)piperidine-1-carbonyl]-N-methoxypyrazolo[1,5-a]pyrimidine-3-sulfonamide (compound a-27)

Using 7-(2,5-dichlorophenylamino)-6-[4-(4-fluorophenyl)piperidine-1-carbonyl]pyrazolo[1,5-a]pyrimidine-3-sulfonic acid (0.15 g, 0.27 mmol) obtained in step 1 and O-methylhydroxylamine hydrochloride (0.089 g, 1.06 mmol) instead of tert-butylamine, and in the same manner as in Example 1 step 3, the title compound (0.069 g, 44%) was obtained.

ESI-MS m/z: 593 (M+H)$^+$; $^1$H-NMR (DMSO-d$_6$, δ): 1.20-1.81 (m, 4H), 2.23-2.29 (m, 1H), 2.68-2.74 (m, 1H), 3.07-3.12 (m, 1H), 3.67 (s, 3H), 3.81-4.20 (m, 2H), 7.10-7.75 (m, 7H), 8.44 (s, 1H), 8.57 (s, 1H), 10.26 (s, 1H), 10.46 (s, 1H).

Example 28

7-(2,5-dichlorophenylamino)-N-ethoxy-6-[4-(4-fluorophenyl)piperidine-1-carbonyl]-pyrazolo[1,5-a]pyrimidine-3-sulfonamide (compound a-28)

Using 7-(2,5-dichlorophenylamino)-6-[4-(4-fluorophenyl)piperidine-1-carbonyl]pyrazolo[1,5-a]pyrimidine-3-sulfonic acid (0.15 g, 0.27 mmol) obtained in Example 27 step 1 and O-ethylhydroxylamine hydrochloride (0.104 g, 1.06 mmol) instead of tert-butylamine, and in the same manner as in Example 1 step 3, the title compound (0.036 g, 22%) was obtained.

ESI-MS m/z: 607 (M+H)$^+$; $^1$H-NMR (DMSO-d$_6$, δ): 1.01 (t, J=7.3 Hz, 3H), 1.20-1.81 (m, 4H), 2.23-2.29 (m, 1H), 2.68-2.74 (m, 1H), 3.07-3.12 (m, 1H), 3.92 (q, J=7.3 Hz, 2H), 3.81-4.20 (m, 2H), 7.10-7.75 (m, 7H), 8.43 (s, 1H), 8.56 (s, 1H), 10.10 (s, 1H), 10.46 (s, 1H).

Example 29

N-{7-(2-chloro-5-trifluoromethylphenylamino)-6-[4-(4-fluorophenyl)piperidine-1-carbonyl]pyrazolo[1,5-a]pyrimidin-3-ylsulfonyl}propionamide (compound a-29)

(Step 1)

Ethyl 7-(2-chloro-5-trifluoromethylphenylamino) pyrazolo[1,5-a]pyrimidine-6-carboxylate Using ethyl 7-hydroxypyrazolo[1,5-a]pyrimidine-6-carboxylate (5.0 g, 24.1 mmol) and 2-chloro-5-trifluoromethylaniline (4.25 g, 21.7 mmol) instead of 4-fluoro-2-methylaniline, and in the same manner as in Example 1 step 1, the title compound (6.49 g, 70%) was obtained.

(Step 2)

6-ethoxycarbonyl-7-(2-chloro-5-trifluoromethylphenylamino)pyrazolo[1,5-a]pyrimidine-3-sulfonic acid Using ethyl 7-(2-chloro-5-trifluoromethylphenylamino) pyrazolo[1,5-a]pyrimidine-6-carboxylate (6.49 g, 16.9 mmol) obtained in step 1 and in the same manner as in Example 1 step 2, the title compound (7.26 g, 93%) was obtained.

(Step 3)

Ethyl 3-(N-tert-butylsulfamoyl)-7-(2-chloro-5-trifluoromethylphenylamino)pyrazolo[1,5-a]pyrimidine-6-carboxylate Using 6-ethoxycarbonyl-7-(2-chloro-5-trifluoromethylphenylamino)pyrazolo[1,5-a]pyrimidine-3-sulfonic acid (7.26 g, 15.6 mmol) obtained in step 2 and in the same manner as in Example 1 step 3, the title compound (5.44 g, 69%) was obtained.

(Step 4)

N-tert-butyl-7-(2-chloro-5-trifluoromethylphenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chloro-5-trifluoromethylphenylamino)pyrazolo[1,5-a]pyrimidine-6-carboxylate (2.87 g, 5.52 mmol) obtained in step 3 and 4-(4-fluorophenyl)piperidine (1.37 g, 7.62 mmol) instead of 4-phenylpiperidine, and in the same manner as in Example 1 step 4, the title compound (2.63 g, 79%) was obtained.

(Step 5)

7-(2-chloro-5-trifluoromethylphenylamino)-6-[4-(4-fluorophenyl)piperidine-1-carbonyl]pyrazolo[1,5-a]pyrimidine-3-sulfonamide Using N-tert-butyl-7-(2-chloro-5-trifluoromethylphenylamino)-6-[4-(4-fluorophenyl)piperidine-1-carbonyl]pyrazolo[1,5-a]pyrimidine-3-sulfonamide (2.63 g, 4.03 mmol) obtained in step 4 and in the same manner as in Example 1 step 5, the title compound (1.30 g, 54%) was obtained.

(Step 6)

N-{7-(2-chloro-5-trifluoromethylphenylamino)-6-[4-(4-fluorophenyl)piperidine-1-carbonyl]pyrazolo[1,5-a]pyrimidin-3-ylsulfonyl}propionamide (compound a-29)

Using 7-(2-chloro-5-trifluoromethylphenylamino)-6-[4-(4-fluorophenyl)piperidine-1-carbonyl]pyrazolo[1,5-a]pyrimidine-3-sulfonamide (0.050 g, 0.084 mmol) obtained in step 5 and propionic acid (0.031 mL, 0.419 mmol) instead of cyclopropanecarboxylic acid, and in the same manner as in Example 1 step 6, the title compound (0.048 g, 87%) was obtained.

ESI-MS m/z: 653 (M+H)$^+$; $^1$H NMR (CDCl$_3$, δ): 1.09 (t, J=7.3 Hz, 3H), 1.42-1.54 (m, 2H), 1.78-1.83 (m, 2H), 2.37 (q, J=7.5 Hz, 2H), 2.59-2.67 (m, 1H), 3.40-3.55 (m, 4H), 6.95-7.01 (m, 2H), 7.07-7.12 (m, 2H), 7.55-7.60 (m, 2H), 7.70 (d, J=8.1 Hz, 1H), 8.67 (s, 1H), 8.85 (s, 1H).

Example 30

7-(2-chloro-5-fluorophenylamino)-N-(ethylcarbamoyl)-6-[4-(4-fluorophenyl)piperidine-1-carbonyl] pyrazolo[1,5-a]pyrimidine-3-sulfonamide (compound a-30)

(Step 1)

Ethyl 7-(2-chloro-5-fluorophenylamino)pyrazolo[1,5-a]pyrimidine-6-carboxylate

Using ethyl 7-hydroxypyrazolo[1,5-a]pyrimidine-6-carboxylate (3.5 g, 16.9 mmol) and 2-chloro-5-fluoroaniline (2.21 g, 15.2 mmol) instead of 4-fluoro-2-methylaniline, and in the same manner as in Example 1 step 1, the title compound (4.27 g, 75%) was obtained.

(Step 2)

6-ethoxycarbonyl-7-(2-chloro-5-fluorophenylamino) pyrazolo[1,5-a]pyrimidine-3-sulfonic acid Using ethyl 7-(2-chloro-5-fluorophenylamino)pyrazolo[1,5-a]pyrimidine-6-carboxylate (4.27 g, 12.8 mmol) obtained in step 1 and in the same manner as in Example 1 step 2, the title compound (4.75 g, 90%) was obtained.

(Step 3)

Ethyl 3-(N-tert-butylsulfamoyl)-7-(2-chloro-5-fluorophenylamino)pyrazolo[1,5-a]pyrimidine-6-carboxylate Using 6-ethoxycarbonyl-7-(2-chloro-5-fluorophenylamino)pyrazolo[1,5-a]pyrimidine-3-sulfonic acid (4.75 g, 11.5 mmol) obtained in step 2 and in the same manner as in Example 1 step 3, the title compound (4.16 g, 77%) was obtained.

(Step 4)

N-tert-butyl-7-(2-chloro-5-fluorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chloro-5-fluorophenylamino)pyrazolo[1,5-a]pyrimidine-6-carboxylate (4.16 g, 8.85 mmol) obtained in step 3 and 4-(4-fluorophenyl)piperidine (2.04 g, 11.4 mmol) instead of 4-phenylpiperidine, and in the same manner as in Example 1 step 4, the title compound (3.54 g, 77%) was obtained.

(Step 5)

7-(2-chloro-5-fluorophenylamino)-6-[4-(4-fluorophenyl)piperidine-1-carbonyl]pyrazolo[1,5-a]pyrimidine-3-sulfonamide Using N-tert-butyl-7-(2-chloro-5-fluorophenylamino)-6-[4-(4-fluorophenyl)piperidine-1-carbonyl]pyrazolo[1,5-a]

pyrimidine-3-sulfonamide (3.54 g, 5.87 mmol) obtained in step 4 and in the same manner as in Example 1 step 5, the title compound (2.71 g, 84%) was obtained.
(Step 6)

7-(2-chloro-5-fluorophenylamino)-N-(ethylcarbamoyl)-6-[4-(4-fluorophenyl)piperidine-1-carbonyl]pyrazolo[1,5-a]pyrimidine-3-sulfonamide (compound a-30)

Using 7-(2-chloro-5-fluorophenylamino)-6-[4-(4-fluorophenyl)piperidine-1-carbonyl]pyrazolo[1,5-a]pyrimidine-3-sulfonamide (0.050 g, 0.091 mmol) obtained in step 5 and in the same manner as in Example 7, the title compound (0.053 g, 93%) was obtained.
ESI-MS m/z: 617 (M+H)$^+$; $^1$H NMR (CDCl$_3$, δ): 1.15 (t, J=7.3 Hz, 3H), 1.42-1.55 (m, 2H), 1.81-1.87 (m, 2H), 2.63-2.72 (m, 1H), 3.21-3.30 (m, 2H), 3.97-4.24 (m, 4H), 6.62-6.65 (m, 1H), 6.97-7.14 (m, 6H), 7.49-7.53 (m, 1H), 8.45 (s, 1H), 8.54 (s, 1H), 8.59 (s, 1H).

Example 31

N-{7-(2-fluoro-5-methylphenylamino)-6-[4-(4-fluorophenyl)piperidine-1-carbonyl]pyrazolo[1,5-a]pyrimidin-3-ylsulfonyl}propionamide (compound a-22)

(Step 1)

Ethyl 7-(2-fluoro-5-methylphenylamino)pyrazolo[1,5-a]pyrimidine-6-carboxylate

Using ethyl 7-hydroxypyrazolo[1,5-a]pyrimidine-6-carboxylate (5.0 g, 24.1 mmol) and 2-fluoro-5-methylaniline (2.43 g, 19.3 mmol) instead of 4-fluoro-2-methylaniline, and in the same manner as in Example 1 step 1, the title compound (3.80 g, 50%) was obtained.
(Step 2)

6-ethoxycarbonyl-7-(2-fluoro-5-methylphenylamino)pyrazolo[1,5-a]pyrimidine-3-sulfonic acid Using ethyl 7-(2-fluoro-5-methylphenylamino)pyrazolo[1,5-a]pyrimidine-6-carboxylate (3.80 g, 12.1 mmol) obtained in step 1 and in the same manner as in Example 1 step 2, the title compound (3.53 g, 74%) was obtained.
(Step 3)

Ethyl 3-(N-tert-butylsulfamoyl)-7-(2-fluoro-5-methylphenylamino)pyrazolo[1,5-a]pyrimidine-6-carboxylate Using 6-ethoxycarbonyl-7-(2-fluoro-5-methylphenylamino)pyrazolo[1,5-a]pyrimidine-3-sulfonic acid (3.53 g, 8.95 mmol) obtained in step 2 and in the same manner as in Example 1 step 3, the title compound (2.59 g, 64%) was obtained.
(Step 4)

N-tert-butyl-7-(2-fluoro-5-methylphenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-fluoro-5-methylphenylamino)pyrazolo[1,5-a]pyrimidine-6-carboxylate (1.29 g, 2.89 mmol) obtained in step 3 and 4-(4-fluorophenyl)piperidine (0.73 g, 4.06 mmol) instead of 4-phenylpiperidine, and in the same manner as in Example 1 step 4, the title compound (1.40 g, 95%) was obtained.
(Step 5)

7-(2-fluoro-5-methylphenylamino)-6-[4-(4-fluorophenyl)piperidine-1-carbonyl]pyrazolo[1,5-a]pyrimidine-3-sulfonamide Using N-tert-butyl-7-(2-fluoro-5-methylphenylamino)-6-[4-(4-fluorophenyl)piperidine-1-carbonyl]pyrazolo[1,5-a]pyrimidine-3-sulfonamide (1.40 g, 2.40 mmol) obtained in step 4 and in the same manner as in Example 1 step 5, the title compound (1.06 g, 84%) was obtained.
(Step 6)

N-{7-(2-fluoro-5-methylphenylamino)-6-[4-(4-fluorophenyl)piperidine-1-carbonyl]pyrazolo[1,5-a]pyrimidin-3-ylsulfonyl}propionamide (compound a-22)

Using 7-(2-fluoro-5-methylphenylamino)-6-[4-(4-fluorophenyl)piperidine-1-carbonyl]pyrazolo[1,5-a]pyrimidine-3-sulfonamide (0.10 g, 0.19 mmol) obtained in step 5 and propionic acid (0.071 mL, 0.95 mmol) instead of cyclopropanecarboxylic acid, and in the same manner as in Example 1 step 6, the title compound (0.032 g, 40%) was obtained.
ESI-MS m/z: 583 (M+H)$^+$; $^1$H-NMR (DMSO-d$_6$, δ): 0.89 (t, J=7.4 Hz, 3H), 1.00-1.78 (m, 4H), 2.05-2.11 (m, 1H), 2.22 (q, J=7.4 Hz, 2H), 2.28 (s, 3H), 2.67-2.72 (m, 1H), 2.92-2.98 (m, 1H), 3.70-4.13 (m, 2H), 7.03-7.35 (m, 7H), 8.38 (s, 1H), 8.62 (s, 1H), 10.39 (s, 1H), 12.11 (br s, 1H).

Example 32

7-(2-fluoro-5-methylphenylamino)-N-(cyclopropylcarbamoyl)-6-[4-(4-fluorophenyl)piperidine-1-carbonyl]pyrazolo[1,5-a]pyrimidine-3-sulfonamide (compound a-32)

Using 7-(2-fluoro-5-methylphenylamino)-6-[4-(4-fluorophenyl)piperidine-1-carbonyl]pyrazolo[1,5-a]pyrimidine-3-sulfonamide (0.10 g, 0.19 mmol) obtained in Example 31 step 5 and cyclopropylisocyanate (0.048 g, 0.57 mmol) instead of ethylisocyanate, and in the same manner as in Example 7, the title compound (0.053 g, 62%) was obtained.
ESI-MS m/z: 610 (M+H)$^+$; $^1$H-NMR (DMSO-d$_6$, δ): 0.31-0.37 (m, 2H), 0.52-0.59 (m, 2H), 1.00-1.78 (m, 4H), 2.04-2.09 (m, 1H), 2.29 (s, 3H), 2.38-2.44 (m, 1H), 2.68-2.72 (m, 1H), 2.92-2.97 (m, 1H), 3.66-4.10 (m, 2H), 6.52-6.57 (m, 1H), 7.04-7.35 (m, 7H), 8.38 (s, 1H), 8.57 (s, 1H), 10.30-10.60 (m, 2H).

Example 33

N-{7-(5-chloro-2-fluorophenylamino)-6-[4-(4-fluorophenyl)piperidine-1-carbonyl]pyrazolo[1,5-a]pyrimidin-3-ylsulfonyl}acetamide (compound a-33)

(Step 1)

Ethyl 7-(5-chloro-2-fluorophenylamino)pyrazolo[1,5-a]pyrimidine-6-carboxylate

Using ethyl 7-hydroxypyrazolo[1,5-a]pyrimidine-6-carboxylate (2.0 g, 9.65 mmol) and 5-chloro-2-fluoroaniline (1.26 g, 8.69 mmol) instead of 4-fluoro-2-methylaniline, and in the same manner as in Example 1 step 1, the title compound (2.07 g, 64%) was obtained.

(Step 2)

6-ethoxycarbonyl-7-(5-chloro-2-fluorophenylamino)pyrazolo[1,5-a]pyrimidine-3-sulfonic acid Using ethyl 7-(5-chloro-2-fluorophenylamino)pyrazolo[1,5-a]pyrimidine-6-carboxylate (2.07 g, 6.18 mmol) obtained in step 1 and in the same manner as in Example 1 step 2, the title compound (2.19 g, 85%) was obtained.
(Step 3)

Ethyl 3-(N-tert-butylsulfamoyl)-7-(5-chloro-2-fluorophenylamino)pyrazolo[1,5-a]pyrimidine-6-carboxylate Using 6-ethoxycarbonyl-7-(5-chloro-2-fluorophenylamino)pyrazolo[1,5-a]pyrimidine-3-sulfonic acid (2.19 g, 5.28 mmol) obtained in step 2 and in the same manner as in Example 1 step 3, the title compound (1.82 g, 73%) was obtained.
(Step 4)

N-tert-butyl-7-(5-chloro-2-fluorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(5-chloro-2-fluorophenylamino)pyrazolo[1,5-a]pyrimidine-6-carboxylate (1.82 g, 3.87 mmol) obtained in step 3 and 4-(4-fluorophenyl)piperidine (0.88 g, 4.89 mmol) instead of 4-phenylpiperidine, and in the same manner as in Example 1 step 4, the title compound (0.92 g, 47%) was obtained.
(Step 5)

7-(5-chloro-2-fluorophenylamino)-6-[4-(4-fluorophenyl)piperidine-1-carbonyl]pyrazolo[1,5-a]pyrimidine-3-sulfonamide Using N-tert-butyl-7-(5-chloro-2-fluorophenylamino)-6-[4-(4-fluorophenyl)piperidine-1-carbonyl]pyrazolo[1,5-a]pyrimidine-3-sulfonamide (0.92 g, 1.53 mmol) obtained in step 4 and in the same manner as in Example 1 step 5, the title compound (0.72 g, 86%) was obtained.
(Step 6)

N-{7-(5-chloro-2-fluorophenylamino)-6-[4-(4-fluorophenyl)piperidine-1-carbonyl]pyrazolo[1,5-a]pyrimidin-3-ylsulfonyl}acetamide (compound a-33)

Using 7-(5-chloro-2-fluorophenylamino)-6-[4-(4-fluorophenyl)piperidine-1-carbonyl]pyrazolo[1,5-a]pyrimidine-3-sulfonamide (0.050 g, 0.091 mmol) obtained in step 5 and acetic acid (0.026 mL, 0.457 mmol) instead of cyclopropanecarboxylic acid, and in the same manner as in Example 1 step 6, the title compound (0.047 g, 87%) was obtained.
ESI-MS m/z: 589 (M+H)$^+$; $^1$H NMR (CDCl$_3$, δ): 1.47-1.55 (m, 2H), 1.85-1.89 (m, 2H), 2.11 (s, 3H), 2.65-2.74 (m, 1H), 3.31-3.60 (m, 4H), 6.98-7.03 (m, 2H), 7.11-7.24 (m, 3H), 7.30-7.36 (m, 2H), 8.48 (s, 1H), 8.59 (s, 1H), 8.64 (s, 1H).

Example 34

7-(5-chloro-2-fluorophenylamino)-N-(ethylcarbamoyl)-6-[4-(4-fluorophenyl)piperidine-1-carbonyl]pyrazolo[1,5-a]pyrimidine-3-sulfonamide (compound a-34)

Using 7-(5-chloro-2-fluorophenylamino)-6-[4-(4-fluorophenyl)piperidine-1-carbonyl]pyrazolo[1,5-a]pyrimidine-3-sulfonamide (0.050 g, 0.091 mmol) obtained in Example 33 step 5 and in the same manner as in Example 7, the title compound (0.039 g, 68%) was obtained.
ESI-MS m/z: 618 (M+H)$^+$; $^1$H NMR (CDCl$_3$, δ): 1.14 (t, J=7.2 Hz, 3H), 1.48-1.60 (m, 2H), 1.86-1.90 (m, 2H), 2.66-2.75 (m, 1H), 3.20-3.29 (m, 2H), 3.98-4.30 (m, 4H), 6.63-6.66 (m, 1H), 6.98-7.04 (m, 2H), 7.11-7.20 (m, 3H), 7.29-7.34 (m, 2H), 8.44 (s, 1H), 8.51 (s, 1H), 8.53 (s, 1H).

Example 35

N-{7-(2,5-difluorophenylamino)-6-[4-(4-fluorophenyl)piperidine-1-carbonyl]pyrazolo[1,5-a]pyrimidin-3-ylsulfonyl}acetamide (compound a-35)

(Step 1)

Ethyl 7-(2,5-difluorophenylamino)pyrazolo[1,5-a]pyrimidine-6-carboxylate

Using ethyl 7-hydroxypyrazolo[1,5-a]pyrimidine-6-carboxylate (2.0 g, 9.65 mmol) and 2,5-difluoroaniline (1.12 g, 8.69 mmol) instead of 4-fluoro-2-methylaniline, and in the same manner as in Example 1 step 1, the title compound (1.72 g, 56%) was obtained.
(Step 2)

6-ethoxycarbonyl-7-(2,5-difluorophenylamino)pyrazolo[1,5-a]pyrimidine-3-sulfonic acid Using ethyl 7-(2,5-difluorophenylamino)pyrazolo[1,5-a]pyrimidine-6-carboxylate (1.72 g, 5.40 mmol) obtained in step 1 and in the same manner as in Example 1 step 2, the title compound (1.86 g, 86%) was obtained.
(Step 3)

Ethyl 3-(N-tert-butylsulfamoyl)-7-(2,5-difluorophenylamino)pyrazolo[1,5-a]pyrimidine-6-carboxylate Using 6-ethoxycarbonyl-7-(2,5-difluorophenylamino)pyrazolo[1,5-a]pyrimidine-3-sulfonic acid (1.86 g, 4.67 mmol) obtained in step 2 and in the same manner as in Example 1 step 3, the title compound (1.38 g, 65%) was obtained.
(Step 4)

N-tert-butyl-7-(2,5-difluorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2,5-difluorophenylamino)pyrazolo[1,5-a]pyrimidine-6-carboxylate (1.38 g, 3.04 mmol) obtained in step 3 and 4-(4-fluorophenyl)piperidine (0.70 g, 3.88 mmol) instead of 4-phenylpiperidine, and in the same manner as in Example 1 step 4, the title compound (0.64 g, 43%) was obtained.
(Step 5)

7-(2,5-difluorophenylamino)-6-[4-(4-fluorophenyl)piperidine-1-carbonyl]pyrazolo[1,5-a]pyrimidine-3-sulfonamide Using N-tert-butyl-7-(2,5-difluorophenylamino)-6-[4-(4-fluorophenyl)piperidine-1-carbonyl]pyrazolo[1,5-a]pyrimidine-3-sulfonamide (0.64 g, 1.10 mmol) obtained in step 4 and in the same manner as in Example 1 step 5, the title compound (0.51 g, 88%) was obtained.

(Step 6)

N-{7-(2,5-difluorophenylamino)-6-[4-(4-fluorophenyl)piperidine-1-carbonyl]pyrazolo[1,5-a]pyrimidin-3-ylsulfonyl}acetamide (compound a-35)

Using 7-(2,5-difluorophenylamino)-6-[4-(4-fluorophenyl)piperidine-1-carbonyl]pyrazolo[1,5-a]pyrimidine-3-sulfonamide (0.050 g, 0.094 mmol) obtained in step 5 and acetic acid (0.027 mL, 0.471 mmol) instead of cyclopropanecarboxylic acid, and in the same manner as in Example 1 step 6, the title compound (0.046 g, 84%) was obtained.
ESI-MS m/z: 573 (M+H)$^+$; $^1$H NMR (CDCl$_3$, δ): 1.48-1.58 (m, 2H), 1.83-1.89 (m, 2H), 2.10 (s, 3H), 2.65-2.73 (m, 1H), 3.38-3.56 (m, 4H), 6.91-7.24 (m, 7H), 8.49 (s, 1H), 8.56 (s, 1H), 8.64 (s, 1H).

Example 36

N-{7-(2,5-difluorophenylamino)-6-[4-(4-fluorophenyl)piperidine-1-carbonyl]pyrazolo[1,5-a]pyrimidin-3-ylsulfonyl}propionamide (compound a-36)

Using 7-(2,5-difluorophenylamino)-6-[4-(4-fluorophenyl)piperidine-1-carbonyl]pyrazolo[1,5-a]pyrimidine-3-sulfonamide (0.050 g, 0.094 mmol) obtained in Example 35 step 5 and propionic acid (0.035 mL, 0.471 mmol) instead of cyclopropanecarboxylic acid, and in the same manner as in Example 1 step 6, the title compound (0.048 g, 86%) was obtained.
ESI-MS m/z: 587 (M+H)$^+$; $^1$H NMR (CDCl$_3$, δ): 1.08 (t, J=7.5 Hz, 3H), 1.47-1.58 (m, 2H), 1.83-1.87 (m, 2H), 2.35 (q, J=7.5 Hz, 2H), 2.64-2.73 (m, 1H), 3.41-3.58 (m, 4H), 6.91-7.24 (m, 7H), 8.55 (s, 1H), 8.65 (s, 1H).

Example 37

7-(2-chloro-5-methylphenylamino)-N-(2,2-difluorocyclopropylcarbamoyl)-6-[4-(4-fluorophenyl)piperidine-1-carbonyl]pyrazolo[1,5-a]pyrimidine-3-sulfonamide (compound a-37)

2,2-Difluorocyclopropanecarboxylic acid (0.067 g, 0.552 mmol) was dissolved in 1,4-dioxane (2 mL), diphenylphosphoryl azide (0.182 g, 0.66 mmol) and triethylamine (0.092 mL, 0.66 mmol) were added, and the mixture was heated under reflux for 2 hr. The reaction solution was allowed to cool, 7-(2-chloro-5-methylphenylamino)-6-[4-(4-fluorophenyl)piperidine-1-carbonyl]pyrazolo[1,5-a]pyrimidine-3-sulfonamide (0.10 g, 0.18 mmol) obtained in Example 12 step 5 and potassium carbonate were added, and the mixture was stirred at 50° C. for 3 hr. 5% Aqueous citric acid solution was added to quench the reaction, and the precipitated crystals were collected by filtration. The obtained crystals were purified by silica gel column chromatography (chloroform/methanol=10/1) to give the title compound (0.014 g, 11%).
ESI-MS m/z: 662 (M+H)$^+$; $^1$H-NMR (DMSO-d$_6$, δ): 0.96-1.90 (m, 5H), 2.07-2.12 (m, 1H), 2.31 (s, 3H), 2.68-2.72 (m, 1H), 2.94-2.98 (m, 1H), 3.13-3.15 (m, 1H), 3.76-3.80 (m, 1H), 3.98-4.01 (m, 1H), 6.84 (br s, 1H), 7.03-7.52 (m, 8H), 8.37 (s, 1H), 8.59 (s, 1H), 10.34 (s, 1H), 10.87 (br s, 1H).

Example 38

N-{7-(2,3-dichlorophenylamino)-6-[4-(4-fluorophenyl)piperidine-1-carbonyl]pyrazolo[1,5-a]pyrimidin-3-ylsulfonyl}acetamide (compound a-38)

(Step 1)

Ethyl 7-(2,3-dichlorophenylamino)pyrazolo[1,5-a]pyrimidine-6-carboxylate

Using ethyl 7-hydroxypyrazolo[1,5-a]pyrimidine-6-carboxylate (5.0 g, 24.1 mmol) and 2,3-dichloroaniline (3.13 g, 19.3 mmol) instead of 4-fluoro-2-methylaniline, and in the same manner as in Example 1 step 1, the title compound (5.36 g, 63%) was obtained.
(Step 2)

6-ethoxycarbonyl-7-(2,3-dichlorophenylamino)pyrazolo[1,5-a]pyrimidine-3-sulfonic acid Using ethyl 7-(2,3-dichlorophenylamino)pyrazolo[1,5-a]pyrimidine-6-carboxylate (5.36 g, 15.3 mmol) obtained in step 1 and in the same manner as in Example 1 step 2, the title compound (6.00 g, 91%) was obtained.
(Step 3)

Ethyl 3-(N-tert-butylsulfamoyl)-7-(2,3-dichlorophenylamino)pyrazolo[1,5-a]pyrimidine-6-carboxylate Using 6-ethoxycarbonyl-7-(2,3-dichlorophenylamino)pyrazolo[1,5-a]pyrimidine-3-sulfonic acid (6.00 g, 13.9 mmol) obtained in step 2 and in the same manner as in Example 1 step 3, the title compound (4.56 g, 67%) was obtained.
(Step 4)

N-tert-butyl-7-(2,3-dichlorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2,3-dichlorophenylamino)pyrazolo[1,5-a]pyrimidine-6-carboxylate (4.56 g, 9.38 mmol) obtained in step 3 and 4-(4-fluorophenyl)piperidine (2.31 g, 12.9 mmol) instead of 4-phenylpiperidine, and in the same manner as in Example 1 step 4, the title compound (4.52 g, 85%) was obtained.
(Step 5)

7-(2,3-dichlorophenylamino)-6-[4-(4-fluorophenyl)piperidine-1-carbonyl]pyrazolo[1,5-a]pyrimidine-3-sulfonamide Using N-tert-butyl-7-(2,3-dichlorophenylamino)-6-[4-(4-fluorophenyl)piperidine-1-carbonyl]pyrazolo[1,5-a]pyrimidine-3-sulfonamide (4.52 g, 7.30 mmol) obtained in step 4 and in the same manner as in Example 1 step 5, the title compound (2.78 g, 68%) was obtained.
(Step 6)

N-{7-(2,3-dichlorophenylamino)-6-[4-(4-fluorophenyl)piperidine-1-carbonyl]pyrazolo[1,5-a]pyrimidin-3-ylsulfonyl}acetamide (compound a-38)
Using 7-(2,3-dichlorophenylamino)-6-[4-(4-fluorophenyl)piperidine-1-carbonyl]pyrazolo[1,5-a]pyrimidine-3-sulfonamide (0.050 g, 0.089 mmol) obtained in step 5 and acetic acid (0.025 mL, 0.444 mmol) instead of cyclopropanecarboxylic acid, and in the same manner as in Example 1 step 6, the title compound (0.033 g, 61%) was obtained.
ESI-MS m/z: 605 (M+H)$^+$; $^1$H NMR (CDCl$_3$, δ): 1.27-1.42 (m, 2H), 1.76-1.81 (m, 2H), 2.12 (s, 3H), 2.56-2.65 (m, 1H), 3.61-3.93 (m, 4H), 6.91-7.11 (m, 4H), 7.28-7.36 (m, 2H), 7.50 (dd, J=7.3, 2.2 Hz, 1H), 8.61 (s, 1H), 8.62 (s, 1H), 8.66 (s, 1H), 9.50 (s, 1H).

Example 39

7-(3,4-dichlorophenylamino)-N-(ethylcarbamoyl)-6-[4-(4-fluorophenyl)piperidine-1-carbonyl]pyrazolo[1,5-a]pyrimidine-3-sulfonamide (compound a-39)

(Step 1)

Ethyl 7-(3,4-dichlorophenylamino)pyrazolo[1,5-a]pyrimidine-6-carboxylate

Using ethyl 7-hydroxypyrazolo[1,5-a]pyrimidine-6-carboxylate (3.0 g, 14.5 mmol) and 3,4-dichloroaniline (1.88 g, 11.6 mmol) instead of 4-fluoro-2-methylaniline, and in the same manner as in Example 1 step 1, the title compound (2.90 g, 57%) was obtained.
(Step 2)

6-ethoxycarbonyl-7-(3,4-dichlorophenylamino)pyrazolo[1,5-a]pyrimidine-3-sulfonic acid Using ethyl 7-(3,4-dichlorophenylamino)pyrazolo[1,5-a]pyrimidine-6-carboxylate (2.90 g, 8.26 mmol) obtained in step 1 and in the same manner as in Example 1 step 2, the title compound (3.36 g, 94%) was obtained.
(Step 3)

Ethyl 3-(N-tert-butylsulfamoyl)-7-(3,4-dichlorophenylamino)pyrazolo[1,5-a]pyrimidine-6-carboxylate Using 6-ethoxycarbonyl-7-(3,4-dichlorophenylamino)pyrazolo[1,5-a]pyrimidine-3-sulfonic acid (3.36 g, 7.79 mmol) obtained in step 2 and in the same manner as in Example 1 step 3, the title compound (1.40 g, 37%) was obtained.
(Step 4)

N-tert-butyl-7-(3,4-dichlorophenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(3,4-dichlorophenylamino)pyrazolo[1,5-a]pyrimidine-6-carboxylate (1.40 g, 2.88 mmol) obtained in step 3 and 4-(4-fluorophenyl)piperidine (0.48 g, 2.65 mmol) instead of 4-phenylpiperidine, and in the same manner as in Example 1 step 4, the title compound (0.35 g, 32%) was obtained.
(Step 5)

7-(3,4-dichlorophenylamino)-6-[4-(4-fluorophenyl)piperidine-1-carbonyl]pyrazolo[1,5-a]pyrimidine-3-sulfonamide Using N-tert-butyl-7-(3,4-dichlorophenylamino)-6-[4-(4-fluorophenyl)piperidine-1-carbonyl]pyrazolo[1,5-a]pyrimidine-3-sulfonamide (0.35 g, 0.569 mmol) obtained in step 4 and in the same manner as in Example 1 step 5, the title compound (0.25 g, 79%) was obtained.
(Step 6)

7-(3,4-dichlorophenylamino)-N-(ethylcarbamoyl)-6-[4-(4-fluorophenyl)piperidine-1-carbonyl]pyrazolo[1,5-a]pyrimidine-3-sulfonamide (compound a-39)

Using 7-(3,4-dichlorophenylamino)-6-[4-(4-fluorophenyl)piperidine-1-carbonyl]pyrazolo[1,5-a]pyrimidine-3-sulfonamide (0.050 g, 0.089 mmol) obtained in step 5 and in the same manner as in Example 7, the title compound (0.054 g, 60%) was obtained.
ESI-MS m/z: 631 (M+H)$^+$; $^1$H NMR (CDCl$_3$, δ): 0.85-0.88 (m, 2H), 0.94-0.98 (m, 2H), 1.38-1.55 (m, 2H), 1.56-1.63 (m, 1H), 1.81-1.89 (m, 2H), 2.64-2.73 (m, 1H), 4.22-4.38 (m, 4H), 6.98-7.04 (m, 2H), 7.12-7.21 (m, 3H), 7.41 (d, J=2.6 Hz, 1H), 7.54 (d, J=8.4 Hz, 1H), 8.41 (s, 1H), 8.59 (s, 1H).

Example 40

N-{7-(2-chloro-4-fluoro-5-methylphenylamino)-6-[4-(4-fluorophenyl)piperidine-1-carbonyl]pyrazolo[1,5-a]pyrimidin-3-ylsulfonyl}propionamide (compound a-40)

(Step 1)

Ethyl 7-(2-chloro-4-fluoro-5-methylphenylamino)pyrazolo[1,5-a]pyrimidine-6-carboxylate Using ethyl 7-hydroxypyrazolo[1,5-a]pyrimidine-6-carboxylate (4.35 g, 21.0 mmol) and 2-chloro-4-fluoro-5-methylaniline (3.02 g, 18.9 mmol) instead of 4-fluoro-2-methylaniline, and in the same manner as in Example 1 step 1, the title compound (5.54 g, 76%) was obtained.
(Step 2)

6-ethoxycarbonyl-7-(2-chloro-4-fluoro-5-methylphenylamino)pyrazolo[1,5-a]pyrimidine-3-sulfonic acid Using ethyl 7-(2-chloro-4-fluoro-5-methylphenylamino)pyrazolo[1,5-a]pyrimidine-6-carboxylate (5.54 g, 15.9 mmol) obtained in step 1 and in the same manner as in Example 1 step 2, the title compound (5.92 g, 87%) was obtained.
(Step 3)

Ethyl 3-(N-tert-butylsulfamoyl)-7-(2-chloro-4-fluoro-5-methylphenylamino)pyrazolo[1,5-a]pyrimidine-6-carboxylate Using 6-ethoxycarbonyl-7-(2-chloro-4-fluoro-5-methylphenylamino)pyrazolo[1,5-a]pyrimidine-3-sulfonic acid (5.92 g, 13.8 mmol) obtained in step 2 and in the same manner as in Example 1 step 3, the title compound (5.14 g, 77%) was obtained.
(Step 4)

N-tert-butyl-7-(2-chloro-4-fluoro-5-methylphenylamino)-6-[4-(4-fluorophenyl)piperidine-1-carbonyl]pyrazolo[1,5-a]pyrimidine-3-sulfonamide Using ethyl 3-(N-tert-butylsulfamoyl)-7-(2-chloro-4-fluoro-5-methylphenylamino)pyrazolo[1,5-a]pyrimidine-6-carboxylate (2.94 g, 6.07 mmol) obtained in step 3 and 4-(4-fluorophenyl)piperidine (1.18 g, 6.58 mmol) instead of 4-phenylpiperidine, and in the same manner as in Example 1 step 4, the title compound (0.90 g, 33%) was obtained.
(Step 5)

7-(2-chloro-4-fluoro-5-methylphenylamino)-6-[4-(4-fluorophenyl)piperidine-1-carbonyl]pyrazolo[1,5-a]pyrimidine-3-sulfonamide Using N-tert-butyl-7-(2-chloro-4-fluoro-5-methylphenylamino)-6-[4-(4-fluorophenyl)piperidine-1-carbonyl]pyrazolo[1,5-a]pyrimidine-3-sulfonamide (0.90 g, 1.45 mmol) obtained in step 4 and in the same manner as in Example 1 step 5, the title compound (0.59 g, 73%) was obtained.
(Step 6)

N-{7-(2-chloro-4-fluoro-5-methylphenylamino)-6-[4-(4-fluorophenyl)piperidine-1-carbonyl]pyrazolo[1,5-a]pyrimidin-3-ylsulfonyl}propionamide (compound a-40)

Using 7-(2-chloro-4-fluoro-5-methylphenylamino)-6-[4-(4-fluorophenyl)piperidine-1-carbonyl]pyrazolo[1,5-a]pyrimidine-3-sulfonamide (0.050 g, 0.089 mmol) obtained in step 5 and propionic acid (0.033 mL, 0.446 mmol) instead of cyclopropanecarboxylic acid, and in the same manner as in Example 1 step 6, the title compound (0.052 g, 95%) was obtained.
ESI-MS m/z: 617 (M+H)$^+$; $^1$H NMR (CDCl$_3$, δ): 1.09 (t, J=7.5 Hz, 3H), 1.34-1.47 (m, 2H), 1.76-1.82 (m, 2H), 2.29 (d, J=1.5 Hz, 3H), 2.35 (q, J=7.5 Hz, 2H), 2.57-2.67 (m, 1H), 3.46-3.83 (m, 4H), 6.96-7.02 (m, 2H), 7.07-7.11 (m, 2H), 7.22-7.29 (m, 2H), 8.57 (s, 1H), 8.65 (s, 1H).

Example 41

N-{7-(2-chloro-4-fluoro-5-methylphenylamino)-6-[4-(4-fluorophenyl)piperidine-1-carbonyl]pyrazolo[1,5-a]pyrimidin-3-ylsulfonyl}cyclopropanecarboxamide (compound a-41)

Using 7-(2-chloro-4-fluoro-5-methylphenylamino)-6-[4-(4-fluorophenyl)piperidine-1-carbonyl]pyrazolo[1,5-a]pyrimidine-3-sulfonamide (0.050 g, 0.089 mmol) obtained in Example 40 step 5 and in the same manner as in Example 1 step 6, the title compound (0.054 g, 96%) was obtained.
ESI-MS m/z: 629 (M+H)$^+$; $^1$H NMR (CDCl$_3$, δ): 0.83-0.90 (m, 2H), 1.00-1.05 (m, 2H), 1.37-1.48 (m, 2H), 1.56-1.63 (m, 1H), 1.77-1.82 (m, 2H), 2.29 (d, J=1.5 Hz, 3H), 2.58-2.67 (m, 1H), 3.43-3.64 (m, 4H), 6.96-7.02 (m, 2H), 7.07-7.11 (m, 2H), 7.21-7.29 (m, 2H), 8.59 (s, 1H), 8.62 (s, 1H).

Example 42

7-(2-chloro-4-fluoro-5-methylphenylamino)-N-(ethylcarbamoyl)-6-[4-(4-fluorophenyl)piperidine-1-carbonyl]pyrazolo[1,5-a]pyrimidine-3-sulfonamide (compound a-42)

Using 7-(2-chloro-4-fluoro-5-methylphenylamino)-6-[4-(4-fluorophenyl)piperidine-1-carbonyl]pyrazolo[1,5-a]pyrimidine-3-sulfonamide (0.050 g, 0.089 mmol) obtained in Example 40 step 5 and in the same manner as in Example 7, the title compound (0.050 g, 88%) was obtained.
ESI-MS m/z: 632 (M+H)$^+$; $^1$H NMR (CDCl$_3$, δ): 1.16 (t, J=7.1 Hz, 3H), 1.35-1.47 (m, 2H), 1.77-1.83 (m, 2H), 2.30 (d, J=1.5 Hz, 3H), 2.58-2.67 (m, 1H), 3.20-3.31 (m, 2H), 4.07-4.24 (m, 4H), 6.70 (s, 1H), 6.97-7.03 (m, 2H), 7.07-7.12 (m, 2H), 7.20-7.32 (m, 2H), 8.00 (s, 1H), 8.39 (s, 1H), 8.43 (s, 1H), 8.48 (s, 1H).

Example 43

7-(4-fluoro-2-methylphenylamino)-N-(ethylcarbamoyl)-6-[3H-spiro(isobenzofuran-1,4'-piperidine)-1-carbonyl]pyrazolo[1,5-a]pyrimidine-3-sulfonamide (compound a-43)

(Step 1)

N-tert-butyl-7-(4-fluoro-2-methylphenylamino)-6-[3H-spiro(isobenzofuran-1,4'-piperidine)-1-carbonyl]pyrazolo[1,5-a]pyrimidine-3-sulfonamide Using ethyl 3-(N-tert-butylsulfamoyl)-7-(4-fluoro-2-methylphenylamino)pyrazolo[1,5-a]pyrimidine-6-carboxylate (1.70 g, 3.78 mmol) obtained in Example 1 step 3 and 3H-spiroisobenzofuran-1,4'-piperidine hydrochloride (0.83 g, 3.67 mmol) instead of 4-phenylpiperidine, and in the same manner as in Example 1 step 4, the title compound (0.44 g, 30%) was obtained.
(Step 2)

7-(4-fluoro-2-methylphenylamino)-6-[3H-spiro(isobenzofuran-1,4'-piperidine)-1-carbonyl]pyrazolo[1,5-a]pyrimidine-3-sulfonamide Using N-tert-butyl-7-(4-fluoro-2-methylphenylamino)-6-[3H-spiro(isobenzofuran-1,4'-piperidine)-1-carbonyl]piperidine-1-carbonyl]pyrazolo[1,5-a]pyrimidine-3-sulfonamide (0.44 g, 0.742 mmol) obtained in step 1 and in the same manner as in Example 1 step 5, the title compound (0.25 g, 63%) was obtained.
(Step 3)

N-(ethylcarbamoyl)-7-(4-fluoro-2-methylphenylamino)-6-[3H-spiro(isobenzofuran-1,4'-piperidine)-1-carbonyl]pyrazolo[1,5-a]pyrimidine-3-sulfonamide (compound a-43)

Using 7-(4-fluoro-2-methylphenylamino)-6-[3H-spiro(isobenzofuran-1,4'-piperidine)-1-carbonyl]pyrazolo[1,5-a]pyrimidine-3-sulfonamide (0.05 g, 0.093 mmol) obtained in step 2 and in the same manner as in Example 7, the title compound (0.034 g, 60%) was obtained.
ESI-MS m/z: 608 (M+H)$^+$; $^1$H-NMR (CDCl$_3$, δ): 1.15 (t, J=7.6 Hz, 3H), 1.40-1.75 (m, 4H), 2.39 (s, 3H), 3.21-3.21 (m, 2H), 3.40-4.30 (m, 4H), 5.07 (s, 2H), 6.66 (br s, 1H), 6.97-7.12 (m, 3H), 7.18-7.32 (m, 5H), 8.23 (br s, 1H), 8.41 (s, 1H), 8.43 (s, 1H).

Example 44

7-(2-chloro-5-methylphenylamino)-N-(ethylcarbamoyl)-6-[3H-spiro(isobenzofuran-1,4'-piperidine)-1-carbonyl]pyrazolo[1,5-a]pyrimidine-3-sulfonamide (compound a-44)

(Step 1)

N-tert-butyl-7-(2-chloro-5-methylphenylamino)-6-[3H-spiro(isobenzofuran-1,4'-piperidine)-1-carbonyl]pyrazolo[1,5-a]pyrimidine-3-sulfonamide Using ethyl 3-(N-tert-butylsulfamoyl)-7-(2-chloro-5-methylphenylamino)pyrazolo[1,5-a]pyrimidine-6-carboxylate (1.00 g, 2.14 mmol) obtained in Example 12 step 3 and 3H-spiroisobenzofuran-1,4'-piperidine hydrochloride (0.50 g, 2.23 mmol) instead of 4-phenylpiperidine, and in the same manner as in Example 1 step 4, the title compound (0.41 g, 31%) was obtained.
(Step 2)

7-(2-chloro-5-methylphenylamino)-6-[3H-spiro(isobenzofuran-1,4'-piperidine)-1-carbonyl]pyrazolo[1,5-a]pyrimidine-3-sulfonamide Using N-tert-butyl-7-(2-chloro-5-methylphenylamino)-6-[3H-spiro(isobenzofuran-1,4'-piperidine)-1-carbonyl]piperidine-1-carbonyl]pyrazolo[1,5-a]pyrimidine-3-sulfonamide (0.41 g, 0.673 mmol) obtained in step 1 and in the same manner as in Example 1 step 5, the title compound (0.20 g, 54%) was obtained.
(Step 3)

7-(2-chloro-5-methylphenylamino)-N-(ethylcarbamoyl)-6-[3H-spiro(isobenzofuran-1,4'-piperidine)-1-carbonyl]pyrazolo[1,5-a]pyrimidine-3-sulfonamide (compound a-44)

Using 7-(2-chloro-5-methylphenylamino)-6-[3H-spiro(isobenzofuran-1,4'-piperidine)-1-carbonyl]pyrazolo[1,5-a]pyrimidine-3-sulfonamide (0.085 g, 0.162 mmol) obtained in step 2 and in the same manner as in Example 7, the title compound (0.077 g, 48%) was obtained.

ESI-MS m/z: 624 (M+H)⁺; ¹H-NMR (CDCl₃, δ): 1.15 (t, J=7.2 Hz, 3H), 1.40-1.80 (m, 4H), 2.38 (s, 3H), 2.40-4.30 (m, 4H), 3.26 (m, 2H), 5.03 (s, 2H), 6.66 (br-s, 1H), 6.99-7.35 (m, 6H), 7.46 (d, J=8.1 Hz, 1H), 8.45 (s, 1H), 8.50 (br s, 1H), 8.60 (s, 1H).

Example 45

N-ethyl-7-(2-chloro-5-methylphenylamino)-6-[3H-spiro(isobenzofuran-1,4'-piperidine)-1-carbonyl]pyrazolo[1,5-a]pyrimidine-3-sulfonamide (compound a-45)

Using ethyl 7-(2-chloro-5-methylphenylamino)-3-(N-ethylsulfamoyl)pyrazolo[1,5-a]pyrimidine-6-carboxylate (0.156 g, 0.359 mmol) obtained in Example 15 step 1 and 3H-spiroisobenzofuran-1,4'-piperidine hydrochloride (0.083 g, 0.366 mmol) instead of 4-phenylpiperidine, and in the same manner as in Example 1 step 4, the title compound (0.035 g, 17%) was obtained.
ESI-MS m/z: 581 (M+H)⁺; ¹H-NMR (DMSO-d₆, δ): 1.02 (t, J=7.3 Hz, 3H), 1.45-2.00 (m, 4H), 2.33 (s, 3H), 2.93-2.99 (m, 2H), 3.00-3.10 (m, 1H), 3.10-3.40 (m, 1H), 3.58-4.00 (m, 2H), 4.99 (s, 2H), 7.12-7.38 (m, 5H), 7.38-7.52 (m, 2H), 8.41 (s, 1H), 8.48 (s, 1H), 10.21 (br s, 1H).

Example 46

N-{7-(4-chloro-2-methylphenylamino)-6-[3H-spiro(isobenzofuran-1,4'-piperidine)-1-carbonyl]pyrazolo[1,5-a]pyrimidin-3-ylsulfonyl}cyclopropanecarboxyamide (compound a-46)

(Step 1)

Ethyl 3-(N-tert-butylsulfamoyl)-7-(4-chloro-2-methylphenylamino)-pyrazolo[1,5-a]pyrimidine-6-carboxylate Using 7-(4-chloro-2-methylphenylamino)-6-(ethoxycarbonyl)pyrazolo[1,5-a]pyrimidine-3-sulfonic acid (3.59 g, 8.74 mmol) obtained in Example 16 step 2 and in the same manner as in Example 1 step 3, the title compound (3.96 g, 99%) was obtained.
(Step 2)

N-tert-butyl-7-(4-chloro-2-methylphenylamino)-6-[3H-spiro(isobenzofuran-1,4'-piperidine)-1-carbonyl]pyrazolo[1,5-a]pyrimidine-3-sulfonamide Using ethyl 3-(N-tert-butylsulfamoyl)-7-(4-chloro-2-methylphenylamino)pyrazolo[1,5-a]pyrimidine-6-carboxylate (1.21 g, 2.59 mmol) obtained in step 1 and 3H-spiroisobenzofuran-1,4'-piperidine (0.696 g, 3.08 mmol) instead of 4-phenylpiperidine, and in the same manner as in Example 1 step 4, the title compound (0.974 g, 62%) was obtained.
(Step 3)

7-(4-chloro-2-methylphenylamino)-6-[3H-spiro(isobenzofuran-1,4'-piperidine)-1-carbonyl]pyrazolo[1,5-a]pyrimidine-3-sulfonamide Using N-tert-butyl-7-(4-chloro-2-methylphenylamino)-6-[3H-spiro(isobenzofuran-1,4'-piperidine)-1-carbonyl]pyrazolo[1,5-a]pyrimidine-3-sulfonamide (0.85 g, 1.42 mmol) obtained in step 2 and in the same manner as in Example 1 step 5, the title compound (0.42 g, 55%) was obtained.
(Step 4)

N-{7-(4-chloro-2-methylphenylamino)-6-[3H-spiro(isobenzofuran-1,4'-piperidine)-1-carbonyl]pyrazolo[1,5-a]pyrimidin-3-ylsulfonyl}cyclopropanecarboxyamide (compound a-46)

Using 7-(4-chloro-2-methylphenylamino)-6-[3H-spiro(isobenzofuran-1,4'-piperidine)-1-carbonyl]pyrazolo[1,5-a]pyrimidine-3-sulfonamide (0.080 g, 0.145 mmol) obtained in step 3 and in the same manner as in Example 1 step 6, the title compound (0.080 g, 89%) was obtained.
ESI-MS m/z: 619 (M−H)⁻; ¹H-NMR (CDCl₃, δ): 0.83-0.87 (m, 2H), 1.01-1.04 (m, 2H), 1.39-1.95 (m, 5H), 2.39 (s, 3H), 3.15-4.30 (m, 4H), 5.07 (s, 2H), 7.05-7.40 (m, 7H), 8.26 (br s, 1H), 8.58 (s, 1H), 8.62 (s, 1H).

Example 47

7-(4-chloro-2-methylphenylamino)-N-(ethylcarbamoyl)-6-[3H-spiro(isobenzofuran-1,4'-piperidine)-1-carbonyl]pyrazolo[1,5-a]pyrimidine-3-sulfonamide (compound a-47)

Using 7-(4-chloro-2-methylphenylamino)-6-[3H-spiro(isobenzofuran-1,4'-piperidine)-1-carbonyl]pyrazolo[1,5-a]pyrimidine-3-sulfonamide (0.080 g, 0.145 mmol) obtained in Example 46 step 3 and in the same manner as in Example 7, the title compound (0.090 g, 99%) was obtained.
ESI-MS m/z: 622 (M−H)⁻; ¹H-NMR (CDCl₃, δ): 1.14 (t, J=7.2 Hz, 3H), 1.90-2.10 (m, 4H), 2.39 (s, 3H), 3.20-3.26 (m, 2H), 3.40-4.30 (m, 4H), 5.07 (s, 2H), 6.65 (br s, 1H), 7.07-7.43 (m, 7H), 8.28 (br s, 1H), 8.42 (s, 1H), 8.43 (s, 1H).

Example 48

N-{7-(2-fluoro-4-methylphenylamino)-6-[3H-spiro(isobenzofuran-1,4'-piperidine)-1-carbonyl]pyrazolo[1,5-a]pyrimidin-3-ylsulfonyl}propionamide (compound a-48)

(Step 1)

Ethyl 7-(2-fluoro-4-methylphenylamino)pyrazolo[1,5-a]pyrimidine-6-carboxylate

Using ethyl 7-hydroxypyrazolo[1,5-a]pyrimidine-6-carboxylate (5.0 g, 24.1 mmol) and 4-methyl-2-fluoroaniline (6.04 g, 48.3 mmol) instead of 4-fluoro-2-methylaniline, and in the same manner as in Example 1 step 1, the title compound (4.05 g, 53%) was obtained.
(Step 2)

6-ethoxycarbonyl-7-(2-fluoro-4-methylphenylamino)pyrazolo[1,5-a]pyrimidine-3-sulfonic acid Using ethyl 7-(2-fluoro-4-methylphenylamino)pyrazolo[1,5-a]pyrimidine-6-carboxylate (4.05 g, 12.9 mmol) obtained in step 1 and in the same manner as in Example 1 step 2, the title compound (5.31 g, 100%) was obtained.

(Step 3)

Ethyl 3-(N-tert-butylsulfamoyl)-7-(2-fluoro-4-methylphenylamino)pyrazolo[1,5-a]pyrimidine-6-carboxylate Using 6-ethoxycarbonyl-7-(2-fluoro-4-methylphenylamino)pyrazolo[1,5-a]pyrimidine-3-sulfonic acid (5.31 g, 12.9 mmol) obtained in step 2 and in the same manner as in Example 1 step 3, the title compound (5.88 g, 99%) was obtained.

(Step 4)

N-tert-butyl-7-(2-fluoro-4-methylphenylamino)-6-[3H-spiro(isobenzofuran-1,4'-piperidine)-1-carbonyl]pyrazolo[1,5-a]pyrimidine-3-sulfonamide Using ethyl 3-(N-tert-butylsulfamoyl)-7-(2-fluoro-4-methylphenylamino)pyrazolo[1,5-a]pyrimidine-6-carboxylate (2.94 g, 6.4 mmol) obtained in step 3 and 3H-spiroisobenzofuran-1,4'-piperidine hydrochloride (1.61 g, 7.12 mmol) instead of 4-phenylpiperidine, and in the same manner as in Example 1 step 4, the title compound (1.03 g, 25%) was obtained.

(Step 5)

7-(2-fluoro-4-methylphenylamino)-6-[3H-spiro(isobenzofuran-1,4'-piperidine)-1-carbonyl]pyrazolo[1,5-a]pyrimidine-3-sulfonamide Using N-tert-butyl-7-(2-fluoro-4-methylphenylamino)-6-[3H-spiro(isobenzofuran-1,4'-piperidine)-1-carbonyl]pyrazolo[1,5-a]pyrimidine-3-sulfonamide (1.03 g, 1.74 mmol) obtained in step 4 and in the same manner as in Example 1 step 5, the title compound (0.81 g, 87%) was obtained.

(Step 6)

N-{7-(2-fluoro-4-methylphenylamino)-6-[3H-spiro(isobenzofuran-1,4'-piperidine)-1-carbonyl]pyrazolo[1,5-a]pyrimidin-3-ylsulfonyl}propionamide (compound a-48)

Using 7-(2-fluoro-4-methylphenylamino)-6-[3H-spiro(isobenzofuran-1,4'-piperidine)-1-carbonyl]pyrazolo[1,5-a]pyrimidine-3-sulfonamide (0.10 g, 0.19 mmol) obtained in step 5 and propionic acid (0.069 mL, 0.93 mmol) instead of cyclopropanecarboxylic acid, and in the same manner as in Example 1 step 6, the title compound (0.057 g, 52%) was obtained.

ESI-MS m/z: 593 (M+H)$^+$; $^1$H-NMR (DMSO-d$_6$, δ): 0.88 (t, J=7.4 Hz, 3H), 1.40-2.00 (m, 4H), 2.23 (q, J=7.4 Hz, 2H), 2.36 (s, 3H), 2.40 (m, 1H), 3.10-3.96 (m, 2H), 5.01 (s, 2H), 6.37 (br t, J=5.3 Hz, 1H), 7.05-7.40 (m, 7H), 8.42 (s, 1H), 8.62 (s, 1H), 10.37 (s, 1H), 12.11 (s, 1H).

Example 49

7-(2-fluoro-4-methylphenylamino)-N-(ethylcarbamoyl)-6-[3H-spiro(isobenzofuran-1,4'-piperidine)-1-carbonyl]pyrazolo[1,5-a]pyrimidine-3-sulfonamide (compound a-49)

Using 7-(2-fluoro-4-methylphenylamino)-6-[3H-spiro(isobenzofuran-1,4'-piperidine)-1-carbonyl]pyrazolo[1,5-a]pyrimidine-3-sulfonamide (0.08 g, 0.15 mmol) obtained in Example 48 step 5 and in the same manner as in Example 7, the title compound (0.037 g, 40%) was obtained.

ESI-MS m/z: 608 (M+H)$^+$; $^1$H-NMR (DMSO-d$_6$, δ): 0.94 (t, J=7.3 Hz, 3H), 1.40-2.00 (m, 4H), 2.36 (s, 3H), 2.92-3.02 (m, 2H), 3.09-3.40 (m, 2H), 3.60-3.95 (m, 2H), 5.00 (s, 2H), 6.37 (br t, J=5.3 Hz, 1H), 7.05 (d, J=7.6 Hz, 1H), 7.16 (d, J=10.6 Hz, 1H), 7.22-7.38 (m, 5H), 8.41 (s, 1H), 8.57 (s, 1H), 10.34 (s, 1H), 10.58 (s, 1H).

Example 50

N-{7-(2-chloro-4-fluorophenylamino)-6-[3H-spiro(isobenzofuran-1,4'-piperidine)-1-carbonyl]pyrazolo[1,5-a]pyrimidin-3-ylsulfonyl}propionamide (compound a-50)

(Step 1)

N-tert-butyl-7-(2-chloro-4-fluorophenylamino)-6-[3H-spiro(isobenzofuran-1,4'-piperidine)-1-carbonyl]pyrazolo[1,5-a]pyrimidine-3-sulfonamide Using ethyl 3-(N-tert-butylsulfamoyl)-7-(2-chloro-4-fluorophenylamino)pyrazolo[1,5-a]pyrimidine-6-carboxylate (2.50 g, 5.30 mmol) obtained in Example 21 step 3 and 3H-spiroisobenzofuran-1,4'-piperidine hydrochloride (1.84 g, 8.16 mmol) instead of 4-phenylpiperidine, and in the same manner as in Example 1 step 4, the title compound (2.45 g, 79%) was obtained.

(Step 2)

7-(2-chloro-4-fluorophenylamino)-6-[3H-spiro(isobenzofuran-1,4'-piperidine)-1-carbonyl]pyrazolo[1,5-a]pyrimidine-3-sulfonamide Using N-tert-butyl-7-(2-chloro-4-fluorophenylamino)-6-[3H-spiro(isobenzofuran-1,4'-piperidine)-1-carbonyl]piperidine-1-carbonyl]pyrazolo[1,5-a]pyrimidine-3-sulfonamide (2.45 g, 4.00 mmol) obtained in step 1 and in the same manner as in Example 1 step 5, the title compound (1.72 g, 77%) was obtained.

(Step 3)

N-{7-(2-chloro-4-fluorophenylamino)-6-[3H-spiro(isobenzofuran-1,4'-piperidine)-1-carbonyl]pyrazolo[1,5-a]pyrimidin-3-ylsulfonyl}propionamide (compound a-50)

Using 7-(2-chloro-4-fluorophenylamino)-6-[3H-spiro(isobenzofuran-1,4'-piperidine)-1-carbonyl]pyrazolo[1,5-a]pyrimidine-3-sulfonamide (0.10 g, 0.18 mmol) obtained in step 2 and propionic acid (0.067 mL, 0.90 mmol) instead of cyclopropanecarboxylic acid, and in the same manner as in Example 1 step 6, the title compound (0.085 g, 77%) was obtained.

ESI-MS m/z: 613 (M+H)$^+$; $^1$H-NMR (DMSO-d$_6$, δ): 0.89 (t, J=7.4 Hz, 3H), 1.45-2.05 (m, 4H), 2.22 (q, J=7.4 Hz, 2H), 2.43-2.47 (m, 1H), 3.26-3.30 (m, 1H), 3.58-4.00 (m, 2H), 5.01 (s, 2H), 7.23-7.72 (m, 7H), 8.44 (s, 1H), 8.62 (s, 1H), 10.42 (br s, 1H).

Example 51

N-{7-(2-fluoro-5-methylphenylamino)-6-[3H-spiro(isobenzofuran-1,4'-piperidine)-1-carbonyl]pyrazolo[1,5-a]pyrimidin-3-ylsulfonyl}propionamide (compound a-51)

(Step 1)

N-tert-butyl-7-(2-fluoro-5-methylphenylamino)-6-[3H-spiro(isobenzofuran-1,4'-piperidine)-1-carbonyl]pyrazolo[1,5-a]pyrimidine-3-sulfonamide Using ethyl 3-(N-tert-butylsulfamoyl)-7-(2-fluoro-5-methylphenylamino)pyrazolo[1,5-a]pyrimidine-6-carboxylate (1.29 g, 5.76 mmol) obtained in Example 31 step 3 and 3H-spiroisobenzofuran-1,4'-piperidine hydrochloride (0.92 g, 4.06 mmol) instead of 4-phenylpiperidine, and in the same manner as in Example 1 step 4, the title compound (1.40 g, 81%) was obtained.
(Step 2)

7-(2-fluoro-5-methylphenylamino)-6-[3H-spiro (isobenzofuran-1,4'-piperidine)-1-carbonyl]pyrazolo [1,5-a]pyrimidine-3-sulfonamide Using N-tert-butyl-7-(2-fluoro-5-methylphenylamino)-6-[3H-spiro(isobenzofuran-1,4'-piperidine)-1-carbonyl]piperidine-1-carbonyl]pyrazolo[1,5-a]pyrimidine-3-sulfonamide (1.40 g, 2.36 mmol) obtained in step 1 and in the same manner as in Example 1 step 5, the title compound (0.84 g, 67%) was obtained.
(Step 3)

N-{7-(2-fluoro-5-methylphenylamino)-6-[3H-spiro (isobenzofuran-1,4'-piperidine)-1-carbonyl]pyrazolo [1,5-a]pyrimidin-3-ylsulfonyl}propionamide (compound a-51)

Using 7-(2-fluoro-5-methylphenylamino)-6-[3H-spiro (isobenzofuran-1,4'-piperidine)-1-carbonyl]pyrazolo[1,5-a] pyrimidine-3-sulfonamide (0.10 g, 0.19 mmol) obtained in step 2 and propionic acid (0.069 mL, 0.93 mmol) instead of cyclopropanecarboxylic acid, and in the same manner as in Example 1 step 6, the title compound (0.041 g, 59%) was obtained.
ESI-MS m/z: 583 (M+H)$^+$; $^1$H-NMR (DMSO-$d_6$, δ): 0.89 (t, J=7.6 Hz, 3H), 1.42-2.00 (m, 4H), 2.22 (q, J=6.6 Hz, 2H), 2.24-2.30 (m, 1H), 2.32 (s, 3H), 3.10-4.00 (m, 3H), 5.00 (s, 2H), 7.14-7.35 (m, 7H), 8.44 (s, 1H), 8.63 (s, 1H), 10.42 (s, 1H), 12.12 (s, 1H).

Example 52

N-{7-(2-fluoro-5-methylphenylamino)-6-[3H-spiro (isobenzofuran-1,4'-piperidine)-1-carbonyl]pyrazolo [1,5-a]pyrimidin-3-ylsulfonyl}cyclopropanecarboxyamide (compound a-52)

Using 7-(2-fluoro-5-methylphenylamino)-6-[3H-spiro (isobenzofuran-1,4'-piperidine)-1-carbonyl]pyrazolo[1,5-a] pyrimidine-3-sulfonamide (0.10 g, 0.19 mmol) obtained in Example 51 step 2 and in the same manner as in Example 1 step 6, the title compound (0.040 g, 57%) was obtained.
ESI-MS m/z: 605 (M+H)$^+$; $^1$H-NMR (DMSO-$d_5$, δ): 0.60-0.86 (m, 4H), 1.45-1.98 (m, 5H), 2.31 (s, 3H), 2.32-2.36 (m, 1H), 3.10-3.96 (m, 3H), 5.00 (s, 2H), 7.12-7.40 (m, 7H), 8.44 (s, 1H), 8.58 (s, 1H), 10.41 (br s, 1H), 12.42 (br s, 1H).

Example 53

N-{7-(2,5-dichlorophenylamino)-6-[3H-spiro (isobenzofuran-1,4'-piperidine)-1-carbonyl]pyrazolo [1,5-a]pyrimidin-3-ylsulfonyl}propionamide (compound a-53)

(Step 1)

N-tert-butyl-7-(2,5-dichlorophenylamino)-6-[3H-spiro(isobenzofuran-1,4'-piperidine)-1-carbonyl] pyrazolo[1,5-a]pyrimidine-3-sulfonamide Using ethyl 3-(N-tert-butylsulfamoyl)-7-(2,5-dichlorophenylamino)pyrazolo[1,5-a]pyrimidine-6-carboxylate (2.36 g, 4.89 mmol) obtained in Example 22 step 3 and 3H-spiroisobenzofuran-1,4'-piperidine hydrochloride (1.48 g, 6.55 mmol) instead of 4-phenylpiperidine, and in the same manner as in Example 1 step 4, the title compound (1.95 g, 71%) was obtained.
(Step 2)

7-(2,5-dichlorophenylamino)-6-[3H-spiro(isobenzo-furan-1,4'-piperidine)-1-carbonyl]pyrazolo[1,5-a] pyrimidine-3-sulfonamide Using N-tert-butyl-7-(2,5-dichlorophenylamino)-6-[3H-spiro(isobenzofuran-1,4'-piperidine)-1-carbonyl]piperidine-1-carbonyl]pyrazolo[1,5-a]pyrimidine-3-sulfonamide (1.95 g, 3.10 mmol) obtained in step 1 and in the same manner as in Example 1 step 5, the title compound (1.68 g, 95%) was obtained.
(Step 3)

N-{7-(2,5-dichlorophenylamino)-6-[3H-spiro (isobenzofuran-1,4'-piperidine)-1-carbonyl]pyrazolo [1,5-a]pyrimidin-3-ylsulfonyl}propionamide (compound a-53)

Using 7-(2,5-dichlorophenylamino)-6-[3H-spiro(isobenzofuran-1,4'-piperidine)-1-carbonyl]pyrazolo[1,5-a]pyrimidine-3-sulfonamide (0.05 g, 0.087 mmol) obtained in step 2 and propionic acid (0.032 mL, 0.436 mmol) instead of cyclopropanecarboxylic acid, and in the same manner as in Example 1 step 6, the title compound (0.027 g, 49%) was obtained.
ESI-MS m/z: 629 (M H)$^+$; $^1$H NMR (CDCl$_3$, δ): 1.09 (t, J=7.3 Hz, 3H), 1.68-1.82 (m, 4H), 2.38 (q, J=7.5 Hz, 2H), 3.32-3.68 (m, 4H), 5.06 (s, 2H), 7.08-7.11 (m, 1H), 7.19-7.37 (m, 5H), 7.53 (d, J=8.4 Hz, 1H), 8.52 (s, 1H), 8.68 (s, 1H), 8.85 (s, 1H), 9.55 (s, 1H).

Example 54

N-{7-(2,5-dichlorophenylamino)-6-[3H-spiro (isobenzofuran-1,4'-piperidine)-1-carbonyl]pyrazolo [1,5-a]pyrimidin-3-ylsulfonyl}cyclopropanecarboxamide (compound a-54)

Using 7-(2,5-dichlorophenylamino)-6-[3H-spiro(isobenzofuran-1,4'-piperidine)-1-carbonyl]pyrazolo[1,5-a]pyrimidine-3-sulfonamide (0.05 g, 0.087 mmol) obtained in Example 53 step 2 and in the same manner as in Example 1 step 6, the title compound (0.022 g, 39%) was obtained.
ESI-MS m/z: 641 (M+H)$^+$; $^1$H NMR (CDCl$_3$, δ): 0.84-0.90 (m, 2H), 1.00-1.05 (m, 2H), 1.65-1.70 (m, 1H), 1.73-1.81 (m, 4H), 3.39-3.63 (m, 4H), 5.06 (s, 2H), 7.08-7.11 (m, 1H), 7.20-7.36 (m, 5H), 7.52 (d, J=8.4 Hz, 1H), 8.50 (s, 1H), 8.65 (s, 1H), 8.88 (s, 1H), 9.59 (s, 1H).

Example 55

N-{7-(2-chloro-5-methylphenylamino)-6-[3H-spiro (isobenzofuran-1,4'-piperidine)-1-carbonyl]pyrazolo [1,5-a]pyrimidin-3-ylsulfonyl}acetamide (compound a-55)

Using 7-(2-chloro-5-methylphenylamino)-6-[3H-spiro (isobenzofuran-1,4'-piperidine)-1-carbonyl]pyrazolo[1,5-a] pyrimidine-3-sulfonamide (0.07 g, 0.13 mmol) obtained in Example 44 step 2 and acetic acid (0.036 mL, 0.63 mmol)

instead of cyclopropanecarboxylic acid, and in the same manner as in Example 1 step 6, the title compound (0.027 g, 39%) was obtained.

ESI-MS m/z: 595 (M+H)$^+$; $^1$H-NMR (DMSO-d$_6$, δ): 1.60-1.90 (m, 3H), 1.92 (s, 3H), 2.33 (s, 3H), 2.28-2.32 (m, 1H), 3.15-3.50 (m, 2H), 3.65-73 (m, 1H), 3.88-3.92 (m, 1H), 4.99 (s, 2H), 7.20-7.40 (m, 7H), 7.46 (d, J=8.4 Hz, 1H), 8.43 (s, 1H), 8.61 (s, 1H), 10.36 (br s, 1H).

Example 56

N-{7-(2-chloro-5-methylphenylamino)-6-[3H-spiro (isobenzofuran-1,4'-piperidine)-1-carbonyl]pyrazolo [1,5-a]pyrimidin-3-ylsulfonyl}propionamide (compound a-56)

Using 7-(2-chloro-5-methylphenylamino)-6-[3H-spiro (isobenzofuran-1,4'-piperidine)-1-carbonyl]pyrazolo[1,5-a] pyrimidine-3-sulfonamide (0.07 g, 0.13 mmol) obtained in Example 44 step 2 and propionic acid (0.047 mL, 0.63 mmol) instead of cyclopropanecarboxylic acid, and in the same manner as in Example 1 step 6, the title compound (0.052 g, 67%) was obtained.

ESI-MS m/z: 609 (M+H)$^+$; $^1$H-NMR (DMSO-d$_6$, δ): 0.89 (t, J=7.3% Hz, 3H), 1.42-2.00 (m, 4H), 2.23 (q, J=7.4 Hz, 2H), 2.33 (s, 3H), 3.15-3.40 (m, 2H), 3.62-3.67 (m, 1H), 3.88-3.92 (m, 1H), 4.99 (s, 2H), 7.18-7.36 (m, 6H), 7.47 (d, J=8.4 Hz, 1H), 8.44 (s, 1H), 8.63 (s, 1H), 10.37 (s, 1H), 12.13 (s, 1H).

Example 57

N-{7-(2-chloro-5-methylphenylamino)-6-[3H-spiro (isobenzofuran-1,4'-piperidine)-1-carbonyl]pyrazolo [1,5-a]pyrimidin-3-ylsulfonyl}cyclobutanecarboxamide (compound a-57)

Using 7-(2-chloro-5-methylphenylamino)-6-[3H-spiro (isobenzofuran-1,4'-piperidine)-1-carbonyl]pyrazolo[1,5-a] pyrimidine-3-sulfonamide (0.07 g, 0.13 mmol) obtained in Example 44 step 2 and cyclobutanecarboxylic acid (0.061 mL, 0.63 mmol) instead of cyclopropanecarboxylic acid, and in the same manner as in Example 1 step 6, the title compound (0.049 g, 61%) was obtained.

ESI-MS m/z: 634 (M+H)$^+$; $^1$H-NMR (DMSO-d$_6$, δ): 1.46-2.15 (m, 11H), 2.33 (s, 3H), 3.05-3.35 (m, 2H), 3.62-3.67 (m, 1H), 3.88-3.90 (m, 1H), 4.99 (s, 2H), 7.19-7.36 (m, 6H), 7.47 (d, J=8.2 Hz, 1H), 8.42 (s, 1H), 8.63 (s, 1H), 10.37 (s, 1H), 12.01 (s, 1H).

Example 58

N-{7-(2-chloro-5-methylphenylamino)-6-[3H-spiro (isobenzofuran-1,4'-piperidine)-1-carbonyl]pyrazolo [1,5-a]pyrimidin-3-ylsulfonyl}-3-methyloxetane-3-carboxamide (compound a-58)

Using 7-(2-chloro-5-methylphenylamino)-6-[3H-spiro (isobenzofuran-1,4'-piperidine)-1-carbonyl]pyrazolo[1,5-a] pyrimidine-3-sulfonamide (0.07 g, 0.13 mmol) obtained in Example 44 step 2 and 3-methyloxetane-3-carboxylic acid (0.073 g, 0.63 mmol) instead of cyclopropanecarboxylic acid, and in the same manner as in Example 1 step 6, the title compound (0.050 g, 61%) was obtained.

ESI-MS m/z: 651 (M+H)$^+$; $^1$H-NMR (DMSO-d$_6$, δ): 1.38-1.98 (m, 4H), 1.46 (s, 3H), 2.33 (s, 3H), 3.20-3.24 (m, 1H), 3.50-3.73 (m, 2H), 3.86-3.90 (m, 1H), 4.20-4.24 (m, 2H), 4.62-4.66 (m, 2H), 4.99 (s, 2H), 7.18-7.39 (m, 6H), 7.47 (d, J=8.2 Hz, 1H), 8.45 (s, 1H), 8.68 (s, 1H), 10.40 (s, 1H), 12.30 (br s, 1H).

Example 59

7-(2-fluoro-4-methylphenylamino)-N-(2,2-difluoro-cyclopropylcarbamoyl)-6-[3H-spiro(isobenzofuran-1,4'-piperidine)-1-carbonyl]pyrazolo[1,5-a]pyrimidine-3-sulfonamide (compound a-59)

Using 7-(2-fluoro-4-methylphenylamino)-6-[3H-spiro (isobenzofuran-1,4'-piperidine)-1-carbonyl]pyrazolo[1,5-a] pyrimidine-3-sulfonamide (0.1 g, 0.18 mmol) obtained in Example 48 step 5 and in the same manner as in Example 37, the title compound (0.012 g, 10%) was obtained.

ESI-MS m/z: 672 (M+H)$^+$; $^1$H-NMR (DMSO-d$_6$, δ): 0.75-1.30 (m, 1H), 1.34-1.47 (m, 1H), 1.50-1.85 (m, 6H), 2.38 (s, 3H), 3.00-4.25 (m, 3H), 5.03 (s, 2H), 6.90-7.35 (m, 8H), 7.47 (d, J=8.2 Hz, 1H), 8.50 (s, 1H), 8.52 (br s, 1H), 8.76 (br s, 1H).

Example 60

N-{7-(2-chloro-5-methylphenylamino)-6-[6-(4-fluorophenyl)-2,6-diazaspiro[3,3]heptane-2-carbonyl] pyrazolo[1,5-a]pyrimidin-3-ylsulfonyl}propionamide (compound a-60)

(Step 1)

N-tert-butyl-7-(2-chloro-5-methylphenylamino)-6-[6-(4-fluorophenyl)-2,6-diazaspiro[3,3]heptane-2-carbonyl]pyrazolo[1,5-a]pyrimidine-3-sulfonamide Using ethyl 3-(N-tert-butylsulfamoyl)-7-(2-chloro-5-methylphenylamino)pyrazolo[1,5-a]pyrimidine-6-carboxylate (0.184 g, 0.395 mmol) obtained in Example 12 step 3 and 2-(4-fluorophenyl)-2,6-diazospiro[3,3]heptane (0.065 g, 0.336 mmol) obtained in Reference Example 1 instead of 4-phenylpiperidine, and in the same manner as in Example 1 step 4, the title compound (0.104 g, 50%) was obtained.

(Step 2)

7-(2-chloro-5-methylphenylamino)-6-[6-(4-fluorophenyl)-2,6-diazaspiro[3,3]heptane-2-carbonyl] pyrazolo[1,5-a]pyrimidine-3-sulfonamide Using N-tert-butyl-7-(2-chloro-5-methylphenylamino)-6-[6-(4-fluorophenyl)-2,6-diazaspiro[3,3]heptane-2-carbonyl] piperidine-1-carbonyl]pyrazolo[1,5-a]pyrimidine-3-sulfonamide (0.104 g, 0.169 mmol) obtained in step 1 and in the same manner as in Example 1 step 5, the title compound (0.058 g, 62%) was obtained.

(Step 3)

N-{7-(2-chloro-5-methylphenylamino)-6-[6-(4-fluorophenyl)-2,6-diazaspiro[3,3]heptane-2-carbonyl] pyrazolo[1,5-a]pyrimidin-3-ylsulfonyl}propionamide (compound a-60)

Using 7-(2-chloro-5-methylphenylamino)-6-[6-(4-fluorophenyl)-2,6-diazaspiro[3,3]heptane-2-carbonyl]pyrazolo [1,5-a]pyrimidine-3-sulfonamide (0.045 g, 0.081 mmol) obtained in step 2 and propionic acid (0.030 mL, 0.405 mmol)

instead of cyclopropanecarboxylic acid, and in the same manner as in Example 1 step 6, the title compound (0.027 g, 54%) was obtained.

ESI-MS m/z: 612 (M+H)+; 1H NMR (CDCl3, δ): 1.07 (t, J=7.5 Hz, 3H), 2.30 (q, J=7.6 Hz, 2H), 2.36 (s, 3H), 3.85 (s, 7H), 4.10-4.22 (m, 1H), 6.36-6.40 (m, 2H), 6.89-6.96 (m, 2H), 7.11-7.13 (m, 2H), 7.15 (s, 1H), 7.43 (d, J=8.1 Hz, 1H), 8.52 (s, 1H), 8.58 (s, 1H).

Example 61

7-(2-chloro-5-methylphenylamino)-N-(ethylcarbamoyl)-6-[6-(4-fluorophenyl)-2,6-diazaspiro[3,3]heptane-2-carbonyl]pyrazolo[1,5-a]pyrimidine-3-sulfonamide (compound a-61)

Using 7-(2-chloro-5-methylphenylamino)-6-[6-(4-fluorophenyl)-2,6-diazaspiro[3,3]heptane-2-carbonyl]pyrazolo[1,5-a]pyrimidine-3-sulfonamide (0.010 g, 0.018 mmol) obtained in Example 60 step 2 and in the same manner as in Example 7, the title compound (0.0073 g, 65%) was obtained.

ESI-MS m/z: 627 (M+H)+; 1H NMR (CDCl3, δ): 1.14 (t, J=7.1 Hz, 3H), 2.36 (s, 3H), 2.52-2.69 (m, 2H), 3.21-3.29 (m, 2H), 3.86-4.37 (m, 6H), 6.41-6.45 (m, 2H), 6.70 (s, 1H), 6.91-6.97 (m, 2H), 7.11-7.14 (m, 2H), 7.39 (d, J=8.8 Hz, 1H), 8.32 (s, 1H), 8.59 (s, 1H), 9.89 (s, 1H).

Reference Example 1

2-(4-fluorophenyl)-2,6-diazaspiro[3,3]heptane (Step 1)

tert-butyl 6-(4-fluorophenyl)-2,6-diazaspiro[3,3]heptane-2-carboxylate 6-(tert-Butoxycarbonyl)-6-aza-2-azospiro[3,3]heptane oxalate (Organic Letters, vol. 10, page 3525, 2008; 0.050 g, 0.103 mmol) was dissolved in toluene (2.5 mL), 1-bromo-4-fluorobenzene (0.036 g, 0.206 mmol), tris(dibenzylideneacetone)dipalladium(0) (0.009 g, 0.010 mmol), (±)-BINAP (0.019 g, 0.031 mmol), potassium tert-butoxide (0.069 g, 0.617 mmol) and triethylamine (0.005 g, 0.051 mmol) were added, and the mixture was stirred at 110° C. for 24 hr. The reaction mixture was allowed to cool to room temperature and filtered through celite. The filtrate was concentrated under reduced pressure, and the obtained residue was purified by silica gel column chromatography (hexane/ethyl acetate=3/1) to give the title compound (0.029 g, 48%).

(Step 2)

2-(4-fluorophenyl)-2,6-diazaspiro[3,3]heptane tert-Butyl 6-(4-fluorophenyl)-2,6-diazaspiro[3,3]heptane-2-carboxylate (0.029 g, 0.098 mmol) obtained in step 1 was dissolved in dichloromethane (0.3 mL), and trifluoroacetic acid (0.11 mL, 1.467 mmol) was added. The mixture was stirred at room temperature for 5 hr, and saturated aqueous sodium hydrogen carbonate solution was added to quench the reaction. The organic layer was separated, and the aqueous layer was extracted with chloroform. The organic layers were combined, washed with saturated brine, dried over anhydrous sodium sulfate, and concentrated under reduced pressure to give the title compound (0.013 g, 68%).

ESI-MS m/z: 193 (M+H)+; 1H-NMR (CDCl3, δ): 2.51 (s, 1H), 3.81-3.98 (m, 8H), 6.34-6.44 (m, 2H), 6.87-6.95 (m, 2H).

INDUSTRIAL APPLICABILITY

The present invention provides a pyrazolopyrimidine derivative or a pharmaceutically acceptable salt thereof useful as an agent for the prevention and/or treatment of skin diseases, and the like.

The invention claimed is:
1. A pyrazolopyrimidine derivative represented by the formula (I)

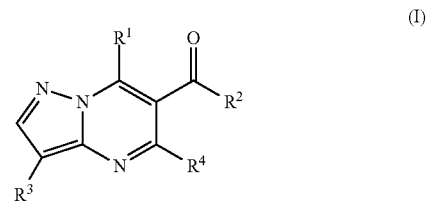

{wherein $R^1$ represents —$NR^{1a}R^{1b}$ (wherein $R^{1a}$ and $R^{1b}$ are the same or different and each represents a hydrogen atom, lower alkyl optionally having substituent(s), cycloalkyl optionally having substituent(s), lower alkoxy optionally having substituent(s), lower alkanoyl optionally having substituent(s), aryl optionally having substituent(s), aralkyl optionally having substituent(s), an aromatic heterocyclic group optionally having substituent(s) or an aliphatic heterocyclic group optionally having substituent(s), or $R^{1a}$ and $R^{1b}$ form, together with the adjacent nitrogen atom, a nitrogen-containing heterocyclic group optionally having substituent(s)), —$OR^{1c}$ (wherein $R^{1c}$ represents a hydrogen atom, lower alkyl optionally having substituent(s), cycloalkyl optionally having substituent(s), aryl optionally having substituent(s), aralkyl optionally having substituent(s), an aromatic heterocyclic group optionally having substituent(s) or an aliphatic heterocyclic group optionally having substituent(s)) or —$SR^{1d}$ (wherein $R^{1d}$ is as defined for the aforementioned $R^{1c}$),
$R^2$ represents

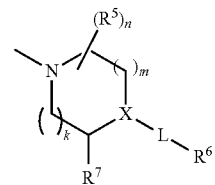

[wherein k and m each represents an integer of 0-2 (wherein the total of k and m is not more than 3),
n represents an integer of 0-4, and when n is 2, 3 or 4, respective $R^5$ may be the same or different,
L represents a single bond, alkylene, C(=O) or $SO_2$,
$R^5$ represents halogen, hydroxy, lower alkyl optionally having substituent(s) or lower alkoxy optionally having substituent(s),
$R^6$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s),
X represents a nitrogen atom or —$CR^8$ (wherein $R^8$ represents a hydrogen atom, halogen, hydroxy, cyano, lower alkyl optionally having substituent(s) or lower alkoxy optionally having substituent(s), or forms a bond together with $R^7$), and $R^7$ forms a bond together with $R^8$, or represents a hydrogen atom, halogen, hydroxy, lower alkyl optionally having substituent(s) or lower alkoxy optionally having substituent(s)],

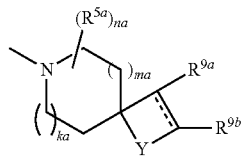

[wherein ka, ma and na are as defined for the aforementioned k, m and n, respectively, $R^{5a}$ is as defined for the aforementioned $R^5$, --- represents a single bond or a double bond, $R^{9a}$ and $R^{9b}$ are the same or different and each represents a hydrogen atom or lower alkyl optionally having substituent(s), or $R^{9a}$ and $R^{9b}$ form, together with the respectively adjacent carbon atoms, an aliphatic ring optionally having substituent(s) or an aromatic ring optionally having substituent(s), Y represents —$CHR^{10a}$—$CHR^{10b}$— (wherein $R^{10a}$ and $R^{10b}$ are the same or different and each represents a hydrogen atom, hydroxy, lower alkyl optionally having substituent(s) or lower alkoxy optionally having substituent(s), or $R^{10a}$ and $R^{10b}$ form, together with the respectively adjacent carbon atoms, an aliphatic ring optionally having substituent(s)), —$CR^{10c}$=$cR^{10d}$— (wherein $R^{10c}$ and $R^{10d}$ are the same or different and each represents a hydrogen atom or lower alkyl optionally having substituent(s), or $R^{10c}$ and $R^{10d}$ form, together with the respectively adjacent carbon atoms, an aliphatic ring having at least one double bond and optionally having substituent(s) or an aromatic ring optionally having substituent(s)), —$Z^a$—$CR^{11a}R^{11b}$— [wherein $R^{11a}$ and $R^{11b}$ are the same or different and each represents a hydrogen atom or lower alkyl optionally having substituent(s), or $R^{11a}$ and $R^{11b}$ form carbonyl together with the adjacent carbon atom, $Z^a$ represents C(=O), O, S, SO, $SO_2$ or $NR^{12}$ (wherein $R^{12}$ represents a hydrogen atom, lower alkyl optionally having substituent(s), lower alkanoyl optionally having substituent(s), lower alkoxycarbonyl optionally having substituent(s) or aralkyl optionally having substituent(s))], or —$CR^{11c}R^{11d}$—$Z^b$— (wherein $R^{11c}$, $R^{11d}$ and $Z^b$ are as defined for the aforementioned $R^{11a}$, $R^{11b}$ and $Z^a$, respectively)], or

(wherein $R^z$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s), $R^{5b}$ and $R^{7b}$ are the same or different and each represents halogen, hydroxy, lower alkyl optionally having substituent(s) or lower alkoxy optionally having substituent(s), nb represents an integer of 0-2, nc represents an integer of 0-2, when nb is 2, respective $R^{5b}$ are the same or different, when nc is 2, respective $R^{7b}$ are the same or different), $R^3$ represents —$S(O)_2R^{13a}$ [wherein $R^{13a}$ represents —$NR^{13b}R^{13c}$ (wherein $R^{13b}$ and $R^{13c}$ are the same or different and each represents a hydrogen atom, lower alkyl optionally having substituent(s), lower alkoxy optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), or $R^{13b}$ and $R^{13c}$ form, together with the adjacent nitrogen atom, a nitrogen-containing heterocyclic group optionally having substituent(s)), —$NR^{13d}C(=o)R^{13e}$ (wherein $R^{13d}$ represents a hydrogen atom, lower alkyl optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), $R^{13e}$ represents a hydrogen atom, lower alkyl optionally having substituent(s), cycloalkyl optionally having substituent(s), aralkyl optionally having substituent(s), lower alkoxy optionally having substituent(s), N-mono-lower alkylamino optionally having substituent(s), N,N-di-lower alkylamino optionally having substituent(s), N-cycloalkylamino optionally having substituent(s), N-mono-arylamino optionally having substituent(s), N,N-di-arylamino optionally having substituent(s), aryl optionally having substituent(s), an aromatic heterocyclic group optionally having substituent(s) or an aliphatic heterocyclic group optionally having substituent (s)), —$NR^{13f}C(=S)R^{13g}$ (wherein $R^{13f}$ and $R^{13g}$ are as defined for the aforementioned $R^{13d}$ and $R^{13e}$, respectively) or —$NR^{13h}S(O)_2R^{14}$ (wherein $R^{13h}$ is as defined for the aforementioned $R^{13d}$, $R^{14}$ represents lower alkyl optionally having substituent(s), cycloalkyl optionally having substituent(s), N-mono-lower alkylamino optionally having substituent(s), N,N-di-lower alkylamino optionally having substituent(s), aryl optionally having substituent(s), aralkyl optionally having substituent(s), an aromatic heterocyclic group optionally having substituent(s) or an aliphatic heterocyclic group optionally having substituent(s))], and $R^4$ represents a hydrogen atom, halogen, lower alkyl optionally having substituent(s), aralkyl optionally having substituent(s), —$NR^{15a}R^{15b}$ (wherein $R^{15a}$ and $R^{15b}$ are as defined for the aforementioned $R^{1a}$ and $R^{1b}$, respectively), —$OR^{15c}$ (wherein $R^{15c}$ is as defined for the aforementioned $R^{1c}$), or —$SR^{15d}$ (wherein $R^{15d}$ is as defined for the aforementioned $R^{1c}$)} or a pharmaceutically acceptable salt thereof.

2. A pyrazolopyrimidine derivative represented by the formula (IA)

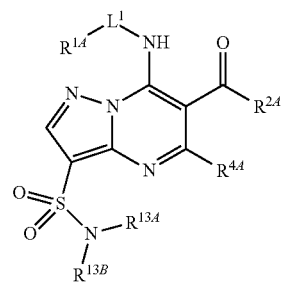

(IA)

{wherein $L^1$ represents a single bond or methylene, $R^{14}$ represents lower alkyl optionally having substituent(s), an aralkyl optionally having substituent(s), cycloalkyl optionally having substituent(s), aryl optionally having substituent(s), an aromatic heterocyclic group optionally having substituent(s) or an aliphatic heterocyclic group optionally having substituent(s), $R^{2A}$ represents

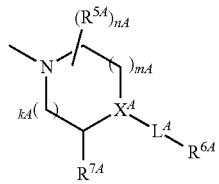

[wherein nA represents an integer of 0-2, and when nA is 2, respective $R^{5A}$s may be the same or different, kA, mA and $L^A$ are as defined for the aforementioned k, m and l, respectively, $R^{5A}$ represents halogen or lower alkyl, $R^{6A}$ represents cycloalkyl optionally having substituent(s), aryl optionally having substituent(s), an aromatic heterocyclic group optionally having substituent(s) or an aliphatic heterocyclic group optionally having substituent(s), $X^A$ represents a nitrogen atom or $-CR^{8A}$ (wherein $R^{8A}$ represents a hydrogen atom, halogen or lower alkyl, or forms a bond together with $R^{7A}$), and $R^{7A}$ forms a bond together with $R^{8A}$, or represents a hydrogen atom, halogen or lower alkyl],

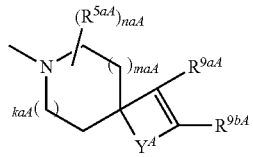

[wherein naA and $R^{5aA}$ are as defined for the aforementioned nA and $R^{5A}$, respectively, maA and kaA are as defined for the aforementioned ma and ka, respectively, $R^{9aA}$ and $R^{9bA}$ form, together with the respectively adjacent carbon atoms, an aromatic ring optionally having substituent(s), $Y^A$ represents $-CHR^{10aA}-CHR^{10bA}-$ (wherein $R^{10aA}$ and $R^{10bA}$ are the same or different and each represents a hydrogen atom, hydroxy, lower alkyl optionally having substituent(s) or lower alkoxy optionally having substituent(s)), $-CR^{10cA}=CR^{10dA}-$ (wherein $R^{10cA}$ and $R^{10dA}$ are the same or different and each represents a hydrogen atom or lower alkyl optionally having substituent(s)), $-Z^{aA}-CR^{11aA}R^{11bA}-$ [wherein $R^{11aA}$ and $R^{11bA}$ are the same or different and each represents a hydrogen atom or lower alkyl optionally having substituent(s), or $R^{11aA}$ and $R^{11bA}$ form carbonyl together with the adjacent carbon atom, $Z^{aA}$ represents $C(=O)$, O, S, SO, $SO_2$ or $NR^{12A}$ (wherein $R^{12A}$ represents a hydrogen atom, lower alkyl optionally having substituent(s), lower alkanoyl optionally having substituent(s), lower alkoxycarbonyl optionally having substituent(s) or aralkyl optionally having substituent(s))], or $-CR^{11cA}R^{11dA}-Z^{bA}-$ (wherein $R^{11cA}$, $R^{11dA}$ and $Z^{bA}$ are as defined for the aforementioned $R^{11aA}$, $R^{11bA}$ and $Z^{aA}$, respectively)}, or

(wherein $R^{zA}$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s), $R^{5bA}$ and $R^{7bA}$ are the same or different and each represents halogen, hydroxy, lower alkyl optionally having substituent(s) or lower alkoxy optionally having substituent(s), nbA represents an integer of 0-2, ncA represents an integer of 0-2, when nbA is 2, respective $R^{5bA}$ are the same or different and when ncA is 2, respective $R^{7bA}$ are the same or different), $R^{13A}$ represents a hydrogen atom, lower alkyl optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), or $R^{13A}$ and $R^{13B}$ form, together with the adjacent nitrogen atom, a nitrogen-containing heterocyclic group optionally having substituent(s), $R^{13B}$ represents a hydrogen atom, lower alkyl optionally having substituent(s), lower alkoxy optionally having substituent(s), cycloalkyl optionally having substituent(s), aralkyl optionally having substituent(s), aryl optionally having substituent(s), an aromatic heterocyclic group optionally having substituent(s), an aliphatic heterocyclic group optionally having substituent(s) or $COR^{13e1}$ (wherein $R^{13e1}$ is as defined for the aforementioned $R^{13e}$), or $R^{13B}$ and $R^{13A}$ form, together with the adjacent nitrogen atom, a nitrogen-containing heterocyclic group optionally having substituent(s), and $R^{4A}$ represents a hydrogen atom or lower alkyl optionally having substituent(s)}, or a pharmaceutically acceptable salt thereof.

3. The pyrazolopyrimidine derivative or the pharmaceutically acceptable salt thereof according to claim 2, wherein $L^1$ is a single bond.

4. The pyrazolopyrimidine derivative or the pharmaceutically acceptable salt thereof according to claim 2, wherein $R^{1A}$ is aryl optionally having substituent(s).

5. The pyrazolopyrimidine derivative or the pharmaceutically acceptable salt thereof according to claim 2, wherein $R^{1A}$ is phenyl optionally having substituent(s).

6. The pyrazolopyrimidine derivative or the pharmaceutically acceptable salt thereof according to claim 2, wherein $R^{1A}$ is an aromatic heterocyclic group optionally having substituent(s).

7. The pyrazolopyrimidine derivative or the pharmaceutically acceptable salt thereof according to claim 2, wherein $R^{4A}$ is a hydrogen atom.

8. The pyrazolopyrimidine derivative or the pharmaceutically acceptable salt thereof according to claim 2, wherein $R^{13A}$ is a hydrogen atom, and $R^{13B}$ is lower alkyl optionally having substituent(s).

9. The pyrazolopyrimidine derivative or the pharmaceutically acceptable salt thereof according to claim 2, wherein $R^{13A}$ is a hydrogen atom, and $R^{13B}$ is $COR^{13e1}$ (wherein $R^{13e1}$ is as defined above).

10. The pyrazolopyrimidine derivative or the pharmaceutically acceptable salt thereof according to claim 2, wherein $R^{13A}$ is a hydrogen atom, and $R^{13B}$ is $COR^{13e2}$ (wherein $R^{13e2}$ represents lower alkyl optionally having substituent(s), cycloalkyl optionally having substituent(s), N-mono-lower alkylamino optionally having substituent(s) or N-mono-arylamino optionally having substituent(s)).

11. The pyrazolopyrimidine derivative or the pharmaceutically acceptable salt thereof according to claim 2, wherein $R^{2A}$ is

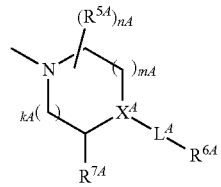

(wherein nA, mA, kA, $R^{5A}$, $R^{6A}$, $R^{7A}$, $L^A$ and $X^A$ are each as defined above).

12. The pyrazolopyrimidine derivative or the pharmaceutically acceptable salt thereof according to claim 11, wherein $R^{6A}$ is phenyl optionally having substituent(s).

13. The pyrazolopyrimidine derivative or the pharmaceutically acceptable salt thereof according to claim 2, wherein $R^{2A}$ is

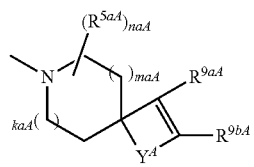

(wherein naA, maA, kaA, $R^{5aA}$, $R^{9aA}$, $R^{9bA}$ and $Y^A$ are each as defined above).

14. The pyrazolopyrimidine derivative or the pharmaceutically acceptable salt thereof according to claim 13, wherein $R^{9aA}$ and $R^{9bA}$ form, together with the respectively adjacent carbon atom, a benzene ring optionally having substituent(s), $Y^A$ is —CHR$^{10aA}$—CHR$^{10bA}$— (wherein R$^{10aA}$ and R$^{10bA}$ are each as defined above), —CR$^{10cA}$=CR$^{10dA}$— (wherein R$^{10cA}$ and R$^{10dA}$ are each as defined above), —O—CR$^{11aA}$R$^{11bA}$— (wherein R$^{11aA}$ and R$^{11bA}$ are each as defined above) or —CR$^{11cA}$R$^{11dA}$—O— (wherein R$^{11cA}$ and R$^{11dA}$ are each as defined above).

15. The pyrazolopyrimidine derivative or the pharmaceutically acceptable salt thereof according to claim 2, wherein $R^{2A}$ is

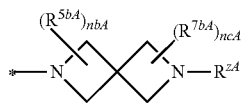

(wherein $R^{zA}$, $R^{5bA}$, $R^{7bA}$, nbA and ncA are each as defined above).

16. The pyrazolopyrimidine derivative or the pharmaceutically acceptable salt thereof according to claim 15, wherein $R^{zA}$ is phenyl optionally having substituent(s).

17. A medicament comprising, as an active ingredient, the pyrazolopyrimidine derivative or the pharmaceutically acceptable salt thereof according to claim 2.

18. The pyrazolopyrimidine derivative or the pharmaceutically acceptable salt thereof according to claim 2, which is N-[7-(2-chlorophenylamino)-6-(4-phenylpiperidine-1-carbonyl)pyrazolo[1,5-a]pyrimidin-3-ylsulfonyl]cyclopropanecarboxamide or a pharmaceutically acceptable salt thereof.

19. The pyrazolopyrimidine derivative or the pharmaceutically acceptable salt thereof according to claim 2, which is 7-(2-chloro-5-methylphenylamino)-N-(ethylcarbamoyl)-6-[4-(4-fluorophenyl)piperidine-1-carbonyl]pyrazolo[1,5-a]pyrimidine-3-sulfonamide or a pharmaceutically acceptable salt thereof.

20. The pyrazolopyrimidine derivative or the pharmaceutically acceptable salt thereof according to claim 2, which is 7-(4-fluoro-2-methylphenylamino)-N-(ethylcarbamoyl)-6-[3H-spiro(isobenzofuran-1,4'-piperidine)-1-carbonyl]pyrazolo[1,5-a]pyrimidine-3-sulfonamide or a pharmaceutically acceptable salt thereof.

21. The pyrazolopyrimidine derivative or the pharmaceutically acceptable salt thereof according to claim 2, which is N-{7-(2,5-dichlorophenylamino)-6-[4-(4-fluorophenyl)piperidine-1-carbonyl]pyrazolo[1,5-a]pyrimidin-3-ylsulfonyl}propionamide or a pharmaceutically acceptable salt thereof.

22. The pyrazolopyrimidine derivative or the pharmaceutically acceptable salt thereof according to claim 2, which is 7-(2,5-dichlorophenylamino)-6-[4-(4-fluorophenyl)piperidine-1-carbonyl]-N-methoxypyrazolo[1,5-a]pyrimidine-3-sulfonamide or a pharmaceutically acceptable salt thereof.

23. The pyrazolopyrimidine derivative or the pharmaceutically acceptable salt thereof according to claim 2, which is N-{7-(2-chloro-4-fluoro-5-methylphenylamino)-6-[4-(4-fluorophenyl)piperidine-1-carbonyl]pyrazolo[1,5-a]pyrimidin-3-ylsulfonyl}propionamide or a pharmaceutically acceptable salt thereof.

24. The pyrazolopyrimidine derivative or the pharmaceutically acceptable salt thereof according to claim 2, which is N-{7-(2-chloro-5-methylphenylamino)-6-[6-(4-fluorophenyl)-2,6-diazaspiro[3,3]heptane-2-carbonyl]pyrazolo[1,5-a]pyrimidin-3-ylsulfonyl}propionamide or a pharmaceutically acceptable salt thereof.

25. A method for the prevention and/or treatment of a skin disease, comprising a step of administering an effective amount of the pyrazolopyrimidine derivative or the pharmaceutically acceptable salt thereof according to any one of claims 18-24 to a subject in need thereof.

26. The method according to claim 25, wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

27. The method according to claim 25, wherein the skin disease is dermatitis.

28. The method according to claim 25, wherein the skin disease is a skin disease selected from contact dermatitis and atopic dermatitis.

* * * * *